US012595227B2

(12) United States Patent
Zhu et al.

(10) Patent No.: US 12,595,227 B2
(45) Date of Patent: Apr. 7, 2026

(54) COMPOSITIONS AND METHODS FOR TREATMENT OF PLATINUM-BASED CHEMOTHERAPEUTIC RESISTANT TUMORS

(71) Applicant: The George Washington University, Washington, DC (US)

(72) Inventors: Wenge Zhu, Germantown, MD (US); Jing Li, Arlington, VA (US); Ruiqin Wu, Sichuan (CN); Yiliang Li, Hebei (CN)

(73) Assignee: The George Washington University, Washington, DC (US)

( * ) Notice: Subject to any disclaimer, the term of this patent is extended or adjusted under 35 U.S.C. 154(b) by 681 days.

(21) Appl. No.: 17/892,948

(22) Filed: Aug. 22, 2022

(65) Prior Publication Data

US 2023/0012172 A1 Jan. 12, 2023

Related U.S. Application Data

(63) Continuation of application No. PCT/US2021/020866, filed on Mar. 4, 2021.

(60) Provisional application No. 62/985,128, filed on Mar. 4, 2020.

(51) Int. Cl.

| | |
|---|---|
| ***C07C 233/58*** | (2006.01) |
| ***A61K 31/16*** | (2006.01) |
| ***A61K 31/22*** | (2006.01) |
| ***A61K 31/27*** | (2006.01) |
| ***C07C 235/26*** | (2006.01) |
| ***C07C 235/74*** | (2006.01) |
| ***C07C 235/88*** | (2006.01) |

(52) U.S. Cl.

CPC ............ *C07C 233/58* (2013.01); *A61K 31/16* (2013.01); *A61K 31/22* (2013.01); *A61K 31/27* (2013.01); *C07C 235/26* (2013.01); *C07C 235/74* (2013.01); *C07C 235/88* (2013.01)

(58) Field of Classification Search

CPC .................................................... C07C 233/58

See application file for complete search history.

(56) References Cited

U.S. PATENT DOCUMENTS

2017/0298090 A1 10/2017 Ding et al.

FOREIGN PATENT DOCUMENTS

| | | | | |
|---|---|---|---|---|
| CN | 110627860 A | * 12/2019 | | A61P 35/00 |
| CN | 110680820 A | 1/2020 | | |

OTHER PUBLICATIONS

Lin, K.-W. et al., "Anti-cancer effects of ursane triterpenoid as a single agent and in combination with cisplatin in bladder cancer", European journal of pharmacology, 2014, vol. 740, pp. 742-751.

Li, L. et al., "Synergism of ursolic acid and cisplatin promotes apoptosis and enhances growth inhibition of cervical cancer cells via suppressing NE-KB p65", Oncotarget, 2017, vol. 8, No. 57, pp. 97416-97427.

* cited by examiner

*Primary Examiner* — Svetlana M Ivanova
(74) *Attorney, Agent, or Firm* — Kory D. Christensen

(57) ABSTRACT

Embodiments of the instant disclosure relate to novel methods and compositions for treating tumors resistant to platinum-based chemotherapy. In certain embodiments, methods of treating tumors herein can include administering an effective amount of at least one ursolic acid derivative. In certain embodiments, methods of treating tumors herein can include administering an effective amount of at least one ursolic acid derivative in combination with at least one platinum-based chemotherapeutic separately or in a combination therapy. In some embodiments, methods of treating tumors disclosed herein can include screening and/or selecting a subject suitable for treatment on the basis of SENP1 tumor expression. In other embodiments, methods of treating tumors can include administering a composition disclosed herein to a subject, the composition having a combination of at least one ursolic acid derivative and at least one platinum-based chemotherapeutic.

13 Claims, 43 Drawing Sheets
(33 of 43 Drawing Sheet(s) Filed in Color)

Class I

Class II

Class IV

Ursolic Acid

Class III

Class III

Fig. 2A
JAK2 purification
| Accession # | Protein | Peptides | Coverage (%) |
|---|---|---|---|
| P40763 | STAT3 | 19 | 35.25 |
| Q92783 | STAM | 14 | 26.09 |
| P42229 | STAT5A | 10 | 28.38 |
| Q5VWK5 | IL23R | 9 | 22.94 |
| Q9P0U3 | SENP1 | 8 | 14.64 |
| P42224 | STAT1 | 7 | 13.43 |
| O14744 | PRMT5 | 7 | 13.17 |
| Q05209 | PTPN12 | 6 | 14.25 |
| Q15910 | EZH2 | 5 | 9.40 |
| P15260 | IFNGR1 | 5 | 9.09 |
Fig. 2B
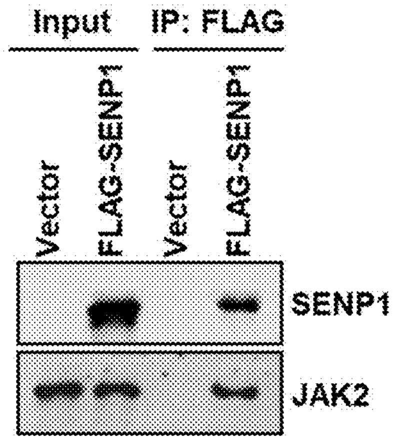
Fig. 2C
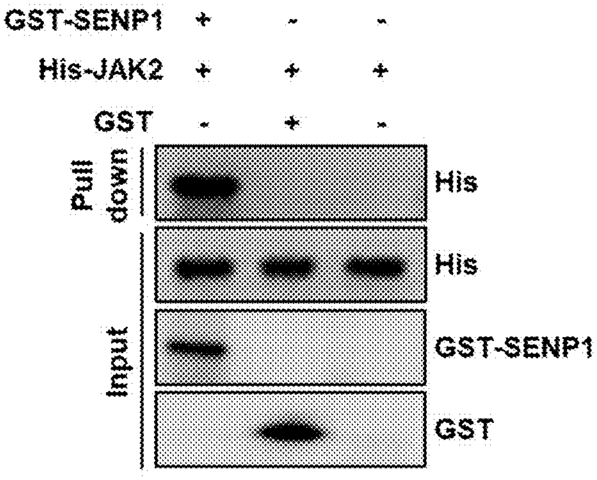

| No | Pos | Group | Score |
|---|---|---|---|
| 1 | K167 | FVHGWIKVPVTHET | 0.84 |
| 2 | K1011 | KEYYKVKEPGESPI | 0.82 |
| 3 | K273 | TEKFEVKEPGSGPS | 0.82 |
| 4 | K991 | ENENRVKIGDFGLT | 0.76 |
| 5 | K630 | LVQEFVKFGSLDTY | 0.76 |

Pomolic acid

Tormentic acid

| | Cisplatin IC50 (μm) |
|---|---|
| Cisplatin | 28.23 |
| Cisplatin+ Corosolic acid | 26.42 |
| Cispaltin+ Echinocyslic acid | 21.47 |
| Cispaltin+ Pomolic acid | 3.688 |
| Cispaltin+ Tormentic acid | 2.397 |

Oleanolic acid
IC50: 8.1μM

Polygalacic acid
IC50: 24.5μM

Betulinic acid
IC50: 4.6μM 2,3-Hydroxybetulinic acid
IC50: 8.6μM

Bambuterol
IC50: 23.1μM

Momordin Ic (Mc)

Ursolic acid
IC50: 0.86μM

Triptonide
IC50: 1.37μM

Asiatic acid
IC50: 17.6μM

Glycyrrhizic acid
IC50: 8.9μM

Ziyuglycoside I
IC50: 16.5μM

Ziyuglycoside II
IC50: 3.7μM

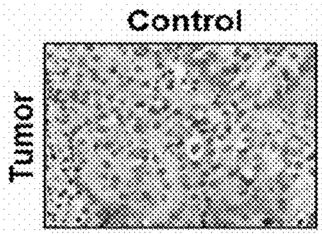
Fig. 13Q
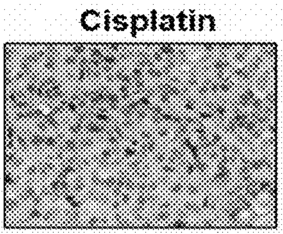
Fig. 13R
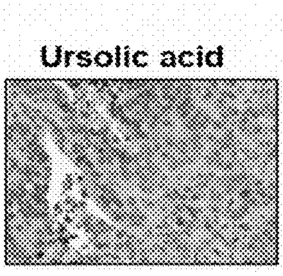
Fig. 13S
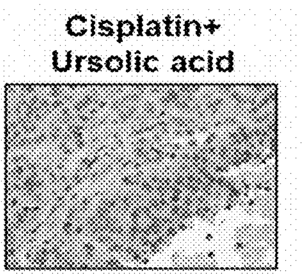
Fig. 13T
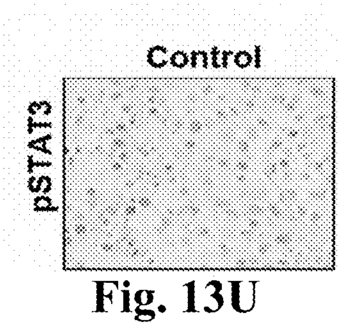
Fig. 13U
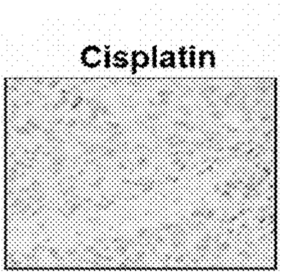
Fig. 13V
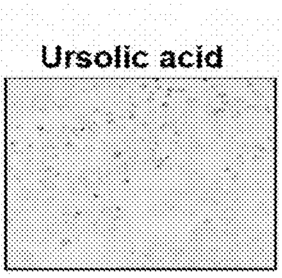
Fig. 13W
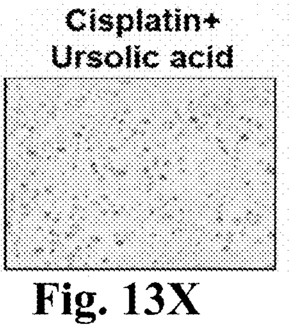
Fig. 13X
Fig. 13Y
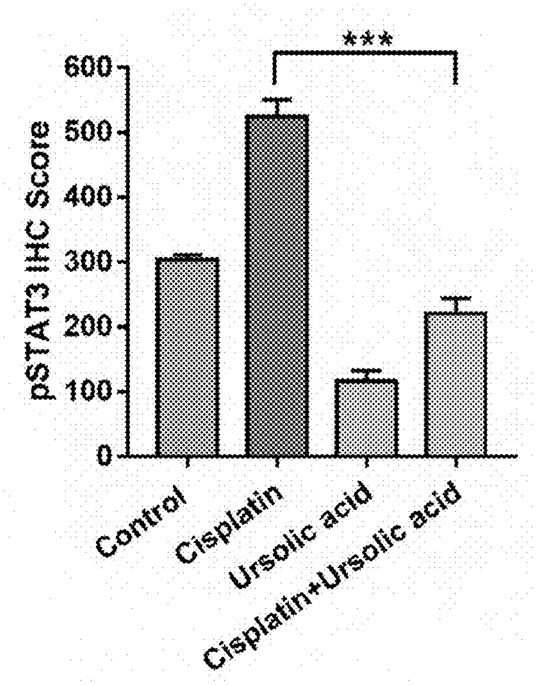

COMPOSITIONS AND METHODS FOR TREATMENT OF PLATINUM-BASED CHEMOTHERAPEUTIC RESISTANT TUMORS

CROSS-REFERENCE TO RELATED APPLICATIONS

This application is a continuation of PCT App. No. PCT/US21/20866, filed Mar. 4, 2021, for COMPOSITIONS AND METHODS FOR TREATMENT OF PLATINUM-BASED CHEMOTHERAPEUTIC RESISTANT TUMORS, which claims the benefit of U.S. Provisional App. No. 62/985,128, filed Mar. 4, 2020, both of which are incorporated herein by reference.

GOVERNMENTAL RIGHTS

This invention was made with government support under CA177898 awarded by the National Institutes of Health. The government has certain rights in the invention.

FIELD

The present disclosure generally relates to compositions and methods for the treatment of tumor cells, prevention of tumor cell metastasis, and treatment and prevention of cancers and of cancers resistant to platinum-based chemotherapeutics.

BACKGROUND

Platinum-based chemotherapy regimens are frequently a standard of care for cancer patients, particularly those with late stage cancer and metastatic disease. A tumor that responds to a first treatment with drugs that contain the metal platinum, such as cisplatin, only to have the tumor return within a certain period is considered a platinum-resistant tumor. Patients with platinum-sensitive tumors are often re-treated with platinum, but a substantial percentage of these patients have a short duration of response after re-treatment and then resistance is developed. For those with platinum-resistant cancers, positive outcomes are very likely be low.

The JAK2/STAT pathway is hyperactivated in many cancers, and such hyperactivation is associated with a poor clinical prognosis and platinum drug resistance. Although many JAK2 inhibitors have entered clinic trials, most have been discontinued due to drug toxicity and lack of target specificity. As such, there is a need in the art for cancer therapies that target other pathways regulating JAK2 activity that can also be administered in combination with platinum-based chemotherapy regimens.

SUMMARY

Embodiments of the instant disclosure relate to novel methods and unique compositions for treating cancers, tumors (e.g., solid tumors), tumors resistant to platinum-based chemotherapy, and/or tumors suspected of developing platinum-based chemotherapy resistance in a subject.

In some aspects, the present disclosure provides for methods of treating a tumor. In some embodiments, methods of treating a tumor herein can include administering to a subject in need thereof an ursolic acid derivative wherein the subject is undergoing or will undergo an anti-cancer therapy comprising one or more platinum-based chemotherapeutic and treating the tumor in the subject. In some embodiments, the one or more platinum-based chemotherapeutic can be one or more of cisplatin, carboplatin, nedaplatin, satraplatin, picoplatin, phenanthriplatin, triplatin tetranitrate.

In some embodiments, an ursolic acid derivative for use in methods herein can be a compound represented by formula I or a pharmaceutically acceptable salt thereof:

(I)

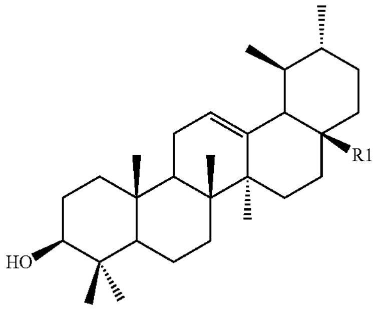

wherein R1 is selected from the group consisting of hydrogen, hydroxyl, hydroxymethyl, formyl, or

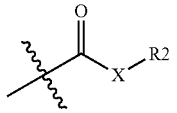

wherein X is NH or O or S, and $R_2$ is hydrogen, unsubstituted or substituted $C_1$-$C_6$ alkyl.

In some embodiments, an ursolic acid derivative for use in methods herein can be a compound represented by formula II or a pharmaceutically acceptable salt thereof:

(II)

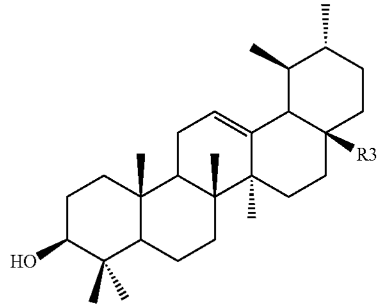

wherein R3 is selected from the group consisting of

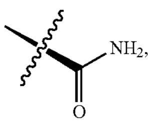

,

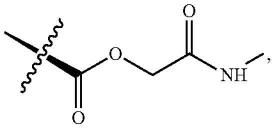

,

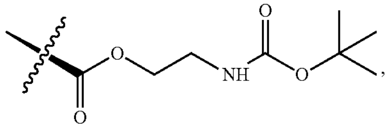

,

-continued

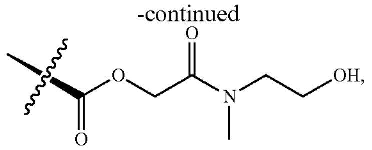

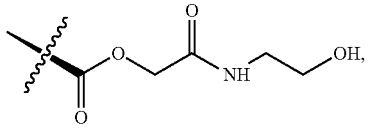

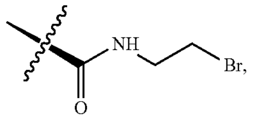

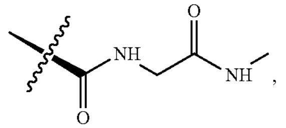

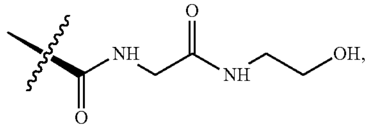

or

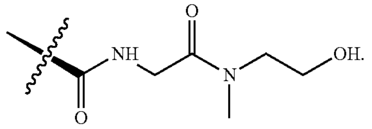

In some embodiments, an ursolic acid derivative for use in methods herein can be

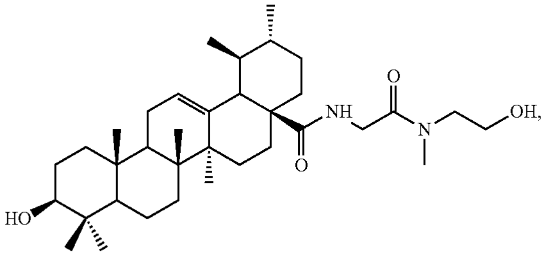

or a pharmaceutically acceptable salt thereof.

In some embodiments, methods of treating a tumor herein can be used to treat one ore more platinum-resistant metastatic solid tumors. In some embodiments, methods of treating a tumor herein can be used to treat one or more solid tumors such as a testicular tumor, ovarian tumor, cervical tumor, kidney tumor, bladder tumor, head-and-neck tumor, liver tumor, stomach tumor, lung tumor, endometrial tumor, esophageal tumor, breast tumor, cervical tumor, central nervous system tumor, germ cell tumor, prostate tumor, Hodgkin's lymphoma, non-Hodgkin's lymphoma, neuroblastoma, sarcoma, multiple myeloma, melanoma, mesothelioma, osteogenic sarcoma, or any combination thereof. In some examples, methods of treating a tumor herein can be used to treat ovarian tumors.

In some other aspects, the present disclosure provides for methods of treating a solid tumor by administering to a subject in need thereof an effective amount of any one of the ursolic acid derivatives disclosed herein when the subject is undergoing an anti-cancer therapy of one or more platinum-based chemotherapeutics. In some embodiments, methods of treating a solid tumor can include examining sentrin-specific protease 1 (SENP1) in a tumor biopsy sample from the subject during and/or after an anti-cancer therapy. In some embodiments, SENP1 expression in a tumor biopsy sample from the subject can be elevated compared to a control biopsy sample from a healthy subject.

In some embodiments, methods of treating a solid tumor herein can include methods of treating a metastatic solid tumor. In some embodiments, a solid tumor or a metastatic solid tumor treated using the methods herein can be a testicular tumor, ovarian tumor, cervical tumor, kidney tumor, bladder tumor, head-and-neck tumor, liver tumor, stomach tumor, lung tumor, endometrial tumor, esophageal tumor, breast tumor, cervical tumor, central nervous system tumor, germ cell tumor, prostate tumor, Hodgkin's lymphoma, non-Hodgkin's lymphoma, neuroblastoma, sarcoma, multiple myeloma, melanoma, mesothelioma, osteogenic sarcoma or a combination thereof. In some examples, a solid tumor or a metastatic solid tumor treated using the methods herein can be an ovarian tumor.

In some embodiments, methods of treating a solid tumor herein can further include monitoring for occurrence of one or more adverse effects in the subject before, during or after treatment of the subject. In some embodiments, the one or more adverse effects can include hepatic impairment, hematologic toxicity, neurologic toxicity, cutaneous toxicity, gastrointestinal toxicity, or any combination thereof.

In some embodiments, methods of treating a solid tumor herein can further include adjusting the dosing regimen by increasing or decreasing the dosing regimen or dosing concentration of any one of the ursolic acid derivatives disclosed herein, the dose of the one or more platinum-based chemotherapeutics, or both, when an adverse effect is observed.

In some aspects, the present disclosure provides for compositions for treating cancer. In some embodiments, compositions for treating cancer disclosed herein can include one or more of the ursolic acid derivatives described herein and one or more platinum-based chemotherapeutics. In some embodiments, the one or more platinum-based chemotherapeutics of the compositions herein can be one or more of cisplatin, carboplatin, nedaplatin, satraplatin, picoplatin, phenanthriplatin, triplatin tetranitrate.

In some embodiments, compositions for treating cancer herein can further include one or more of gemcitabine, methotrexate, vinblastine, Adriamycin, and the like. In some embodiments, compositions for treating cancer herein can further include one or more pharmaceutically acceptable excipients.

In some other aspects, the present disclosure provides for compounds. In some embodiments, compounds disclosed herein can be represented by formula I or a pharmaceutically acceptable salt thereof:

(I)

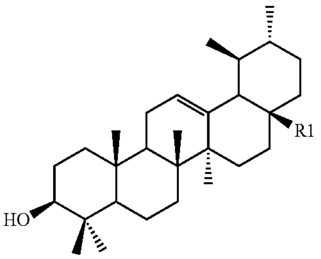

wherein R1 is selected from the group consisting of hydrogen, hydroxyl, hydroxymethyl, formyl, or

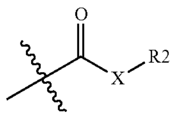

wherein X is NH or O or S, and $R_2$ is hydrogen, unsubstituted or substituted $C_1$-$C_6$ alkyl.

In some embodiments, compounds disclosed herein can be represented by formula II or a pharmaceutically acceptable salt thereof:

(II)

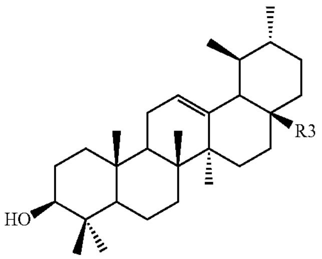

wherein R3 is selected from the group consisting of

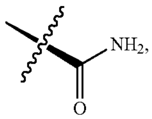
,
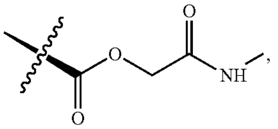
,
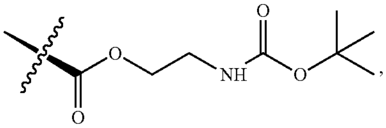
,
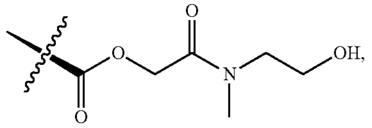
,
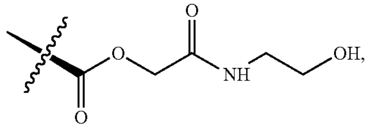
,
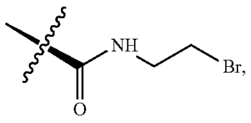
,
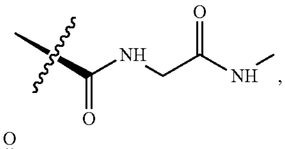
,
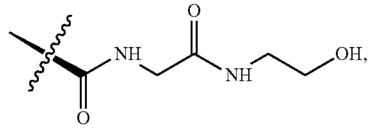
, or
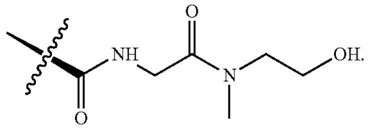
.

In certain embodiments, the present disclosure includes pharmaceutical compositions including at least one of the ursolic acid derivatives herein (e.g., compounds represented by Formula I, Formula II). In some embodiments, pharmaceutical compositions including at least one of the ursolic acid derivatives herein can further include at least one pharmaceutically acceptable excipient. In some embodiments, pharmaceutical compositions including at least one of the ursolic acid derivatives herein can further include one or more platinum-based chemotherapeutics described herein.

In certain embodiments, kits are provided herein. In certain embodiments, compositions of the instant disclosure can be included in the kit, together or in separate containers. In certain embodiments, kits are provided for the practice of any one of the methods disclosed herein. In some embodiments, kits can include one or more of the ursolic acid derivatives herein (e.g., compounds represented by Formula I, Formula II), one or more platinum-based chemotherapeutics, or a combination thereof.

BRIEF DESCRIPTION OF THE FIGURES

The patent or application file contains at least one drawing executed in color. Copies of this patent or patent application with color drawing(s) will be provided by the Office by request and payment of the necessary fee.

FIGS. 2A-2G depict images illustrating direct SENP1 interaction with and deSUMOylation of JAK2. FIG. 2A shows a mass spectrometry analysis to identify JAK2 associated proteins. Immunoprecipitation of His-tagged JAK2 from HEK293T cells was used for mass-spec analysis. Results represented the proteins identified in cells expressing His-hJAK2 compared cells expressing empty vector. Peptides were filtered to exclude false positives. FIG. 2B shows SENP1 interaction with JAK2 in vivo. Co-IPs of Flag-SENP1 were analyzed by Western blot using indicated antibodies. FIG. 2C shows SENP1 interaction with JAK2 in vitro. Recombinant GST-SENP1 was used to capture His-JAK2 protein on glutathione agarose as described herein. FIG. 2D shows SENP1 knockdown increased JAK2 SUMOylation in PEO1, PEO14, IGROV1 and U2OS cell lines. SUMOylated JAK2 was captured by using immunoprecipitation (IP) with anti-JAK2 antibody, followed by Western blot using antibodies against SUMO2/3. FIG. 2E shows that ectopic expression of SENP1-WT restored JAK2 deSUMOylation in SENP1 knockdown IGROV1 cells. SUMOylated JAK2 was detected as in FIG. 2D. FIG. 2F shows SENP1 deSUMOylation of JAK2 in vitro. Recombinant GST-SENP1 and His-JAK2 were used in SUMOylation assay as described herein. FIG. 2G shows SENP1-C603A failed to deSUMOylate JAK2 in vitro. Recombinant GST-SENP1, GST-SENP1-C603A and His-JAK2 were used in the SUMOylation assay.

FIG. 3A shows cellular distribution of JAK2 in IGROV1 cells treated with siSENP1 or siSENP1 with ectopic expression of siRNA resistant SENP1. JAK2 localization was detected by immunofluorescence assay using anti-JAK2 antibody. Right panel, SENP1 expression in treated cells. FIG. 3B shows quantification of JAK2 cellular distribution in IGROV1 cells as shown in FIG. 3A. 100 cells were counted in each sample. *, $p<0.001$. FIG. 3C shows nuclear fractionation of IGROV1 cells treated with siGL2 or siSENP1, followed by Western blot for indicated proteins. FIG. 3D shows SENP1 knockdown decreased expression of pSTAT3 (Tyr705) and Bcl-Xl. IGROV1 cells treated with indicated siRNAs, followed by Western blot with indicated proteins. FIG. 3E shows SENP1 knockdown decreased pSTAT3 (Tyr705) by JAK2 in vitro. Recombinant STAT3 was incubated with purified JAK2 from IGROV1 cells treated with siRNAs or JAK2 inhibitor (TG101348) for in vitro kinase assay as described herein. Cells lysates were resolved in SDS-PAGE gel, followed by Western blot for the indicated proteins. Right panel, quantification of pSTAT3 (Tyr705) levels in three independent experiments. *, $p<0.001$. FIG. 3F shows a schematic diagram of the distribution of putative JAK2 SUMOylation sites, predicted by SUMOplot. The score indicates the probability. FIG. 3G shows JAK2-SUMO mutant clones 1 and 2 failed to be SUMOylated in vitro. Recombinant His-JAK2 proteins were used for in vitro SUMOylation assay as described herein. FIG. 3H shows JAK2-SUMO mutant phosphorylated STAT3 (Tyr705) in vitro. Empty vector, His-JAK2 and His-JAK2 SUMO mutant were purified from HEK293T cells, followed by in vitro kinase assay as in FIG. 3E. FIG. 3I shows the JAK2-SUMO mutant accumulated in cytoplasm. Empty vector, His-JAK2 and His-JAK2 SUMO mutant were transfected in IGROV1 cells, followed by immunofluorescence assay using anti-His antibody. Right panel, expression of JAK2 and JAK2-SUMO mutant. FIG. 3J shows quantification of cellular distribution of JAK2 in IGROV1 cells as shown in FIG. 3I. 100 cells were counted in each sample. ***, $p<0.001$.

FIG. 4A shows a volcano plot of up-regulated and down-regulated genes identified from RNA-Seq assay using IGROV1 and IGROV1 CR (cisplatin resistant) cells. Genes were ranked in volcano plot according to their p-value and relative abundance ratio (log 2 fold change). FIG. 4B shows a volcano plot of up-regulated and down-regulated genes identified by quantitative proteomics using IGROV1 and IGROV1 CR cells. Proteins were ranked in volcano plot according to their p-value and their relative abundance ratio (log 2 fold change). FIG. 4C shows SENP1 mRNA expression levels were significantly upregulated in cisplatin resistant ovarian cancer cell lines. mRNA expression levels were assessed by qPCR. FIG. 4D shows SENP1 protein levels were upregulated in indicated paired cisplatin sensitive and resistant ovarian cancer cell lines. Cell lysates from indicated cells were Western blotted for indicated proteins. FIG. 4E shows SUMOylation of JAK2 decreased in cisplatin-resistant IGROV1 cells. Cell lysates from IGROV1 and IGROV1 CR cells were Western blotted for indicated proteins. FIG. 4F shows SUMOylation of JAK2 decreased in IGROV1 cells treated with cisplatin. Cell lysates of IGROV1 CR cells treated with cisplatin at indicated time point were Western blotted for indicated proteins. FIG. 4G shows IGROV1 cells that were treated with indicated amount of cisplatin, followed by Western blot for indicated proteins. FIGS. 4H-4J shows representative IHC images of IGROV1 xenograft tumors treated with vehicle (FIG. 4H) and carboplatin (20 mg/kg (FIG. 4I) and 60 mg/kg (FIG. 4J)). Scale bar: 50 μm. FIG. 4K shows quantification of IHC staining for SENP1 in carboplatin treated mice. n=5 mice/group. Data were represented as means±SD (n=3). **, $p<0.01$.

FIG. 5A shows a heat map of transcription factors of SENP1 in IGROV1 CR/IGROV1 cells. FIG. 5B shows a heat map of transcription factors of SENP1 in SKOV3 CR/SKOV3 cells. Transcriptional factors were identified from the Harmonizome database and matched with their mRNA expression values by RNA-Seq analyses. Colors in both heat maps represented the mRNA expression levels after z-score normalization across different samples. FIG. 5C shows SENP1 protein expression levels in IGROV1 CR cells treated with siGL2 or siRUNX2. FIGS. 5D and 5E shows a ChIP assay detecting the association of RUNX2 with promoter regions of SENP1 in IGROV1 CR cells (FIG. 5D) and SKOV3 CR cells (FIG. 5E). Cells were harvested and cell lyses were immunoprecipitated against IgG and anti-RUNX2 antibodies. RUNX2-associated DNA were examined by qPCR. Data were represented as mean±SD (n=3).

FIG. 6A shows SENP1 mRNA expression level in platinum-sensitive and -resistant ovarian cancer patients. Number of patients evaluated: 61 (platinum-sensitive), 32 (platinum-resistant). mRNA expression levels were assessed by qPCR. **, $p<0.01$. FIG. 6B shows Kaplan-Meier analyses of 5-year overall survival rates of patients as shown in FIG. 6A. FIGS. 6C-6F show representative SENP1 IHC staining from the same patient before (FIG. 6C) and after development of chemoresistance (FIG. 6D) and phospho-JAK2 IHC staining from the same patient before (FIG. 6E) and after development of chemoresistance (FIG. 6F). FIGS. 6G and 6H show quantification of IHC scores from 6 patients for SENP1 IHC (FIG. 6G) and phosphorylated JAK2 (FIG. 6H). Data are represented as mean±SD. FIG. 6I shows Correlation of IHC scores between SENP1 and pJAK2 expression in samples from six patients. FIGS. 6J and 6K show Kaplan-Meier analyses of 5-year overall survival rates (FIG. 6J), and progression-free survival rates (FIG. 6K) based on clinical and molecular data from ovarian cancer patients (OS: n=1581; PFS: n=1435). Patients were stratified by SENP1 mRNA expression in their tumors. Medium survival, log-rank (Mantel-Cox) p values and hazard ratios (HR). 95% confidence interval in parentheses were shown.

FIG. 7A shows cell viability of SKOV3 CR treated with indicated siRNAs. Data are represented as mean±SD (n=3). FIG. 7B shows IGROV1 CR cells treated with indicated siRNAs. Data are represented as mean±SD (n=3). FIG. 7C shows ectopic expression of JAK2 restored cisplatin resistance in SENP1 depleted cells. IGROV1 CR cells treated with indicated siRNAs were transfected with vector JAK2 plasmids. Cell viability was analyzed by using cell viability assay as described in Materials and Methods. FIG. 7D shows the expression of indicated proteins in cells treated in FIG. 7C.

FIGS. 8A-8C show the synergistic effects of cisplatin and Momordin Ic in SKOV3 CR (FIG. 8A), PEO4 (FIG. 8B), and PEO23 (FIG. 8C) cells. Concentrations of cisplatin and Momordin Ic as well as the CI index were indicated. Data were represented as mean±SD (n=3). FIG. 8D shows representative colony formation. FIG. 8E shows quantification of IGROV1 CR cells treated with cisplatin and Momordin. Colonies were stained with crystal violet. Data are represented as mean±SD (n=3). ***, $p<0.001$.

FIG. 9A shows the structure of pomolic acid. FIG. 9B shows the structure of tormentic acid. FIG. 9C shows pomolic acid and tormentic acid inhibited SENP1 activity in vitro. Recombinant His-JAK2 was SUMOylated followed by incubation with recombinant GST-SENP1 together with pomolic acid or tormentic acid for 3 hours. FIG. 9D shows the synergistic effects of cisplatin and echinocyslic acid, corosolicin acid, pomolic acid or tormentic acid in SKOV3 CR cells. FIG. 9E shows $IC_{50}$s of cisplatin in each combination in FIG. 9D where indicated. Data were represented as mean±SD (n=3).

FIGS. 11A and 11B show Mc (FIG. 11A) and UA (FIG. 11B) inhibited SENP1 activity in vivo. IGROV1 cells were incubated with Mc or UA for 48 hours and harvested for Western blot for indicated proteins. FIG. 11C shows quantification of SENP1 inhibition by Mc and UA in vivo. Intensity of SUMOylated JAK2 in B was measured by Quantity One software. FIGS. 11D and 11E show Mc (FIG. 11D) and UA (FIG. 11E) inhibited SENP1 activity in vitro. Recombinant His-JAK2 was SUMOylated as in FIG. 2F, followed by incubation with recombinant GST-SENP1 together with Mc or UA for 3 hours (h). FIG. 11F shows quantification of SENP1 inhibition by Mc and UA in vitro. Intensity of SUMOylated JAK2 was measured by Quantity One software. FIG. 11G shows a cellular thermal shift assay used to examine interactions of UA with SENP1. SENP1 stability was analyzed using Western blot against SENP1 antibody in IGROV1 cells. FIG. 11H shows quantification of non-denatured SENP1 fraction shown in FIG. 11G. FIG. 11I shows a cell free thermal shift assay used to examine interactions of UA with SENP1. SENP1 stability was analyzed by using Western blot against SENP1 antibody. FIG. 11J shows quantification of non-denatured SENP1 fraction shown in FIG. 11I. FIG. 11K shows a docked structure of SENP1 (PDB ID: 21Y0):UA complex. Green: UA; Salmon: interface. Right panel, active residues of SENP1 for SENP1:UA complex. Green: UA; Salmon: active residues. FIG. 11L shows an in vitro thermal shift assay used to analyze the interactions of UA and Mc with GST-SENP1-C603A. Stability of SENP1-C603A was analyzed by using Western blot against SENP1 antibody FIG. 12A shows the synergistic effects of cisplatin and UA in IGROV1 CR cells. Concentrations of cisplatin and UA as well as the CI index were indicated. Data were represented as mean±SD (n=3). FIG. 12B shows a photograph of tumors from IGROV1 CR xenograft mice treated with control, cisplatin (8 mg/kg/2 day intraperitoneally), UA (10 mg/kg/2 days), and UA+cisplatin (10 mg/kg/2 day of UA +8 mg/kg/2 day). FIG. 12C shows IGROV1 CR xenograft tumor growth curve by indicated treatments. Data are represented as means±SD, n=6 tumors/group. , p<0.01, , p<0.0001. FIG. 12**D shows body weight changes of mice in each group. Data are represented as means±SD, n=6 tumors/group.

FIGS. 13A-13Y depict images illustrating representative images of H&E (hematoxylin and eosin) and IHC (immunohistochemistry) staining of tissues sections. FIGS. 13A-13T show H&E staining of paraffin-embedded 3-μm-thick tissue sections of the tumor (FIGS. 13Q-13T), heart (FIGS. 13A-13D), lung (FIGS. 13M-13P), liver (FIGS. 13E-13H), and kidney (FIGS. 13I-13L) from IGROV1 CR xenograft mice. FIGS. 13U-13X show IHC staining against pSTAT3 and Bcl-xL antibodies of tumor samples from 4 groups of mice (magnification, ×200). FIG. 13Y shows quantification of pSTAT3 IHC score in tumor samples from mice treated with indicated drugs. ***, p<0.001.

FIG. 15A shows cell viability in response to UAMMC1, UAMMC2, UAMMC3, UAMMC4, UAMMC5, UAMMC6, UAMMC7 and UAMMC9. UAMMC concentration: 150 nM. Cell lines: IGROV1 CR cells. FIG. 15O shows quantification of pSTAT3 (Tyr705) levels in FIG. 15N.

DETAILED DESCRIPTION

Figure 1:
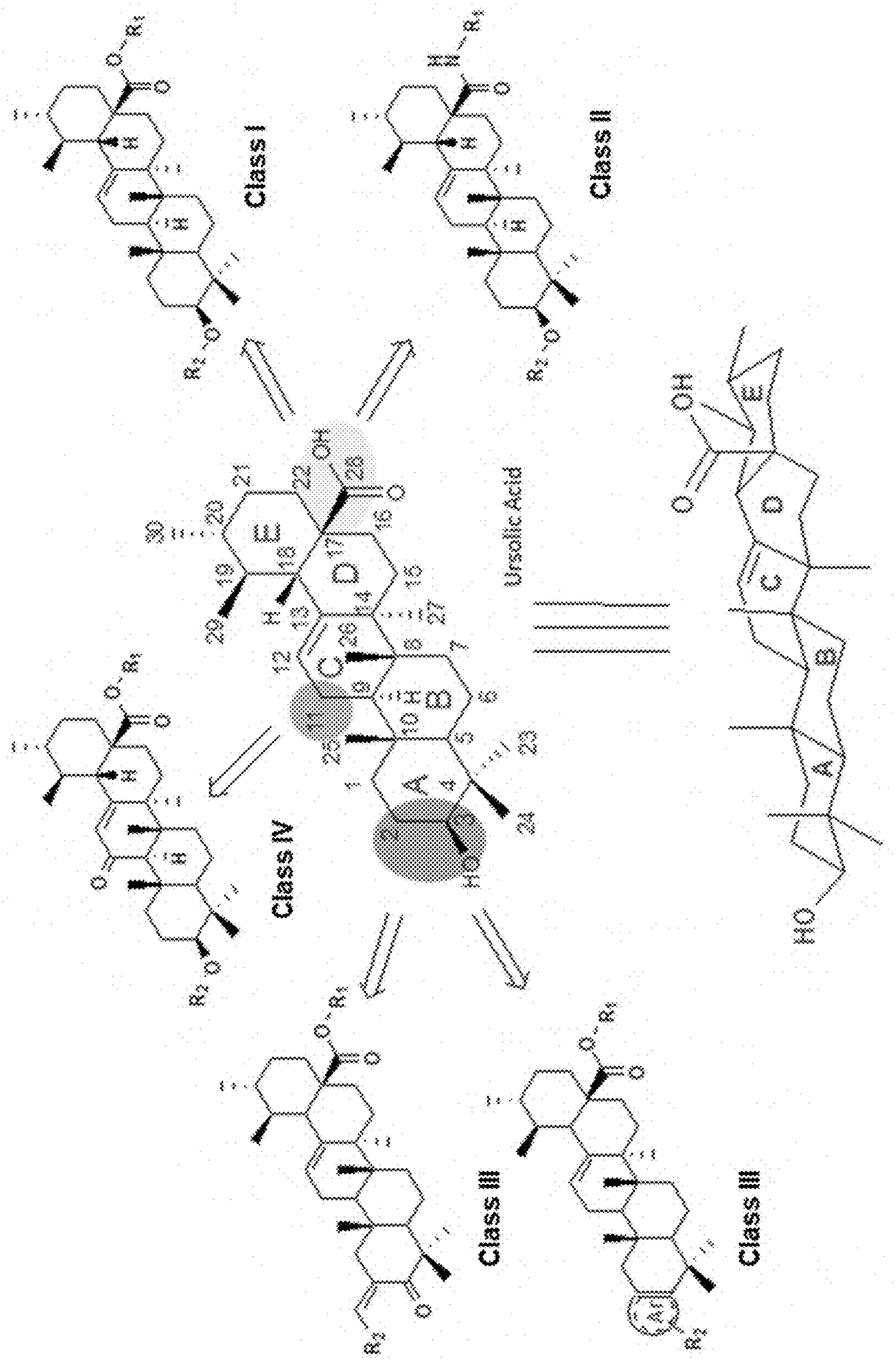
FIG. 1 depicts a schematic of methods of the present disclosure used for design of ursolic acid derivatives.

In the following sections, certain exemplary compositions and methods are described in order to detail certain embodiments of the invention. It will be obvious to one skilled in the art that practicing the certain embodiments does not require the employment of all or even some of the specific details outlined herein, but rather that concentrations, times and other specific details can be modified through routine experimentation. In some cases, well known methods, or components have not been included in the description.

Embodiments of the instant disclosure relate to novel methods and compositions for treating tumors resistant to or suspected of becoming resistant to platinum-based chemotherapy. In some embodiments, a tumor subjected to the methods and compositions disclosed herein can be a solid tumor. In some embodiments disclosed herein, compositions and methods disclosed herein are designed to re-sensitize or sensitize a tumor in a subject to platinum-based chemotherapy to reduce costs, improve outcome and reduce or eliminate patient exposure to platinum-based therapy without significant effect.

I. Ursolic Acid Derivatives

The present disclosure is based, at least in part, on the discovery of new ursolic acid derivatives and their use as anti-cancer agents. In certain embodiments, compositions and methods herein can include one or more ursolic acid derivatives as disclosed herein. In some embodiments, a ursolic acid derivative herein can be a compound represented by formula I or a pharmaceutically acceptable salt thereof:

(I)

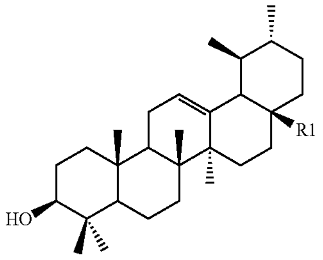

wherein R1 is selected from the group consisting of hydrogen, hydroxyl, hydroxymethyl, formyl, or

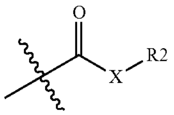

wherein X is or O or S, and $R_2$ is hydrogen, unsubstituted or substituted $C_1$-$C_6$ alkyl. As used herein, "substituted" means that the hydrogen on the group is substituted with one or more substituents selected from the group consisting of hydroxyl, halogen, $C_1$-$C_6$ alkyl, $C_1$-$C_6$ alkoxy, and carboxyl (—COOH).

As used herein, an alkyl is an aliphatic alkyl, which may be a linear or branched alkyl, and includes but is not limited to: methyl, ethyl, n-propyl, isopropyl, n-butyl, isobutyi, tert-butyl, etc. The expressions of the form "C1-C8" are intended to include those corresponding groups having 1, 2, 3, 4, 5, 6, 7, or 8 carbon atoms, for example, "$C_1$-$C_8$ alkyl" refers to an alkyl having 1, 2, 3, 4, 5, 6, 7 or 8 carbon atoms.

As used herein, alkoxy refers to —O (alkyl), wherein alkyl is as defined above. "$C_{1-6}$ alkoxy" refers to an alkyloxy group containing 1 to 6 carbons. Non-limiting examples include methoxy, ethoxy, propoxy, butoxy, and the like.

As used herein, halogen preferably refers to fluorine, chlorine, bromine or iodine.

Unless otherwise specified, the structure formula described herein are intended to include all tautomeric, optical, and stereoisomeric forms (e.g., enantiomers, diastereomers, geometric isomers, or conformers). For example, R and S configurations containing asymmetric centers, (Z), (E) isomers of double bonds and conformational isomers of (Z), (E). The individual stereochemical isomers, tautomers or enantiomers, diastereomers or geometric isomers or tautomers, or a mixture of conformers of the compounds of the invention belong to the scope of the present invention.

The term "tautomers" as used herein means that structural isomers with different energies can exceed low energy barriers and thus be converted into each other. For example, proton tautomers (i.e., proton shifts) include interconversions via proton migration, such as 1H-indazole and 2H-indazole, 1H-benzo[d]imidazole and 3H-benzo[d]imidazole. The valence tautomers include interconversions by reorganization of some bonding electrons.

The pharmaceutically acceptable salts for use herein are not particularly limited, and preferably include: inorganic acid salts, organic acid salts, alkyl sulfonates, and aryl sulfonates; the inorganic acid salts include hydrochloride hydrobromide, nitrate, sulfate, phosphate, etc.; the organic acid salts include formate, acetate, propionate, benzoate, maleate, fumarate, succinate, tartrate, citrate, etc.; the alkyl sulfonates include methyl sulfonate, ethyl sulfonate, etc.; and the aryl sulfonates include benzenesulfonate, p-toluenesulfonate, and the like.

In some embodiments, a ursolic acid derivative herein can be a compound represented by formula I or a pharmaceutically acceptable salt thereof:

(II)

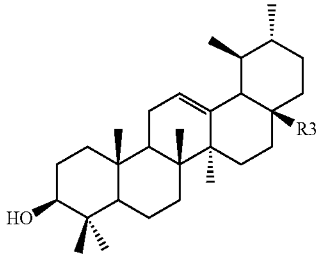

wherein R3 is selected from the group consisting of

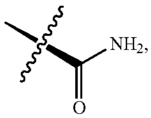
,
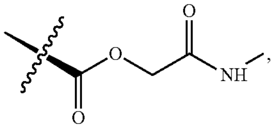
,

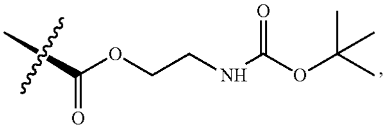
,

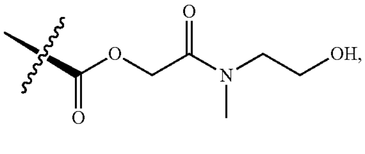
,

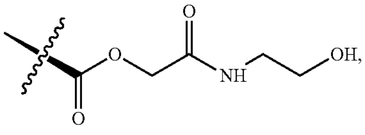
,

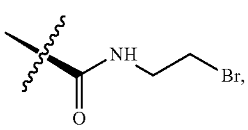
,
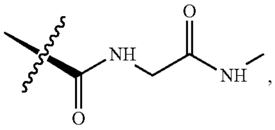
,

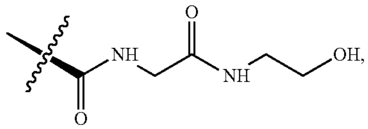
, or

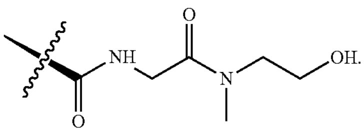
.

In some embodiments, a ursolic acid derivative herein can be

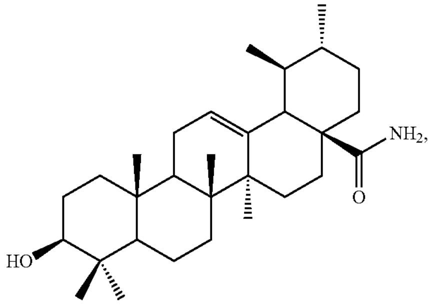

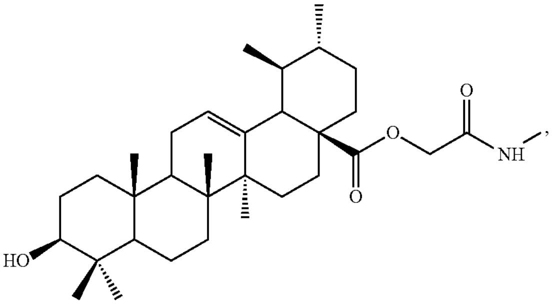

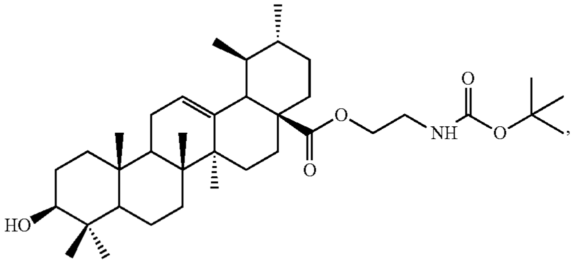

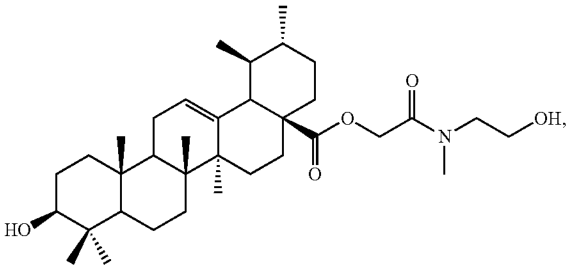

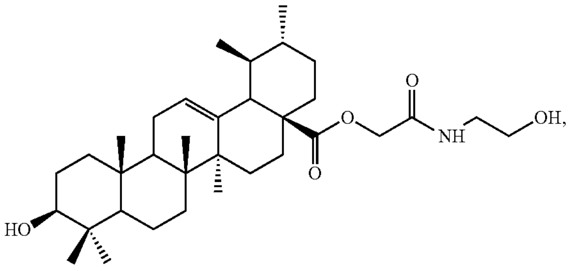

-continued

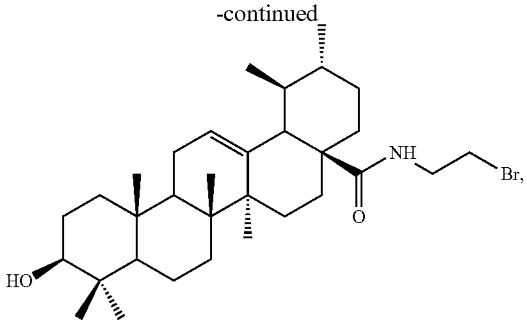

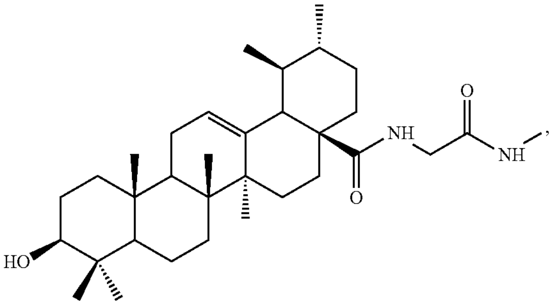

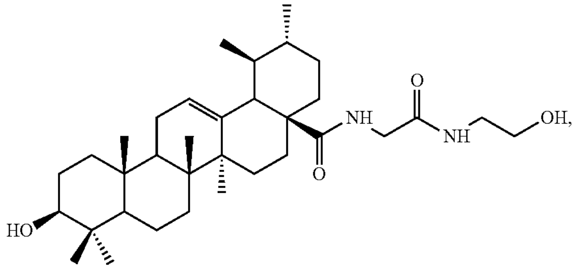

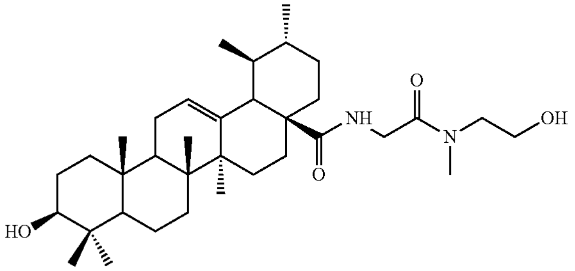

or a pharmaceutically acceptable salt thereof:

The present disclosure also provides embodiments for methods of making any one of the ursolic acid derivatives of pharmaceutically acceptable salt thereof as disclosed herein. Methods of making ursolic acid derivatives of the present disclosure are further described below with reference to specific examples (e.g. Example 1 herein). It should be understood that these examples are only used to illustrate the present invention and not to limit the scope of the present disclosure.

II. Pharmaceutical Compositions

In some embodiments, ursolic acid derivatives disclosed herein for use according to the methods herein described may be provided per se or as part of a pharmaceutical composition, where ursolic acid derivatives can be mixed with suitable carriers or excipients. In other embodiments, compositions disclosed herein include one or more ursolic acid derivatives herein and/or one or more platinum-based chemotherapeutics. In certain embodiments, these agents can be combined with a pharmaceutically acceptable carrier (excipient) to form a pharmaceutical composition for use in treating the tumor in a subject.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism. Herein the term "active ingredient" refers to one ore more of the ursolic acid derivatives disclosed herein, one or more platinum-based chemotherapeutics or a combination thereof.

(i) Pharmaceutically Acceptable Carriers and Excipients

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

In various embodiments, compositions disclosed herein may further compromise one or more pharmaceutically acceptable diluent(s), excipient(s), or carrier(s). As used herein, a pharmaceutically acceptable diluent, excipient, or carrier, refers to a material suitable for administration to a subject without causing undesirable biological effects or interacting in a deleterious manner with any of the components of the composition in which it is contained. Pharmaceutically acceptable diluents, carriers, and excipients can include, but are not limited to, physiological saline, Ringer's solution, phosphate solution or buffer, buffered saline, and other carriers known in the art. Pharmaceutical compositions may also include stabilizers, anti-oxidants, colorants, other medicinal or pharmaceutical agents, carriers, adjuvants, preserving agents, stabilizing agents, wetting agents, emulsifying agents, solution promoters, salts, solubilizers, antifoaming agents, antioxidants, dispersing agents, surfactants, and combinations thereof. Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols. Techniques for formulation and administration of drugs may be found in "Remington's Pharmaceutical Sciences," Mack Publishing Co., Easton, Pa., latest edition, which is incorporated herein by reference.

In various embodiments, pharmaceutical compositions described herein may be formulated in conventional manner using one or more physiologically acceptable carriers comprising excipients and auxiliaries to facilitate processing of genetically modified endothelial progenitor cells into preparations which can be used pharmaceutically. In other embodiments, any of the well-known techniques, carriers, and excipients may be used as suitable and as understood in the art.

In various embodiments, pharmaceutical compositions described herein may be an aqueous suspension comprising one or more polymers as suspending agents. In some aspects, polymers that may comprise pharmaceutical compositions described herein include: water-soluble polymers such as cellulosic polymers, e.g., hydroxypropyl methylcellulose; water-insoluble polymers such as cross-linked carboxyl-containing polymers; mucoadhesive polymers, selected from, for example, carboxymethylcellulose, carbomer (acrylic acid polymer), poly(methylmethacrylate), polyacrylamide, polycarbophil, acrylic acid/butyl acrylate copolymer, sodium alginate, and dextran; or a combination thereof. In other aspects, compositions disclosed herein may comprise at least 5%, at least 10%, at least 20%, at least 25%, at least 30%, at least 35%, at least 40%, at least 45%, at least 50% total amount of polymers as suspending agent (s) by total weight of the composition.

In various embodiments, pharmaceutical compositions disclosed herein may comprise a viscous formulation. In some aspects, viscosity of the composition may be increased by the addition of one or more gelling or thickening agents. In other aspects, compositions disclosed herein may comprise one or more gelling or thickening agents in an amount to provide a sufficiently viscous formulation to remain on treated tissue. In still other aspects, compositions disclosed herein may comprise at least 5%, at least 10%, at least 20%, at least 25%, at least 30%, at least 35%, at least 40%, at least 45%, at least 50% total amount of gelling or thickening agent(s) by total weight of the composition. In yet other aspects, suitable thickening agents can be hydroxypropyl methylcellulose, hydroxyethyl cellulose, polyvinylpyrrolidone, carboxymethyl cellulose, polyvinyl alcohol, sodium chondroitin sulfate, sodium hyaluronate. In other aspects, viscosity enhancing agents can be acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethylcellulose (CMC), silicon dioxide, polyvinylpyrrolidone (PVP: povidone), Splenda® (dextrose, maltodextrin and sucralose), or combinations thereof. In some embodiments, suitable thickening agent may be carboxymethylcellulose.

In various embodiments, pharmaceutical compositions disclosed herein may comprise additional agents or additives selected from a group including surface-active agents, detergents, solvents, acidifying agents, alkalizing agents, buffering agents, tonicity modifying agents, ionic additives effective to increase the ionic strength of the solution, antimicrobial agents, antibiotic agents, antifungal agents, antioxidants, preservatives, electrolytes, antifoaming agents, oils, stabilizers, enhancing agents, and the like. In some aspects, pharmaceutical compositions disclosed herein may comprise at least 5%, at least 10%, at least 20%, at least 25%, at least 30%, at least 35%, at least 40%, at least 45%, at least 50% total amount of one or more agents by total weight of the composition. In other aspects, one or more of these agents may be added to improve the performance, efficacy, safety, shelf-life and/or other property of the muscarinic antagonist composition of the present disclosure. In s aspects, additives will be biocompatible, and will not be harsh, abrasive, or allergenic.

In various embodiments, pharmaceutical compositions disclosed herein may comprise one or more acidifying agents. As used herein, "acidifying agents" refers to compounds used to provide an acidic medium. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art. In some aspects, any pharmaceutically acceptable organic or inorganic acid may be used. In other aspects, compositions disclosed herein may comprise at least 5%, at least 10%, at least 20%, at least 25%, at least 30%, at least 35%, at least 40%, at least 45%, at least 50% total amount of one or more acidifying agents by total weight of the composition.

In various embodiments, pharmaceutical compositions disclosed herein may comprise one or more alkalizing agents. As used herein, "alkalizing agents" are compounds used to provide alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art. In some aspects, any pharmaceutically acceptable organic or inorganic base can be used. In other aspects, compositions disclosed herein may comprise at least 5%, at least 10%, at least 20%, at least 25%, at least 30%, at least 35%, at least 40%, at least 45%, at least 50% total amount of one or more alkalizing agents by total weight of the composition.

In various embodiments, pharmaceutical compositions disclosed herein may comprise one or more antioxidants. As used herein, "antioxidants" are agents that inhibit oxidation and thus can be used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art. In some aspects, compositions disclosed herein may comprise at least 5%, at least 10%, at least 20%, at least 25%, at least 30%, at least 35%, at least 40%, at least 45%, at least 50% total amount of one or more antioxidants by total weight of the composition.

In other embodiments, pharmaceutical compositions disclosed herein may comprise a buffer system. As used herein, a "buffer system" is a composition comprised of one or more buffering agents wherein "buffering agents" are compounds used to resist change in pH upon dilution or addition of acid or alkali. Buffering agents include, by way of example and without limitation, potassium metaphosphate, potassium phosphate, monobasic sodium acetate and sodium citrate anhydrous and dihydrate and other materials known to one of ordinary skill in the art. In some aspects, any pharmaceutically acceptable organic or inorganic buffer can be used. In another aspect, compositions disclosed herein may comprise at least 5%, at least 10%, at least 20%, at least 25%, at least 30%, at least 35%, at least 40%, at least 45%, at least 50% total amount of one or more buffering agents by total weight of the composition. In other aspects, the amount of one or more buffering agents may depend on the desired pH level of a composition. In some embodiments, pharmaceutical compositions disclosed herein may have a pH of about 6 to about 9. In other embodiments, pharmaceutical compositions disclosed herein may have a pH greater than about 8, greater than about 7.5, greater than about 7, greater than about 6.5, or greater than about 6. In a preferred embodiment, compositions disclosed herein may have a pH greater than about 6.8.

In various embodiments, pharmaceutical compositions disclosed herein may comprise one or more preservatives. As used herein, "preservatives" refers to agents or combination of agents that inhibits, reduces or eliminates bacterial growth in a pharmaceutical dosage form. Non-limiting examples of preservatives include Nipagin, Nipasol, isopropyl alcohol and a combination thereof. In some aspects, any pharmaceutically acceptable preservative can be used. In other aspects, pharmaceutical compositions disclosed herein may comprise at least 5%, at least 10%, at least 20%, at least 25%, at least 30%, at least 35%, at least 40%, at least 45%, at least 50% total amount of one or more preservatives by total weight of the composition.

In other embodiments, pharmaceutical compositions disclosed herein may comprise one or more surface-acting reagents or detergents. In some aspects, surface-acting reagents or detergents may be synthetic, natural, or semi-synthetic. In other aspects, compositions disclosed herein may comprise anionic detergents, cationic detergents, zwitterionic detergents, ampholytic detergents, amphoteric detergents, nonionic detergents having a steroid skeleton, or a combination thereof. In still other aspects, pharmaceutical compositions disclosed herein may comprise at least 5%, at least 10%, at least 20%, at least 25%, at least 30%, at least 35%, at least 40%, at least 45%, at least 50% total amount of one or more surface-acting reagents or detergents by total weight of the composition.

In various embodiments, pharmaceutical compositions disclosed herein may comprise one or more stabilizers. As used herein, a "stabilizer" refers to a compound used to stabilize an active agent against physical, chemical, or biochemical process that would otherwise reduce the therapeutic activity of the agent. Suitable stabilizers include, by way of example and without limitation, succinic anhydride, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art. In some aspects, pharmaceutical compositions disclosed herein may comprise at least 5%, at least 10%, at least 20%, at least 25%, at least 30%, at least 35%, at least 40%, at least 45%, at least 50% total amount of one or more stabilizers by total weight of the composition.

In other embodiments, pharmaceutical compositions disclosed herein may comprise one or more tonicity agents. As used herein, a "tonicity agents" refers to a compound that can be used to adjust the tonicity of the liquid formulation. Suitable tonicity agents include, but are not limited to, glycerin, lactose, mannitol, dextrose, sodium chloride, sodium sulfate, sorbitol, trehalose and others known to those or ordinary skill in the art. Osmolarity in a composition may be expressed in milliosmoles per liter (mOsm/L). Osmolarity may be measured using methods commonly known in the art. In preferred embodiments, a vapor pressure depression method is used to calculate the osmolarity of the compositions disclosed herein. In some aspects, the amount of one or more tonicity agents comprising a pharmaceutical composition disclosed herein may result in a composition osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L. In other aspects, a composition herein may have an osmolality ranging from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/ kg to about 320 mOsm/kg. In some embodiments, a pharmaceutical composition described herein has an osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L. In still other aspects, pharmaceutical compositions disclosed herein may comprise at least 5%, at least 10%, at least 20%, at least 25%, at least 30%, at least 35%, at least 40%, at least 45%, at least 50% total amount of one or more tonicity modifiers by total weight of the composition.

(ii) Dosage Formulations

Suitable routes of administration may, for example, include oral, rectal, transmucosal, especially transnasal, intestinal or parenteral delivery, including intramuscular, subcutaneous and intramedullary injections as well as, intravenous, intraperitoneal, intranasal injections.

One may administer the pharmaceutical composition in a local or systemic manner, for example, via local injection of the pharmaceutical composition directly into a tissue region of a patient. In some embodiments, a pharmaceutical composition disclosed herein can be administered parenterally, e.g., by intravenous injection, intracerebroventricular injection, intra-cisterna magna injection, intra-parenchymal injection, or a combination thereof. In some embodiments, a pharmaceutical composition disclosed herein can administered to the human patient via at least two administration routes. In some examples, the combination of administration routes by be intracerebroventricular injection and intravenous injection; intrathecal injection and intravenous injection; intra-cisterna magna injection and intravenous injection; and intra-parenchymal injection and intravenous injection.

Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present disclosure thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

Pharmaceutical compositions suitable for use in context of the present disclosure include compositions wherein the active ingredients are contained in an amount effective to achieve the intended purpose. In some embodiments, a therapeutically effective amount means an amount of active ingredients (e.g., ursolic acid derivatives disclosed herein) effective to prevent, slow, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the present disclosure, the therapeutically effective amount or dose can be estimated initially from in vitro and cell culture assays and or screening platforms disclosed herein. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to brain or blood levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc. Effective doses may be extrapolated from dose-responsive curves derived from in vitro or in vivo test systems.

III. Methods of Use

Embodiments of the instant disclosure relate to novel methods and compositions for treating tumors resistant to or suspected of becoming resistant to platinum-based chemotherapy. In some embodiments, a tumor subjected to the methods and compositions disclosed herein can be a solid tumor. In some embodiments disclosed herein, compositions and methods disclosed herein are designed to re-sensitize or sensitize a tumor in a subject to platinum-based chemotherapy to reduce costs, improve outcome and reduce or eliminate patient exposure to platinum-based therapy without significant effect.

In some embodiments, a subject can have a platinum-based chemotherapy resistant tumor or be suspected of developing such a tumor where additional agents can be administered to re-sensitize or sensitize a tumor in a subject where the tumor includes a solid tumor. In some embodiments, a solid tumor can be an abnormal mass of tissue that is devoid of cysts or liquid regions within the tumor. In some embodiments, solid tumors can be benign (not progressed to a cancer), a malignant or metastatic tumor. In some embodiments, a solid tumor herein can be a malignant cancer that has metastasized. In other embodiments, solid tumors contemplated herein can include, but are not limited to, sarcomas, carcinomas, lymphomas, gliomas or a combinational thereof. In accordance with some embodiments herein, tumors resistant to platinum-based chemotherapy can include, but are not limited to, a testicular tumor, ovarian tumor, cervical tumor, a kidney tumor, bladder tumor, head-and-neck tumor, liver tumor, stomach tumor, lung tumor, endometrial tumor, esophageal tumor, breast tumor, cervical tumor, central nervous system tumor, germ cell tumor, prostate tumor, Hodgkin's lymphoma, non-Hodgkin's lymphoma, neuroblastoma, sarcoma, multiple myeloma, melanoma, mesothelioma, osteogenic sarcoma or a combination thereof. In some embodiments, a targeted tumor contemplated herein can include a solid tumor such as ovarian tumors.

Some standards of care for solid tumors include combination therapies but there has been limited success with combination therapies. Such combinations can lead to toxicity of the drugs, significant number of patients that are ineligible for cisplatin-based therapies, and a relatively small therapeutic survival benefit of about 5-15% when these combinations are used. Embodiments disclosed herein are designed to avoid such outcomes as there is a need in the art for new combination therapies that are equally or more effective than the current standard of care, and that offer patients a much more tolerable chemotherapeutic regimen.

Studies have been performed and are currently continuing to identify biomarkers of chemotherapeutically-resistant cancers such as platinum-resistant cancers. Therapeutically actionable targets in platinum-resistant tumors have been hampered for example, by reliance on using simplistic techniques with tumor-derived cell line models. Embodiments of the instant inventions are based, at least in part, on the identification of genes and pathways critical for chemoresistance in cancer as identified through multi-omic molecular profiling, coupled with whole genome CRISPR screening under treatment. Using these methods of advanced profiling, the present disclosure provides in certain embodiments disclosed herein methods and compositions for treating tumors resistant to platinum-based chemotherapy by, for example, identifying a subject having tumors with increased expression of SENP1 and/or administering an effective amount of at least one ursolic acid derivative disclosed herein in combination with at least one platinum-based chemotherapeutic to the subject for treating a solid tumor whether or not identified as a SENP1 overexpresser.

In some embodiments, compositions of use herein can include one or more ursolic acid derivatives or salts thereof. In some embodiments, concentrations of ursolic acid derivatives or salts thereof for use in therapies disclosed herein can include about 1 mg to about 200 mg, about 5 mg to about 150 mg, about 10 mg to about 120 mg, about 20 mg about 30 mg, about 40 mg, about 60 mg, about 80 mg, about 100 mg, about 120 mg, about 140 mg, about 160 mg, about 180 mg, about 200 mg. In certain embodiments, ursolic acid derivatives or salts thereof can be administered to a subject alone or in combination with a chemotherapeutic agent, daily, every other day, twice weekly, every other day, every other week, weekly or monthly or other suitable dosing regimen.

In some embodiments, other compositions which can be administered alone or in combination with an ursolic acid derivative-containing compositions can include a platinum-based chemotherapeutic. As used herein, a "platinum-based chemotherapeutic" is a chemotherapeutic that is an organic compound which contains platinum as an integral part of the molecule. In some embodiments, compositions of use herein can contain one or more platinum-based chemotherapeutics including, but not limited to, cisplatin, carboplatin, nedaplatin, triplatin tetranitrate, phenanthriplatin, picoplatin, satraplatin or a combination thereof. In some embodiments, a platinum-based chemotherapeutic can be administered separately from an ursolic acid derivative or a derivative thereof. In some embodiments, compositions containing a platinum-based chemotherapeutic of use herein can contain a concentration of the platinum-based chemotherapeutic at about 1 mg/ml to about 100 mg/ml (e.g., about 1 mg/ml, about 5 mg/ml, about 10 mg/ml, about 20 mg/ml, about 30 mg/ml, about 40 mg/ml, about 50 mg/ml, about 60 mg/ml, about 80 mg/ml, about 100 mg/ml). In some embodiments, the platinum-based chemotherapeutic or salt thereof or derivative thereof includes cisplatin. In certain embodiments, platinum-based chemotherapeutic agents can be administered to a subject alone or in combination with at least one ursolic acid derivative, daily, every other day, twice weekly, every other day, every other week, weekly or monthly or other suitable dosing regimen.

In certain embodiments, compositions disclosed herein can treat and/or prevent cancer in a subject in need. In some embodiments, compositions disclosed herein can impair tumor growth compared to tumor growth in an untreated subject with identical disease condition and predicted outcome. In some embodiments, tumor growth can be stopped following treatment with compositions disclosed herein. In other embodiments, tumor growth can be impaired at least about 5% or greater to at least about 100%, at least about 10% or greater to at least about 95% or greater, at least about 20% or greater to at least about 80% or greater, at least about 40% or greater to at least about 60% or greater compared to an untreated subject with identical disease condition and predicted outcome. In other words, tumors in subject treated using a composition of the disclosure have tumors that grow at least 5% less (or more as described above) when compared to an untreated subject with identical disease condition and predicted outcome. In some embodiments, tumor growth can be impaired at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome. In some embodiments, tumor growth can be impaired at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated subject with identical disease condition and predicted outcome.

In some embodiments, treatment of tumors with compositions disclosed herein can result in a shrinking of a tumor in comparison to the starting size of the tumor. In some embodiments, tumor shrinking is at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% (meaning that the tumor is completely gone after treatment) compared to the starting size of the tumor.

In various embodiments, compositions disclosed herein can improve patient life expectancy compared to the cancer life expectancy of an untreated subject with identical disease condition and predicted outcome. As used herein, "patient life expectancy" is defined as the time at which 50 percent of subjects are alive and 50 percent have passed away. In some embodiments, patient life expectancy can be indefinite following treatment with a composition disclosed herein. In other aspects, patient life expectancy can be increased at least about 5% or greater to at least about 100%, at least about 10% or greater to at least about 95% or greater, at least about 20% or greater to at least about 80% or greater, at least about 40% or greater to at least about 60% or greater compared to an untreated subject with identical disease condition and predicted outcome. In some embodiments, patient life expectancy can be increased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome. In some embodiments, patient life expectancy can be increased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with identical disease condition and predicted outcome.

In some embodiments, the methods of the present disclosure increase anti-tumor activity (e.g., reduce cell proliferation, tumor growth, tumor volume, and/or tumor burden or load or reduce the number of metastatic lesions over time) by at least about 10%, 20%, 25%, 30%, 40%, 50%, 60%, 70%, 75%, 80%, 85%, 90%, 95%, or more as compared to levels prior to treatment or in a control subject. In some embodiments, reduction is measured by comparing cell proliferation, tumor growth, and/or tumor volume in a subject before and after administration of the pharmaceutical composition. In some embodiments, the method of treating or ameliorating a cancer in a subject allows one or more symptoms of the cancer to improve by at least about 10%, 20%, 30%, 40%, 50%, 60%, 70%, 80%, 90%, 95%, or more. In some embodiments, before, during, and after the administration of the pharmaceutical composition, cancerous cells and/or biomarkers in a subject are measured in a biological sample, such as blood, serum, plasma, urine, peritoneal fluid, and/or a biopsy from a tissue or organ. In some embodiments, the methods include administration of the compositions of the invention to reduce tumor volume, size, load or burden in a subject to an undetectable size, or to less than about 1%, 2%, 5%, 10%, 20%, 25%, 30%, 40%, 50%, 60%, 70%, 75%, 80%, or 90% of the subject's tumor volume, size, load or burden prior to treatment. In other embodiments, the methods include administration of the compositions of the invention to reduce the cell proliferation rate or tumor growth rate in a subject to an undetectable rate, or to less than about 1%, 2%, 5%, 10%, 20%, 25%, 30%, 40%, 50%, 60%, 70%, 75%, 80%, or 90% of the rate prior to treatment.

In some embodiments, a subject to be treated by any of the methods and/or compositions herein can present with one or more cancerous solid tumors, metastatic nodes, of a combination thereof. In some embodiments, a subject herein can have a cancerous tumor cell source that can be less than about 0.2 $cm^3$ to at least about 20 $cm^3$ or greater, at least about 2 $cm^3$ to at least about 18 $cm^3$ or greater, at least about 3 $cm^3$ to at least about 15 $cm^3$ or greater, at least about 4 $cm^3$ to at least about 12 $cm^3$ or greater, at least about 5 $cm^3$ to at least about 10 $cm^3$ or greater, or at least about 6 $cm^3$ to at least about 8 $cm^3$ or greater.

In various embodiments, the compositions disclosed herein can be effective for treating at least one tumor cell in a solid tumor from a subject in need. In some embodiments, the amount of viable tumor cells is reduced by at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome.

In various embodiments, the compositions disclosed herein can reduce the amount of viable tumor cells by at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome.

Conventional methods, known to those of ordinary skill in the art of medicine, can be used to administer the compositions disclosed herein to a subject, depending upon the type of disease to be treated or the site of the disease. In some embodiments, compositions herein can be administered to a subject by intravenous infusion by subcutaneous administration, by inhalation, by intranasal administration or other mode of administration. In some embodiments, compositions herein can be administered to a subject orally.

In some embodiments, any of the methods disclosed herein can further include monitoring occurrence of one or more adverse effects in the subject. Exemplary adverse effects include, but are not limited to, hepatic impairment, hematologic toxicity, neurologic toxicity, cutaneous toxicity, gastrointestinal toxicity, or a combination thereof. When one or more adverse effects are observed, the method disclosed herein can further include reducing or increasing the dose of the one or ursolic acid derivatives, the dose of one or more platinum-based chemotherapeutics or both depending on the adverse effect or effects in the subject. For example, when a moderate to severe hepatic impairment is observed in a subject after treatment, compositions of use to treat the subject can be reduced in concentration or frequency of dosing with one or more ursolic acid derivative, the dose or frequency of the platinum-based chemotherapeutic can be adjusted (e.g., cisplatin) or a combination thereof.

In some embodiments, one or more ursolic acid derivatives herein can be administered concurrently with the one or more platinum-based chemotherapeutic by the same or different modes of administration. In some embodiments, one or more ursolic acid derivatives herein can be administered before, during or after the one or more chemotherapeutics. In other embodiments, the one or more chemotherapeutics can be administered systemically. In certain embodiments, the one or more platinum-based chemotherapeutic can be administered locally directly to one or more tumors in the subject. In some embodiments, the one or more platinum-based chemotherapeutic can be administered by intravenous administration, e.g., as a bolus or by continuous infusion over a period of time, by intramuscular, intraperitoneal, intracerebrospinal, subcutaneous, intra-arterial, intra-articular, intrasynovial, intrathecal, intratumoral, oral, inhalation or topical routes. In other embodiments, the one or more platinum-based chemotherapeutic can be administered to the subject by intravenous infusion.

An effective amount of the pharmaceutical composition described herein can be administered to a subject (e.g., a human) in need of the treatment via a suitable route, systemically or locally. In some embodiments, the one or more ursolic acid derivatives herein can be administered by intravenous administration, e.g., as a bolus or by continuous infusion over a period of time, by intramuscular, intraperitoneal, intracerebrospinal, subcutaneous, intra-arterial, intra-articular, intrasynovial, intrathecal, intratumoral, oral, inhalation or topical routes. In some embodiments, the one or more ursolic acid derivatives herein can be administered orally.

In some embodiments, dosages for the one or more ursolic acid derivatives herein and/or one or more platinum-based chemotherapeutics as described herein are determined empirically in individuals who have been given one or more administration(s) of the one or more ursolic acid derivatives herein and/or one or more platinum-based chemotherapeutics. Individuals are given incremental dosages of the one or more ursolic acid derivatives herein and/or one or more platinum-based chemotherapeutics. To assess efficacy of the one or more ursolic acid derivatives herein and/or one or more platinum-based chemotherapeutics, an indicator of the disease/disorder can be followed.

In some embodiments, methods herein of treating a cancer with one or more ursolic acid derivatives herein and/or one or more platinum-based chemotherapeutics can further include treating a subject with at least one additional anti-cancer therapy, for example, chemotherapy, radiotherapy, immunotherapy, or surgery. In some embodiments, an additional anti-cancer therapy can be administered to the subject including, but not limited to, one or more of gemcitabine, methotrexate, vinblastine, and/or adriamycin. In some embodiments, methods herein can be administered to a subject who has completed at least one anti-cancer therapy or who is currently undergoing at least anti-cancer therapy. In some embodiments, methods herein can be administered to a subject having received and/or currently receiving at least one immune-modulatory agent. Non-limiting examples of such immune-modulatory agents include, but are not limited to, anti-PD1, anti-PD-L1, anti-CTLA-4, anti-OX40, anti-CD137, etc. Non-limiting examples of PD-1 inhibitors include, but are not limited to, anti-PD-1 antibodies, such as pembrolizumab, nivolumab, and cemiplimab. Non-limiting examples of PD-L1 inhibitors can include atezolizumab, durvalumab, and avelumab. A non-limiting example of a CTLA-4 inhibitor is the anti-CTLA-4 antibody ipilimumab. In some embodiments, an immunomodulatory agent can be one or more inhibitors that target a checkpoint molecule selected from CD40, GITR, LAG-3, OX40, TIGIT and TIM-3. In some embodiments, the additional one or more chemotherapeutics can include an antimetabolite, a microtubule inhibitor, or a combination thereof. Antimetabolites can include, for example, folic acid antagonist (e.g., methotrexate) and nucleotide analogs such as pyrimidine antagonist (e.g., 5-fluorouracil, foxuridine, cytarabine, capecitabine, and gemcitabine), purine antagonist (e.g., 6-mercaptopurine and 6-thioguanine), and adenosine deaminase inhibitor (e.g., cladribine, fludarabine and pentostatin).

In some embodiments, methods of treatment with at least one ursolic acid derivative herein and/or one or more platinum-based chemotherapeutic can depend on the cancer type, grade of cancer, stage or cancer or a combination thereof. In some embodiments, methods of treatment with at least one ursolic acid derivative herein and/or one or more platinum-based chemotherapeutic can depend on the stage of cancer as determined by the TNM system wherein "T" stands for tumor, "N" stands for node, and "M" stands for metastasis. When applying the TNM system, the following are considered: Tumor (T)—How large is the primary tumor? Where is it located?; Node (N)—Has the tumor spread to the lymph nodes? If so, where and how many?; and Metastasis (M)—Has the cancer spread to other parts of the body? If so, where and how much? In some embodiments, methods of treatment with at least one ursolic acid derivative herein and/or one or more platinum-based chemotherapeutic can depend on the stage of bladder cancer. One of skill in the art (i.e., a physician) can assign the stage of the cancer in a subject by combining the T, N, and M classifications.

In some embodiments, methods for the measuring SENP1 levels in a targeted tumor are disclosed where SENP1 can be used as at least one biomarker, for example, to select or identify patients or subjects in need of aminopeptidase adjustment. In certain embodiments, SENP1 levels can determine tumor burden, disease progression or projected response to treatment.

As used herein, "biomarker" can mean a distinctive biological or biologically derived indicator of a process, event or conditions. In some embodiments, the biomarker is a gene or gene product (e.g., a polypeptide). In some embodiments, a combination of biomarkers can be used as an indicator of a process, event or condition. In some embodiments, a combination of biomarkers used as an indicator of a process, event or condition can encompass at least two biomarkers. In some embodiments, a combination of biomarkers used as an indicator of a process, event or condition can encompass at least two biomarkers wherein one of the at least two biomarkers can be SENP1.

As used herein, "predictive biomarker" can refer to a biomarker that can be used in advance of therapy to estimate the likelihood or predictability of response to a given therapeutic agent or class of therapeutic agents. In some embodiments, a combination of predictive biomarkers can be used in advance of therapy to estimate the likelihood or predictability of response to a given therapeutic agent or class of therapeutic agents. In some embodiments, a combination of predictive biomarkers used in advance of therapy to estimate the likelihood or predictability of response to a given therapeutic agent or class of therapeutic agents can have at least two predictive biomarkers. In some embodiments, a combination of predictive biomarkers used in advance of therapy to estimate the likelihood or predictability of response to a given therapeutic agent or class of therapeutic agents can have at least one predictive biomarkers wherein one of the predictive biomarkers can be SENP1.

As used herein, the term "biological sample" can mean a sample obtained from a subject. A suitable biological sample can be obtained from a subject as described herein via routine practice. Non-limiting examples of biological samples include fluid samples such as blood (e.g., whole blood, plasma, or serum), urine, and saliva, and solid samples such as tissue (e.g., skin, lung, or nasal) and feces. Such samples can be collected using any method known in the art or described herein, e.g., buccal swab, nasal swab, venipuncture, biopsy, urine collection, or stool collection. In some embodiments, the biological sample can be a blood sample. In some other embodiments, the blood sample is a serum sample or a plasma sample. In some embodiments, a biological sample can be derived from a tissue and/or tumor biopsy collected from the subject e.g., patient-derived organotypic tumor spheroids prepared as described herein.

In some embodiments, methods herein of measuring SENP1 levels in a biological sample of subject can be measured by routine practice. Methods for detecting and/or assessing an amount of gene expression of SENP1 in a biological sample are well known in the art, and all suitable methods for detecting and/or assessing an amount of gene expression levels known to one of skill in the art are contemplated within the scope of the invention. In some embodiments, gene expression of SENP1 in a biological sample can be measured by high-density expression array, DNA microarray, polymerase chain reaction (PCR), reverse transcriptase PCR (RT-PCR), real-time quantitative reverse transcription PCR (qRT-PCR), digital droplet PCR (ddPCR), serial analysis of gene expression (SAGE), Spotted cDNA arrays, GeneChip, spotted oligo arrays, bead arrays, RNA Seq, tiling array, northern blotting, hybridization microarray, in situ hybridization, or a combination thereof. In some aspects, gene expression of SENP1 as disclosed herein can be measured by any known or future method suitable to assess gene expression.

Methods for detecting and/or assessing an amount of protein expression of SENP1 in a biological sample are well known in the art, and all suitable methods for detecting and/or assessing an amount of protein expression levels known to one of skill in the art are contemplated within the scope of the invention. In some embodiments, protein expression of SENP1 in a biological sample can be measured by Western blotting, enzyme-linked immunosorbent assay (ELISA), mass spectrometry, HPLC, flow cytometry, fluorescence-activated cell sorting (FACS), liquid chromatography-mass spectrometry (LC/MS), immunoelectrophoresis, translation complex profile sequencing (TCP-seq), protein microarray, protein chip, capture arrays, reverse phase protein microarray (RPPA), two-dimensional gel electrophoresis or (2D-PAGE), functional protein microarrays, electrospray ionization (ESI), matrix-assisted laser desorption/ionization (MALDI), or a combination thereof. In some aspects, protein expression of SENP1 as disclosed herein can be measured by any known or future method suitable to assess protein expression.

In some embodiments, a subject can be a human patient having an elevated level of SENP1 as relative to a control level. A control level can refer to the level of SENP1 in a matched sample of a subject of the same species (e.g., human) who are free of the solid tumor. In some examples, the control level represents the level of SENP1 in healthy subjects.

IV. Kits

In certain embodiments, the present disclosure provides kits for use in treating or alleviating a solid tumor described herein. Such kits can include one or more containers including one or more ursolic acid derivatives, e.g., any of those described. In some embodiments, kits can include one or more containers including one or more ursolic acid derivatives, e.g., any of those described and one or more platinum-based chemotherapeutic described herein (e.g., a cisplatin). In other embodiments, kits can include a control SENP1 sample for assessing level of SENP1 in a sample from a subject.

In some embodiments, the kits herein can include instructions for use in accordance with any of the methods described herein. The included instructions can have a description of administration of the ursolic acid derivatives disclosed herein, the one or more platinum-based chemotherapeutics, to treat, delay the onset, or alleviate a target disease as those described herein, or a combination thereof. In some embodiments, the kit can further include a description of selecting an individual suitable for treatment based on identifying whether that individual has the target disease, e.g., applying the diagnostic method as described herein. In still other embodiments, the instructions can have a description of administering any one of the compositions described herein to an individual at risk of the target disease.

In some embodiments, kit instructions relating to the use of one or more ursolic acid derivatives herein, one or more platinum-based chemotherapeutic described herein (e.g., a cisplatin), or a combination thereof can generally include information as to dosage, dosing schedule, and route of administration for the intended treatment. The containers can be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating the solid tumor. In some embodiments, instructions are provided for practicing any of the methods described herein. In some embodiments, instructions are provided for assessing SENP1 as a biomarker of disease (e.g., cancer).

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. In some embodiments, a kit has a sterile access port (for example the container can be an intravenous solution bag or a vial having a stopper pierceable by a hypodermic injection needle). In some embodiments, the container also has a sterile access port (for example the container is an intravenous solution bag or a vial having a stopper pierceable by a hypodermic injection needle). At least one active agent in the composition is at least one ursolic acid derivatives disclosed as those described herein.

In some embodiments, kits herein can optionally provide additional components such as buffers and interpretive information. Normally, the kit comprises a container and a label or package insert(s) on or associated with the container. In some embodiments, the invention provides articles of manufacture comprising contents of the kits described above.

EXAMPLES

The following examples are included to demonstrate preferred embodiments of the disclosure. It should be appreciated by those of skill in the art that the techniques disclosed in the examples that follow represent techniques discovered by the inventors to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Example 1. Design and Synthesis of Ursolic Acid Derivatives

Design of ursolic acid derivatives. As a pentacyclic triterpene natural product, ursolic acid consists of five rings, namely ring A-E, and contains 10 chiral carbon atoms (C-3, C-5, C-8, C-9, C-10, C-14, C-17, C-18, C-19, and C-20), one carboxyl (28-COOH), one hydroxyl (3-OH) and one double bond (12-Ene). Its three-dimensional structure shows a special spatial conformation. C-2, C-3, C-28, and C-11 in ursolic acid are potential modifiable sites, and most of the ursolic acid derivatives reported so far are derivatized at these sites. Four classes of ursolic acid derivatives were designed and synthesized by modification at the above sites. As shown in FIG. 1, the class I and II compounds were modified on the 28-carboxyl group of UA, which are ester derivatives and amide derivatives, respectively. The class III compounds were modified at C-2 and C-3 positions. After oxidation of 3-OH, the α-H atom at C-2 was activated, and 2-arylmethylene derivatives and aromatic heterocyclic derivatives were obtained. Class IV compounds were 11-oxo ursolic acid derivatives by oxidizing the C-11 allyl group.

Synthesis of Ursolic Acid Derivatives.

UAMMC1:

Synthesis of UA-I-1-2.

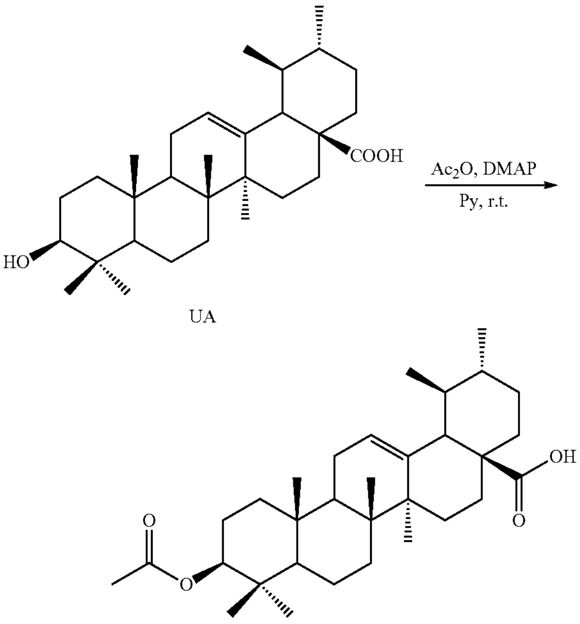

UA

UA-I-1-2

10 g (21.90 mmol, 1 eq) ursolic acid and 0.26 g DMAP (2.10 mmol, 0.1 eq) were dissolved in 150 mL anhydrous pyridine. The mixture was stirred at room temperature. 8.94 g acetic anhydride (87.58 mmol, 4 eq) was added dropwise, and the mixture was stirred overnight. Pyridine was evaporated under reduced pressure, and the residue was extracted with 150 mL water and 200 mL dichloromethane. The dichloromethane layer was washed again with 1N hydrochloric acid solution and dried with anhydrous $MgSO_4$. After the solvent was removed by vacuum steaming, 100 mL methanol was added to the residue and stirred for 0.5 h. 8.91 g of UA-I-1-2 was obtained by filtration as white solid with a yield of 81.6%. Melting point: 279.8-281.9° C.; ESI-MS m/z 497.53 $[M-H]^-$; $^1H$ NMR (400 MHz, DMSO-d6) δ 11.94 (s, 1H), 5.14 (s, 1H), 4.41 (dd, $J_1$=10.8 Hz, $J_2$=4.4 Hz, 1H), 2.12 (d, J=11.2 Hz, 1H), 2.01 (s, 3H), 1.99-1.90 (m, 1H), 1.89-1.74 (m, 3H), 1.68-1.41 (m, 10H), 1.39-1.22 (m, 4H), 1.06 (s, 3H), 1.01 (d, J=13.2 Hz, 2H), 0.92 (s, 6H), 0.84 (m, 10H), 0.76 (s, 3H).

Synthesis of UA-II-1-1.

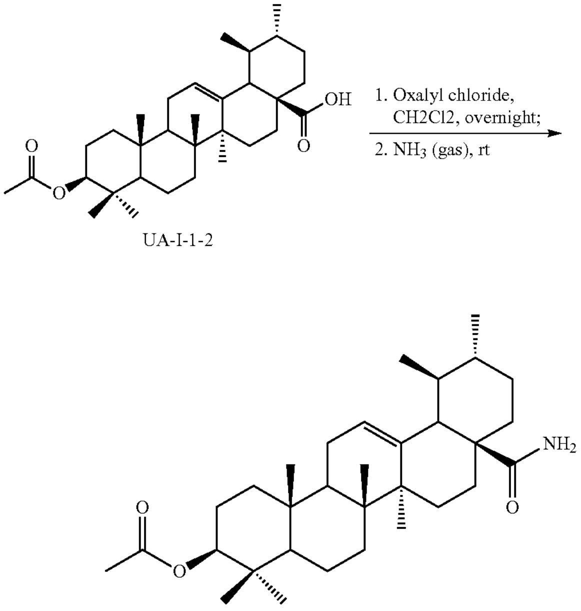

UA-I-1-2

UA-II-1-1

4.00 g UA-I-1-2 (8.01 mmol, 1 eq) was dissolved in 60 mL dichloromethane and stirred in an ice bath for 0.5 h. 3.05 g oxalyl chloride (24.03 mmol, 3 eq) was added to the mixture, then the ice bath was removed and reacted overnight at room temperature. The solvent was removed under reduced pressure, 25 mL dichloromethane, was added to the residue and evaporated again. Repeated the operation twice, the residue was dissolved with 40 mL dichloromethane and stirred at room temperature. The ammonia droplet was added to the sodium hydroxide solid, and the ammonia gas was dried by alkali lime and bubbled into the dichloromethane solution of the acyl chloride intermediate. The system gradually became turbid, and the tail gas was absorbed by a 6N hydrochloric acid solution. After the reaction was completed, the reaction solution is washed with distilled water and brine, and the organic layer was dried with anhydrous $MgSO_4$. After the solvent was removed under reduced pressure, the residue was separated on a silica gel column (PE:EA (V:V)=10:1-5:1). 2.84 g UA-II-1-1 was obtained as white powder with a yield of 71.3%. Melting point: 293.1-294.7° C. ESI-MS m/z 498.37$[M+H]^+$, 520.35 $[M+Na]^+$, 496.34 $[M-H]^-$; $^1H$ NMR (400 MHz, $CDCl_3$) δ 6.00 (s, 2H), 5.26 (t, J=3.1 Hz, 1H), 4.43 (dd, J=9.6, 6.3 Hz, 1H), 1.98 (s, 3H), 1.97-1.86 (m, 3H), 1.84-1.77 (m, 2H), 1.67 (m, 2H), 1.55 (m, 3H), 1.48 (m, 5H), 1.37 (m, 2H), 1.31-1.22 (m, 2H), 1.06-0.98 (m, 5H), 0.89 (d, J=3.9 Hz, 6H), 0.81 (d, J=6.9 Hz, 3H), 0.80 (s, 3H), 0.79 (s, 3H), 0.78 (s, 3H), 0.77 (d, J=11.8 Hz, 2H).

Synthesis of UAMMC1

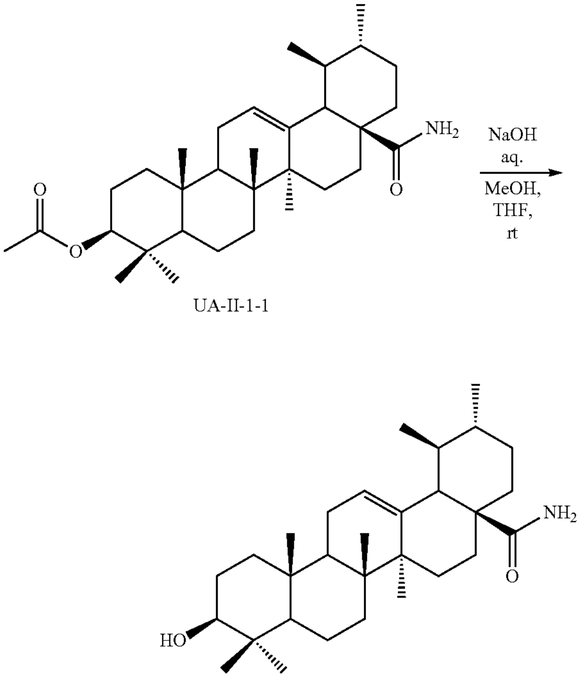

UA-II-1-1

UAMMC1

0.3 g UA-II-1-1 were dissolved in 3 mL of a mixture solvent (THF:MeOH (V (V)=3:2), and stirred at room temperature. 1.5 mL of 4N NaOH solution was added into the solution, and the reaction was monitored by TLC ($CH_2Cl_2$:MeOH=10:1). After the reaction was completed, the solvent was removed under reduced pressure, and the residue was extracted with 30 mL distilled water and 30 mL EA. The organic layer was washed twice with brine, and dried with anhydrous $MgSO_4$. After removing the solvent under reduced pressure, 0.23 g UAMMC1 was obtained as white solid powder with a yield of 83.7%. Melting point: 282.9-283.7° C. ESI-MS m/z 454.48 $[M-H]^-$; $^1H$ NMR (400 MHz, $CDCl_3$) δ 5.88 (s, 1H), 5.65 (s, 1H), 5.25 (s, 1H), 3.16 (d, J=10.3 Hz, 1H), 2.01-1.76 (m, 6H), 1.66 (m, 2H), 1.57 (m, 3H), 1.46 (m, 5H), 1.41-1.32 (m, 2H), 1.31-1.23 (m, 2H), 1.18 (m, 1H), 1.04 (s, 3H), 1.02 (m, 1H), 0.92 (m, 4H), 0.89 (s, 3H), 0.86 (s, 3H), 0.80 (d, J=10.4 Hz, 6H), 0.72 (s, 3H), 0.66 (d, J=11.2 Hz, 1H).

UAMMC2:

Synthesis of UA-I-1-7.

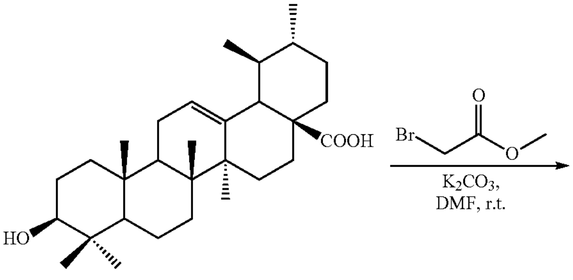

UA

-continued

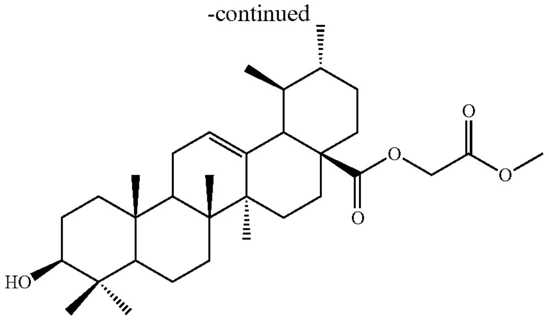

UA-I-1-7

5.23 g ursolic acid (11.45 mmol, 1 eq) was dissolved in 30 mL DMF, 1.91 g anhydrous $K_2CO_3$ (13.74 mmol, 1.2 eq) was added, and stirred at room temperature. 1.99 g methyl bromoacetate (12.60 mmol, 1.1 eq) was added and reacted overnight. After the reaction was completed, the solution was poured into 200 mL distilled water, and insoluble substances precipitated. The precipitate was filtered and dried to get the crude product, then separated by a silica gel column to obtain 5.21 g UA-I-1-7 as white solid powder with a yield of 86.1%. Melting point: 173.3-174.9° C. ESI-MS m/z 529.35 $[M+H]^+$, 551.19$[M+Na]^+$, 527.07 $[M-H]^-$; $^1H$ NMR (400 MHz, $CDCl_3$) δ 5.25 (t, J=3.5 Hz, 1H), 4.54 (dd, $J_1$=32.0 Hz, $J_2$=15.6 Hz, 2H), 3.73 (s, 3H), 3.21 (dd, $J_1$=10.8 Hz, $J_2$=4.8 Hz, 1H), 2.25 (d, J=11.2 Hz, 1H), 2.04 (td, $J_1$=13.2 Hz, $J_2$=4.4 Hz, 1H), 1.90 (dd, $J_1$=8.8 Hz, $J_2$=3.5 Hz, 2H), 1.78 (m, 3H), 1.71 (d, J=4.0 Hz, 1H), 1.64 (m, 3H), 1.49 (m, 6H), 1.32 (m, 4H), 1.11 (m, 1H), 1.08 (s, 3H), 1.04 (m, 1H), 0.99 (s, 3H), 0.94 (d, J=6.1 Hz, 3H), 0.91 (s, 3H), 0.86 (d, J=6.4 Hz, 3H), 0.78 (s, 3H), 0.74 (s, 33H), 0.72 (d, J=14.0 Hz, 1H).

Synthesis of UAMMC2.

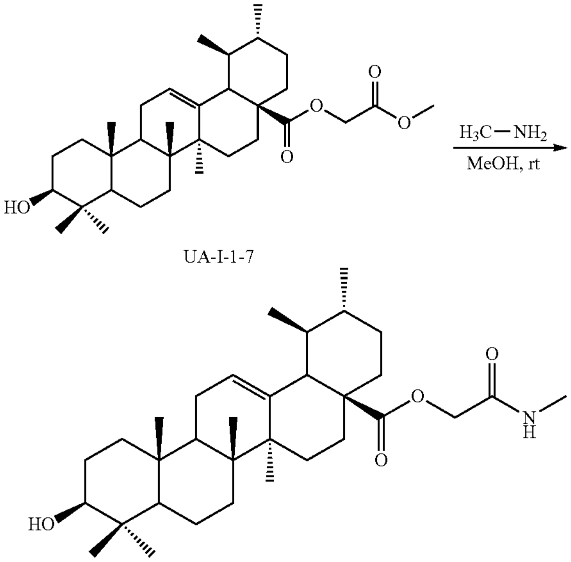

UA-I-1-7

UAMMC2

0.3 g UA-I-1-7 (0.567 mmol, 1 eq) was dissolved in 15 mL methanol and stirred at room temperature. 10 mL 33% methylamine methanol solution was added, and the mixture gradually became turbid. The reaction was monitored by TLC (PE:EA=2:1). After the reaction was completed, the reaction solution was filtered, and the precipitate was washed with methanol. After drying, 0.23 g UAMMC2 was obtained as white powder with a yield of 76.8%. Melting point: 246.0-247.1° C. ESI-MS m/z 550.46 $[M+Na]^+$, 526.44 $[M-H]^-$; TOF-HRMS m/z: calcd for $C_{33}H_{53}NO_4$ 527.3975; found 528.4036 $[M+H]^+$; $^1H$ NMR (400 MHz, $CDCl_3$) δ 6.28 (s, 1H), 5.26 (t, J=3.2 Hz, 1H), 4.78 (d, J=15.7 Hz, 1H), 4.24 (d, J=15.7 Hz, 1H), 3.20 (dd, $J_1$=11.3 Hz, $J_2$=4.4 Hz, 1H), 2.86 (d, J=4.8 Hz, 3H), 2.22 (d, J=11.1 Hz, 1H), 2.01 (m, 2H), 1.86 (ddd, $J_1$=18.6 Hz, $J_2$=11.3 Hz, $J_3$=2.8 Hz, 1H), 1.71 (m, 3H), 1.61 (m, 5H), 1.52 (m, 3H), 1.45 (m, 1H), 1.34 (m, 4H), 1.12 (m, 1H), 1.09 (s, 3H), 1.03 (m, 1H), 0.97 (s, 3H), 0.95 (d, J=6.0 Hz, 3H), 0.88 (s, 3H), 0.87 (d, J=6.6 Hz, 3H), 0.76 (s, 3H), 0.70 (d, J=10.8 Hz, 1H), 0.67 (s, 3H); $^{13}C$ NMR (101 MHz, $CDCl_3$) δ 175.97, 168.21, 140.23, 125.13, 79.02, 77.48, 77.16, 76.84, 62.88, 55.25, 52.99, 48.48, 47.47, 42.35, 39.55, 39.24, 38.93, 38.84, 38.62, 37.03, 36.81, 32.91, 30.58, 28.22, 27.84, 27.23, 26.01, 24.51, 23.76, 23.29, 21.24, 18.32, 17.13, 17.01, 15.73, 15.49.

UAMMC3

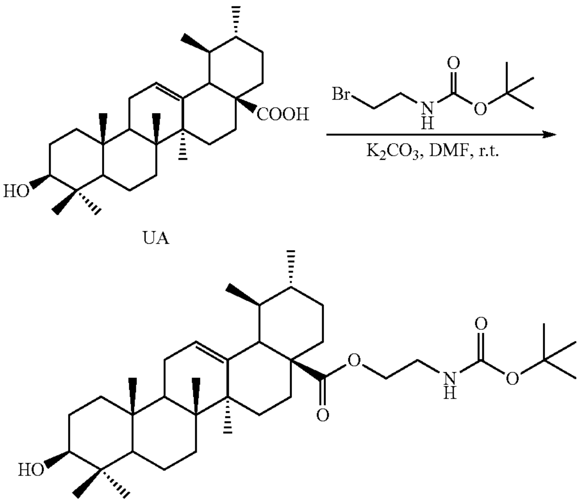

UA

UAMMC3

1 g ursolic acid (2.19 mmol, 1 eq) was dissolved in 30 mL DMF, 0.36 g anhydrous $K_2CO_3$ (2.63 mmol, 1.2 eq) was added, and stirred at room temperature. 0.57 g 2-(Boc-amino)ethyl bromide (2.41 mmol, 1.1 eq) was added and reacted overnight. After the reaction was completed, the solution was poured into 200 mL distilled water, and insoluble substances precipitated. The precipitate was filtered and dried to get 1.07 g UAMMC3 as white solid powder with a yield of 82.0%. ESI-MS m/z 598.83 [M-H]; $^1H$ NMR (400 MHz, $CDCl_3$) δ 5.27 (t, J=3.3 Hz, 1H), 4.76 (s, 1H), 4.04 (m, 2H), 3.38 (s, 2H), 3.21 (dd, $J_1$=11.2 Hz, $J_2$=4.4 Hz, 1H), 2.22 (d, J=11.3 Hz, 1H), 1.98 (m, 3H), 1.77 (m, 1H), 1.64 (m, 8H), 1.51 (m, 5H), 1.45 (s, 9H), 1.33 (m, 5H), 1.09 (m, 4H), 1.03 (m, 1H), 0.98 (s, 3H), 0.94 (d, J=5.8 Hz, 3H), 0.91 (s, 3H), 0.86 (d, J=6.4 Hz, 3H), 0.77 (s, 3H), 0.72 (s, 3H), 0.70 (d, J=10.8 Hz, 1H).

UAMMC4

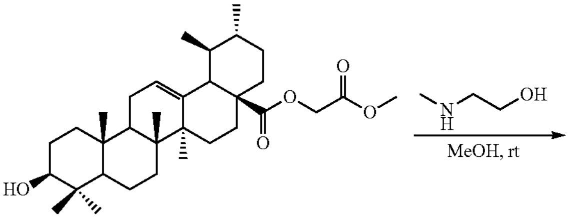

UA-I-1-7

-continued

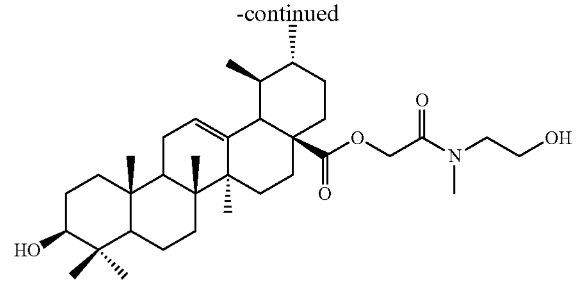

UAMMC4

0.3 g UA-I-1-7 (0.567 mmol, 1 eq) and 0.21 g N-methylethanolamine (2.84 mmol, 5 eq) were dissolved in 25 mL methanol and refluxed for about 48 h. After the reaction was completed, the solvent was evaporated under reduced pressure. 10 mL methanol was added to the residue, filtered, and the precipitate was washed with methanol. 0.18 g UAMMC4 was obtained as white powder with a yield of 55.5%. Melting point: 202.8-204.2° C. ESI-MS m/z 572.54 $[M+H]^+$, 594.28$[M+Na]^+$; TOF-HRMS m/z: calcd for $C_{35}H_{57}NO_5$ 571.4237; found 572.4290 $[M+H]^+$; $^1H$ NMR (400 MHz, $CDCl_3$) δ 5.22 (m, 1H), 4.75 and 4.64 (dd, J=28.4, 14.2 Hz, 2H), 3.75 (m, 2H), 3.52 and 3.39 (t, J=4.8 Hz, 1H), 3.20 (dd, $J_1$=10.8 Hz, $J_2$=4.7 Hz, 1H), 3.04 and 2.94 (s, 3H), 2.25 (d, J=11.2 Hz, 1H), 2.03 (m, 1H), 1.89 (m, 2H), 1.76 (m, 4H), 1.61 (m, 3H), 1.48 (m, 5H), 1.33 (m, 4H), 1.08 (m, 4H), 1.01 (m, 1H), 0.97 (m, 4H), 0.92 (d, J=6.2 Hz, 3H), 0.90 (s, 3H), 0.84 (d, J=6.4 Hz, 3H), 0.76 (s, 3H), 0.73 (d, J=4.4 Hz, 3H), 0.70 (d, J=11.6 Hz, 1H).

UAMMC5

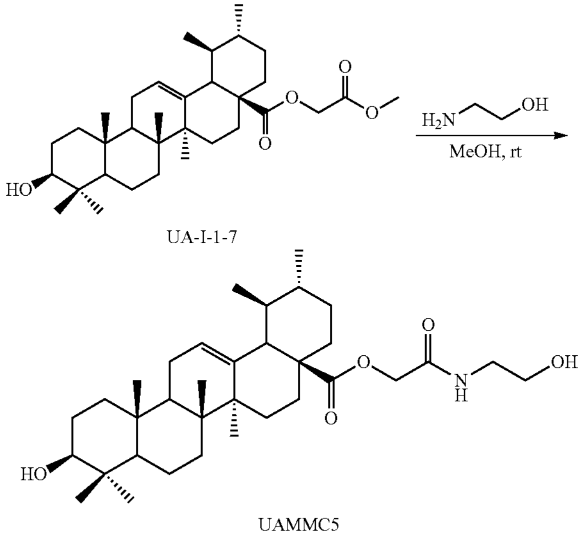

UA-I-1-7

UAMMC5

0.3 g UA-I-1-7 (0.567 mmol, 1 eq) and 0.18 g ethanolamine (2.84 mmol, 5 eq) were dissolved in 25 mL methanol and refluxed for about 24 h. After the reaction was completed, the solvent was removed under reduced pressure, and the residue was extracted with 20 mL distilled water and 20 mL EA. The organic layer was washed twice with brine and dried with anhydrous $MgSO_4$. After the solvent was removed under reduced pressure, 0.23 g UAMMC5 was obtained as white solid powder with a yield was 72.7%. Melting point: 121.5-123.3° C. ESI-MS m/z 556.27 $[M-H]^-$; TOF-HRMS m/z: calcd for $C_{34}H_{55}NO_5$ 557.4080; found 558.4153 $[M+H]^+$; $^1H$ NMR (400 MHz, $CDCl_3$) δ 6.66 (t, J=5.2 Hz, 1H), 5.29 (t, J=3.3 Hz, 1H), 4.71 (d, J=15.8 Hz, 1H), 4.33 (d, J=15.8 Hz, 1H), 3.75 (t, J=5.0 Hz, 2H), 3.53 (ddd, $J_1$=15.6 Hz, $J_2$=10.6 Hz, $J_3$=5.2 Hz, 1H), 3.41 (ddd, $J_1$=15.6 Hz, $J_2$=10.6 Hz, $J_3$=5.2 Hz, 1H), 3.20 (dd, $J_1$=11.4 Hz, $J_2$=4.4 Hz, 1H), 2.22 (d, J=11.1 Hz, 1H), 2.06 (m, 2H), 1.90 (m, 3H), 1.73 (m, 3H), 1.63 (m, 4H), 1.51 (m, 4H), 1.34 (m, 5H), 1.12 (m, 1H), 1.09 (s, 3H), 1.03 (m, 1H), 0.97 (s, 3H), 0.95 (d, J=6.1 Hz, 3H), 0.89 (s, 3H), 0.86 (d, J=6.4 Hz, 3H), 0.77 (s, 3H), 0.70 (d, J=11.6 Hz, 1H), 0.69 (s, 3H).

UAMMC6

Synthesis of UA-II-1-2.

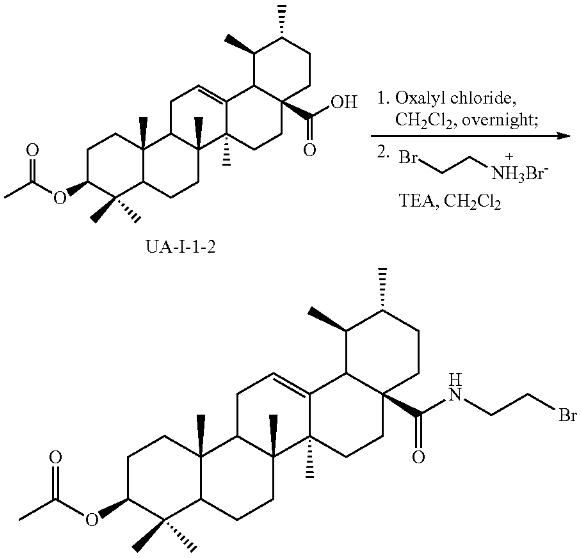

UA-I-1-2

UA-II-1-2

The intermediate of 3-acetoxy ursolic acid acyl chloride was prepared from 4.00 g UA-I-1-2 (8.01 g mmol, 1 eq),) according to the above method. 2.00 g bromoethylamine hydrobromide (9.62 mmol, 1.2 eq) and 2.43 g TEA (24.06 mmol, 3 eq) were dissolved in 30 mL $CH_2Cl_2$ and added dropwise to the mixture. After the reaction was completed, the reaction solution was washed with 50 mL distilled water and brine, and the organic layer was dried with anhydrous $MgSO_4$. 4.64 g UA-II-1-2 was obtained as white powder after removing the solvent under reduced pressure with a yield of 95.7%. Melting point: 196.9-198.4° C.; $^1H$ NMR (400 MHz, $CDCl_3$) δ 5.21 (t, J=3.2 Hz, 1H), 4.48 (dd, $J_1$=9.4 Hz, $J_2$=6.5 Hz, 1H), 4.11 (t, J=9.4 Hz, 2H), 3.76 (t, J=9.4 Hz, 2H), 2.19 (d, J=11.2 Hz, 1H), 2.03 (m, 4H), 1.90 (m, 3H), 1.62 (m, 6H), 1.49 (m, 5H), 1.35 (m, 4H), 1.06 (s, 3H), 1.04 (m, 1H), 1.01 (m, 1H), 0.93 (d, J=2.5 Hz, 6H), 0.85 (m, 9H), 0.79 (d, J=9.4 Hz, 1H), 0.77 (s, 3H).

Synthesis of UAMMC6

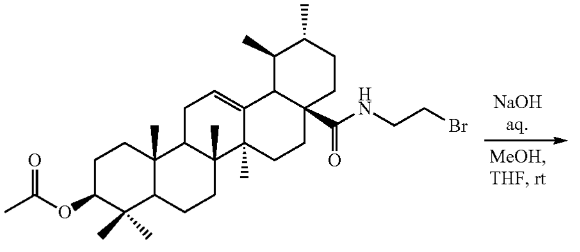

UA-II-1-2

-continued

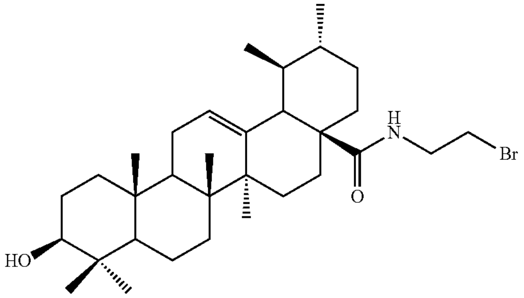

UAMMC6

UAMMC6 was obtained from UA-II-1-2 with the same preparation procedure for UAMMC1. 0.24 g UAMMC6 was obtained as white solid powder with a yield of 86.0%. Melting point: 258.5-260.3° C. $^1$H NMR (400 MHz, $CDCl_3$) δ 5.21 (t, J=3.2 Hz, 1H), 4.12 (t, J=9.2 Hz, 2H), 3.77 (t, J=9.2 Hz, 2H), 3.21 (dd, $J_1$=10.2 Hz, $J_2$=4.0 Hz, 1H), 2.20 (d, J=11.1 Hz, 1H), 2.06 (t, J=13.2 Hz, 1H), 1.92 (m, 3H), 1.65 (m, 5H), 1.50 (m, 5H), 1.33 (m, 5H), 1.08 (m, 4H), 1.00 (m, 5H), 0.93 (m, 6H), 0.85 (d, J=5.7 Hz, 3H), 0.77 (s, 6H), 0.72 (d, J=11.2 Hz, 1H).

UAMMC7

Synthesis of UA-II-1-5

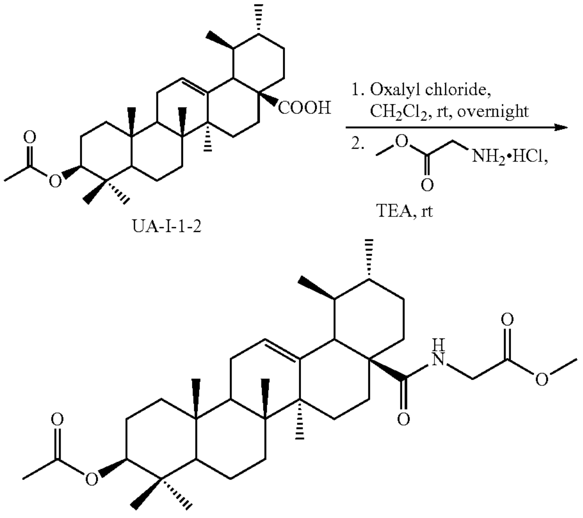

UA-I-1-2

UA-II-1-5

The intermediate of 3-acetoxy ursolic acid acyl chloride was prepared from 4.00 g 3-acetylursolic acid (8.01 mmol, 1 eq) according to the above method. 1.36 g glycine methyl ester hydrochloride (9.62 mmol, 1.2 eq) and 2.43 g TEA (24.06 mmol, 3 eq) were dissolved in 30 mL $CH_2Cl_2$ and added dropwise to the reaction mixture. After the reaction was completed, the reaction solution was washed with 50 mL distilled water and brine, and the organic layer was dried with anhydrous $MgSO_4$. The crude UA-II-1-5 was obtained by removing the solvent under reduced pressure. The crude product was recrystallized with 15 mL methanol to obtain 3.84 g UA-II-1-5 as white powder with a yield of 82.0%. Melting point: 115.9-117.8° C. ESI-MS m/z 570.27[M+H]$^+$, 592.49 [M+Na]$^+$, 568.34 [M−H]; $^1$H NMR (400 MHz, $CDCl_3$) δ 6.52 (s, 1H), 5.40 (t, J=3.2 Hz, 1H), 4.49 (dd, $J_1$=10.2 Hz, $J_2$=4.0 Hz, 1H), 4.10 (d, J=18.8 Hz, 1H), 3.83 (d, J=18.8 Hz, 1H), 3.76 (s, 3H), 2.04 (s, 3H), 1.98 (m, 3H), 1.86 (d, J=13.2 Hz, 1H), 1.73 (d, J=13.2 Hz, 1H), 1.60 (m, 4H), 1.48 (m, 6H), 1.31 (m, 5H), 1.09 (s, 3H), 1.03 (m, 2H), 0.95 (s, 3H), 0.93 (s, 3H), 0.89 (d, J=6.0 Hz, 3H), 0.85 (s, 6H), 0.83 (d, J=11.2 Hz, 1H), 0.71 (s, 3H).

Synthesis of UA-II-1-8.

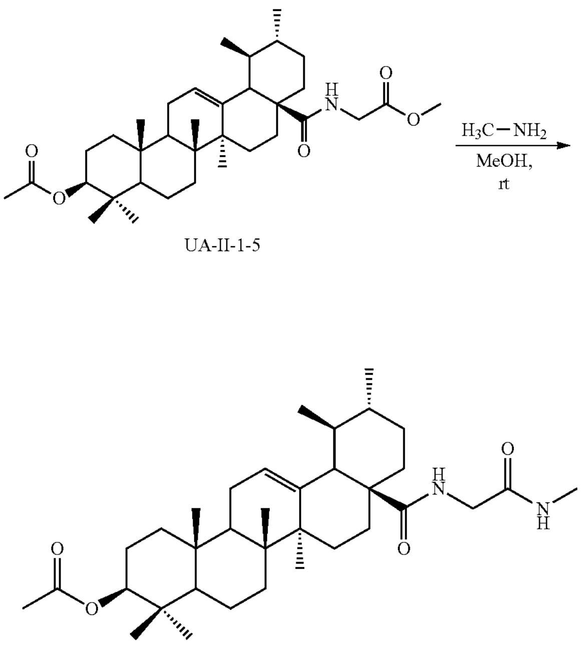

UA-II-1-5

UA-II-1-8

0.3 g UA-II-1-5 (0.526 mmol, 1 eq) was dissolved in 15 mL methanol and stirred at room temperature. 10 mL 33% methylamine methanol solution was added, and the mixture gradually became turbid. The reaction was monitored by TLC (PE:EA=2:1). After the reaction was completed, the reaction solution was filtered, and the precipitate was washed with methanol. After drying, 0.20 g UA-II-1-8 was obtained as white powder with a yield of 72.2%. Melting point: 140.1-143.4° C. ESI-MS m/z 569.39 [M+H]$^+$, 591.23 [M+Na]$^+$, 559.35 [M−H]$^-$; TOF-HRMS m/z: calcd for $C_{35}H_{56}N_2O_4$ 568.4240; found 569.4194 [M+H]$^+$; $^1$H NMR (400 MHz, $CDCl_3$) δ 6.92 (s, 1H), 5.41 (t, J=3.2 Hz, 1H), 3.98 (d, J=14.2 Hz, 1H), 3.79 (d, J=15.6 Hz, 1H), 3.52 (brs, 1H), 3.21 (dd, $J_1$=11.2 Hz, $J_2$=4.4 Hz, 1H), 2.81 (s, 3H), 2.01 (m, 4H), 1.82 (m, 1H), 1.70 (m, 1H), 1.51 (m, 6H), 1.32 (m, 3H), 1.09 (s, 3H), 1.04 (m, 1H), 0.99 (m, 1H), 0.98 (s, 3H), 0.95 (s, 3H), 0.90 (s, 3H), 0.87 (d, J=6.4 Hz, 3H), 0.77 (s, 3H), 0.71 (d, J=11.2 Hz, 1H), 0.69 (s, 3H).

Synthesis of UAMMC7

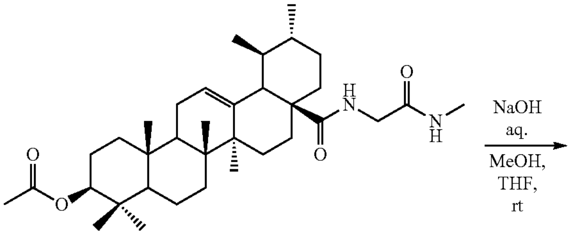

UA-II-1-8

-continued

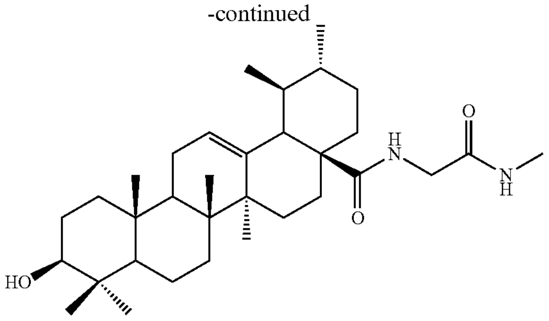

UAMMC7

UAMMC7 was obtained from UA-II-1-8 with the same preparation procedure for UAMMC1. 0.26 g UAMMC6 was obtained as white solid powder with a yield of 93.6%. Melting point: 237.3-238.8° C. ESI-MS m/z 527.35 $[M+H]^+$, 549.44 $[M+Na]^+$; TOF-HRMS m/z: calcd for $C_{33}H_{54}N_2O_3$ 526.4134; found 527.4178 $[M+H]^{30}$; $^1H$ NMR (400 MHz, $CDCl_3$) δ 6.92 (s, 1H), 5.41 (t, J=3.2 Hz, 1H), 3.98 (d, J=14.2 Hz, 1H), 3.79 (d, J=15.6 Hz, 1H), 3.52 (brs, 1H), 3.21 (dd, $J_1$=11.2 Hz, $J_2$=4.4 Hz, 1H), 2.81 (s, 3H), 2.01 (m, 4H), 1.82 (m, 1H), 1.70 (m, 1H), 1.51 (m, 6H), 1.32 (m, 3H), 1.09 (s, 3H), 1.04 (m, 1H), 0.99 (m, 1H), 0.98 (s, 3H), 0.95 (s, 3H), 0.90 (s, 3H), 0.87 (d, J=6.4 Hz, 3H), 0.77 (s, 3H), 0.71 (d, J=11.2 Hz, 1H), 0.69 (s, 3H).

UAMMC8 and UAMMC9

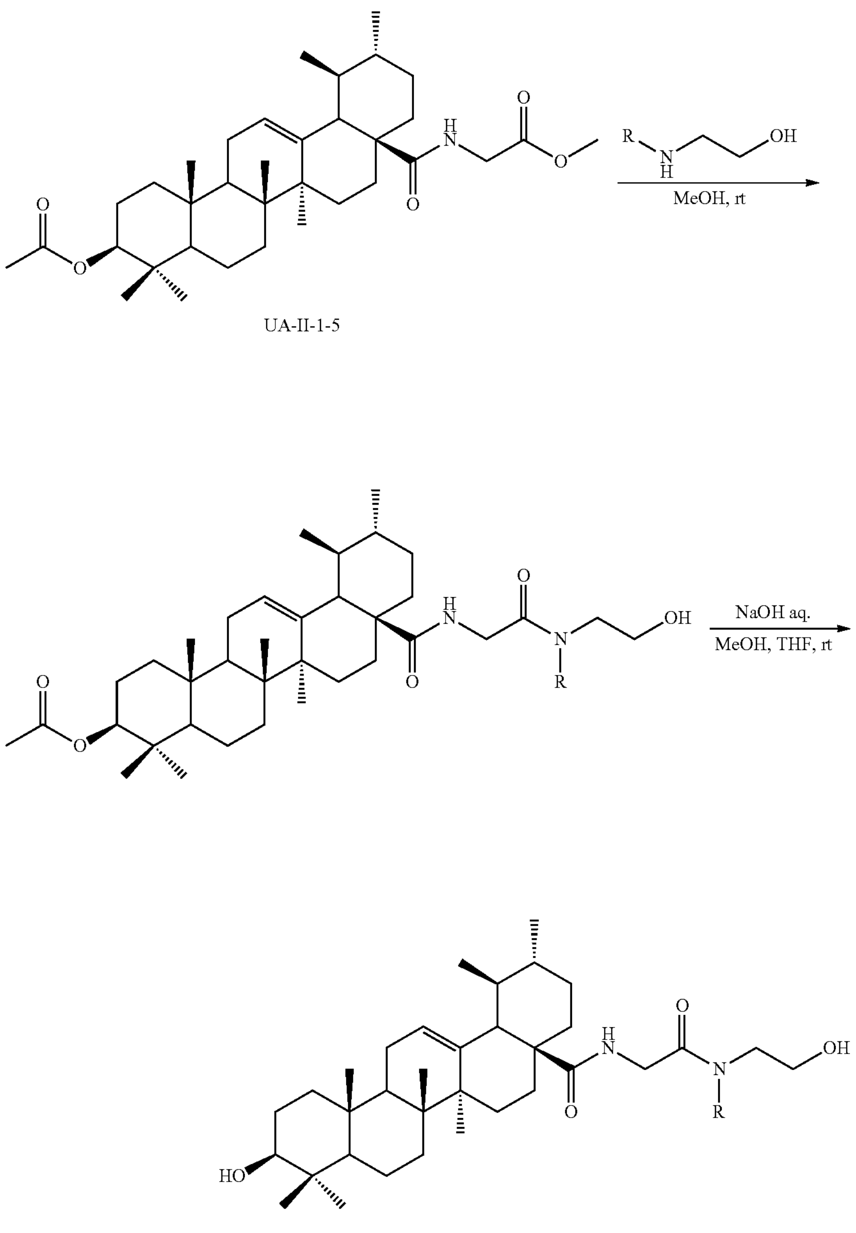

UA-II-1-5

UAMMC8: R = H;
UAMMC9: R = $CH_3$ 0.3 g UA-II-1-5 (0.526 mmol, 1 eq) and amino alcohol (10 eq) were dissolved in 25 mL methanol, and heated to reflux. When the raw material was consumed completely on TLC ($CH_2Cl_2$:MeOH=10:1), the solvent was removed under reduced pressure, and the residue was extracted with 30 mL distilled water and 30 mL EA. The organic layer was washed twice with brine and dried with anhydrous $MgSO_4$. Removed the solvent under reduced pressure, the crude products of the corresponding intermediates were obtained, which were directly used in the next step without purification.

The crude product of the previous step was dissolved in 10 mL of mixed solvent (THF:MeOH (V:V)=3:2) and stirred at room temperature. 5 mL 4N NaOH solution was added, and the reaction was monitored by TLC. After the reaction was completed, removed most of the solvent under reduced pressure, and the residues were extracted with 30 mL distilled water and 30 mL EA. The organic layer was washed twice with brine and dried with anhydrous $MgSO_4$. After removing the solvent under reduced pressure, the residue was separated on a silica gel column ($CH_2Cl_2$:MeOH (V:V) =50:1→30:1), and the corresponding product was obtained.

UAMMC8: white solid powder with a yield of 63.2% (2 steps). Melting point: 202.5-204.9° C. ESI-MS m/z 557.42 $[M+H]^{30}$, 579.30 $[M+Na]^+$, 555.57 $[M-H]^-$; TOF-HRMS m/z: calcd for $C_{34}H_{56}N_2O_4$ 556.4240; found 557.4296 $[M+H]^+$; $^1H$ NMR (400 MHz, $CDCl_3$) δ 7.48 (t, J=5.4 Hz, 1H), 7.06 (t, J=4.0 Hz, 1H), 5.43 (t, J=3.2 Hz, 1H), 3.95 (dd, $J_1$=16.4 Hz, $J_2$=4.8 Hz, 1H), 3.77 (dd, $J_1$=16.4 Hz, $J_2$=3.6 Hz, 1H), 3.68 (t, J=4.8 Hz, 2H), 3.40 (dd, $J_1$=9.6 Hz, $J_2$=5.2 Hz, 2H), 3.18 (dd, $J_1$=10.8 Hz, $J_2$=4.8 Hz, 1H), 1.98 (m, 4H), 1.78 (m, 1H), 1.63 (m, 4H), 1.50 (m, 4H), 1.41 (m, 4H), 1.31 (m, 2H), 1.07 (s, 3H), 1.04 (m, 2H), 0.95 (s, 3H), 0.92 (m, 4H), 0.88 (s, 3H), 0.85 (d, J=6.4 Hz, 3H), 0.75 (s, 3H), 0.69 (d, J=11.2 Hz, 1H), 0.66 (s, 3H); $^{13}C$ NMR (101 MHz, $CDCl_3$) δ 179.45, 169.05, 138.53, 126.95, 78.97, 65.67, 61.70, 55.16, 53.65, 47.83, 47.61, 42.33, 39.78, 39.60, 39.03, 38.81, 38.71, 36.96, 32.73, 30.87, 30.63, 28.19, 27.83, 27.23, 24.94, 23.53, 23.48, 21.27, 19.26, 18.37, 17.24, 16.52, 15.77, 15.58.

UAMMC9: white solid powder with a yield of 74.2% (2 steps). Melting point: 250.1-251.9° C. ESI-MS m/z 571.46 $[M+H]^{30}$, 593.51 $[M+Na]^+$; TOF-HRMS m/z: calcd for $C_{35}H_{58}N_2O_4$ 570.4397; found 571.4458 $[M+H]^+$; $^1H$ NMR (400 MHz, $CDCl_3$) δ 7.09 (m, 1H), 5.45 (t, J=3.4 Hz, 1H), 4.20 and 4.07 (dd, $J_1$=17.6 Hz, $J_2$=4.4 Hz, 1H), 3.91 (dd, $J_1$=17.8 Hz, $J_2$=2.8 Hz, 1H), 3.79 and 3.76 (t, J=5.2 Hz, 2H), 3.58 and 3.41 (ddt, $J_1$=36.0 Hz, $J_2$=14.4 Hz, $J_3$=5.2 Hz, 2H), 3.21 (dd, $J_1$=11.2 Hz, $J_2$=4.4 Hz, 1H), 3.04 and 3.00 (s, 3H), 2.63 (brs, 1H), 2.02 (m, 2H), 1.95 (m, 2H), 1.79 (m, 4H), 1.63 (m, 4H), 1.46 (m, 7H), 1.29 (m, 4H), 1.09 (s, 3H), 1.04 (m, 2H), 0.97 (s, 3H), 0.94 (m, 3H), 0.89 (s, 3H), 0.87 (d, J=7.4 Hz, 3H), 0.76 (s, 3H), 0.71 (d, J=11.6 Hz, 1H), 0.67 (s, 3H).

Introduction for Examples 2-7

Janus kinase 2 (JAK2) is one of the JAK family of intracellular non-receptor tyrosine kinases consisting of 4 mammalian members, JAK1, JAK2, JAK3, and TYK2. The canonical action of JAK2 is to activate the signal transducers and activators of transcription (STAT) proteins in cytoplasm, which then translocate to the nucleus to initiate specific transcriptional programs. The JAK2/STAT pathway is hyperactivated in many cancers, and such hyperactivation is associated with a poor clinical prognosis and drug resistance. However, the mechanism regulating its activity is poorly understood.

Small ubiquitin-related modifier (SUMO) is an ubiquitin-like protein moiety reversibly added post-translationally to target proteins by an ATP-driven cascade of enzymes consisting of activating enzyme (E1), conjugating enzyme (E2), and ligase (E3) (19,20). SUMOylation has been found to regulate many cellular events including chromatin organization, transcription, DNA damage repair, protein trafficking, and signal transduction. Like ubiquitin, SUMO can be attached as a single entity to the ε-amino group of a lysine residue on the substrate protein or SUMO itself to form a multiunit chain. SUMO moieties on modified proteins can be removed by SUMO-specific proteases called sentrin-specific proteases (SENPs) which include SENP1, SENP2, SENP3, SENP5, SENP6 and SENP7. SENP1 is a nuclear protease that has been shown to deSUMOylate several targets, including hypoxia-inducible factor-1α (HIF1α), histone deacetylase 1 and androgen receptor. SENP1 expression level is increased in human testis, breast, cervical cancer and others

Example 2. SENP1 Directly Interacts with and deSUMOylates JAK2

To identify proteins that regulate Janus kinase 2 (JAK2) activity, JAK2 proteins were first purified using HEK293T cells that expressed His-tagged JAK2. The immunoprecipitated His-JAK2 and its associated proteins were subjected to mass spectrometry analysis that identified a number of well-known JAK2-associated proteins, including STAT3, STAT5A and STAT1. Interestingly, sentrin-specific protease 1 (SENP1) was also identified from JAK2 immunoprecipitates (FIG. 2A). To validate the SENP1-JAK2 interaction in cells, FLAG-tagged SENP1 (FLAG-SENP1) was expressed in HEK293T cells followed by immunoprecipitation with FLAG antibody. As shown in FIG. 2B, JAK2 was detected from immunoprecipitates of FLAG-SENP1. To determine whether SENP1 and JAK2 interact directly, an in vitro affinity capture assay was performed by using purified recombinant glutathione-S-transferase-tagged-SENP1 (GST-SENP1) to pull down His-tagged-JAK2 (His-JAK2). While GST alone did not capture His-JAK2, GST-SENP1 successfully pulled down His-JAK2, indicating a direct interaction between SENP1 and JAK2 (FIG. 2C).

Figure 2D:
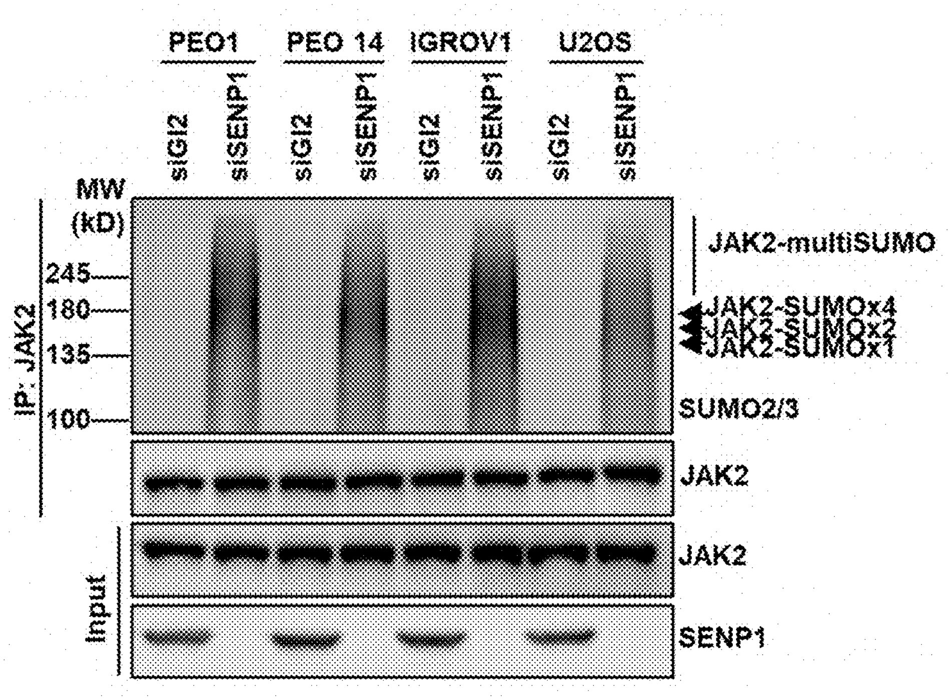
Figure 2E:
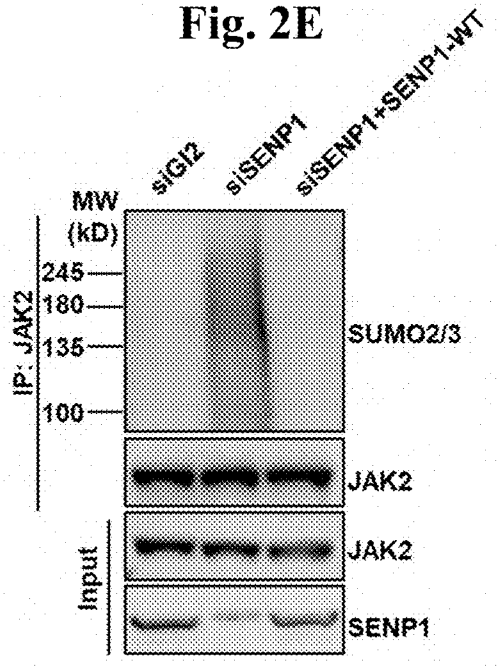

To determine the functional consequence of SENP1-JAK2 interaction, it was examined whether inhibition of SENP1 affected SUMOylation of JAK2. To this end, JAK2 was immunoprecipitated and the SUMOylation level of JAK2 was evaluated using an antibody against SUMO2/3 in SENP1 depleted cells. As shown in FIG. 2D, SENP1 knockdown resulted in the significant increase of JAK2 SUMOylation in multiple cancer cells lines including PEO1 (human ovarian adenocarcinoma), PEO14 (human ovarian adenocarcinoma), IGROV1 (human ovarian carcinoma) and U2OS (human bone osteosarcoma). To rule out the off-target effect, siRNA resistant FLAG-SENP1-WT was ectopically expressed in SENP1 depleted IGROV1 cells and found that expression of SENP1-WT significantly restored the deSUMOylation of JAK2 in SENP1 knockdown cells (FIG. 2E).

Figure 2F:
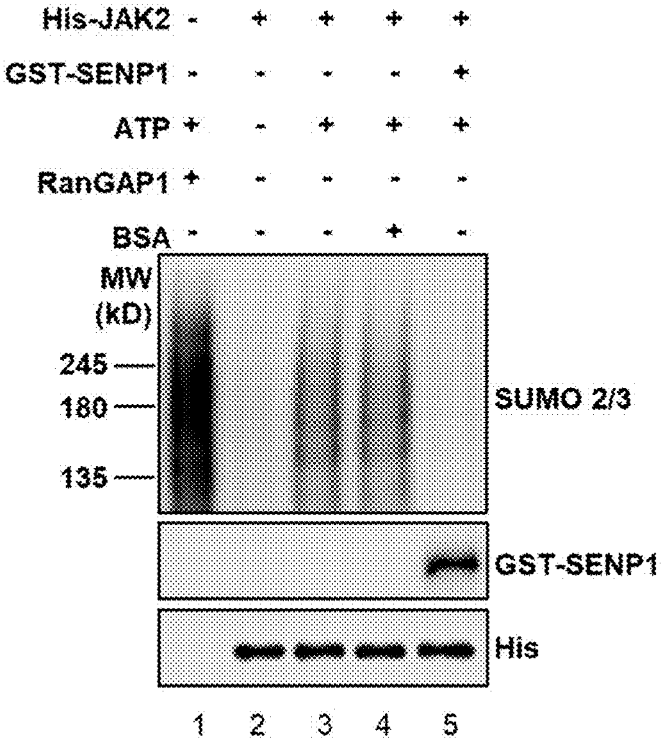
Figure 2G:
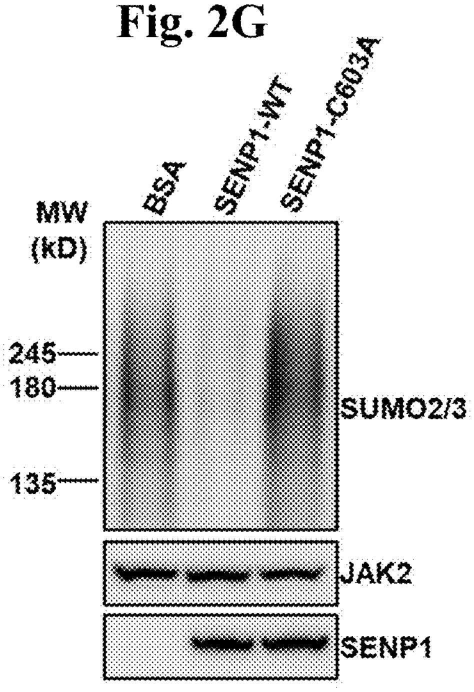

To further determine whether SENP1 can directly deSUMOylate JAK2, in vitro deSUMOylation assays were performed by using purified recombinant His-JAK2 and GST-SENP1 proteins. Using a SUMOylation kit (ENZO Life Sciences), the positive control protein RanGAP1 was found to be SUMOylated (FIG. 2F, lane 1). Like RanGAP1, JAK2 was also found to be SUMOylated as indicated by multiple upward shifts in the apparent molecular mass of the protein (FIG. 2F, lane 3). Significantly, incubation of GST-SENP1 but not BSA with JAK2 after JAK2 SUMOylation reaction completely removed SUMO from JAK2 in vitro (FIG. 2F, lane 5). Consistently, purified catalytically inactive GST-SENP1-C603A proteins exhibited lower activity to deSUMOylate JAK2 compared to GST-SENP1-WT in vitro (FIG. 2G), indicating deSUMOylation of JAK2 by SENP1 required SENP1 protease activity. Taken together, the data suggested that SENP1 directly interacted with and deSUMOylates JAK2 both in vitro and in vivo.

Example 3. DeSUMOylation of JAK2 by SENP1 Promotes Cytoplasmic Accumulation of JAK2

Figure 3A:
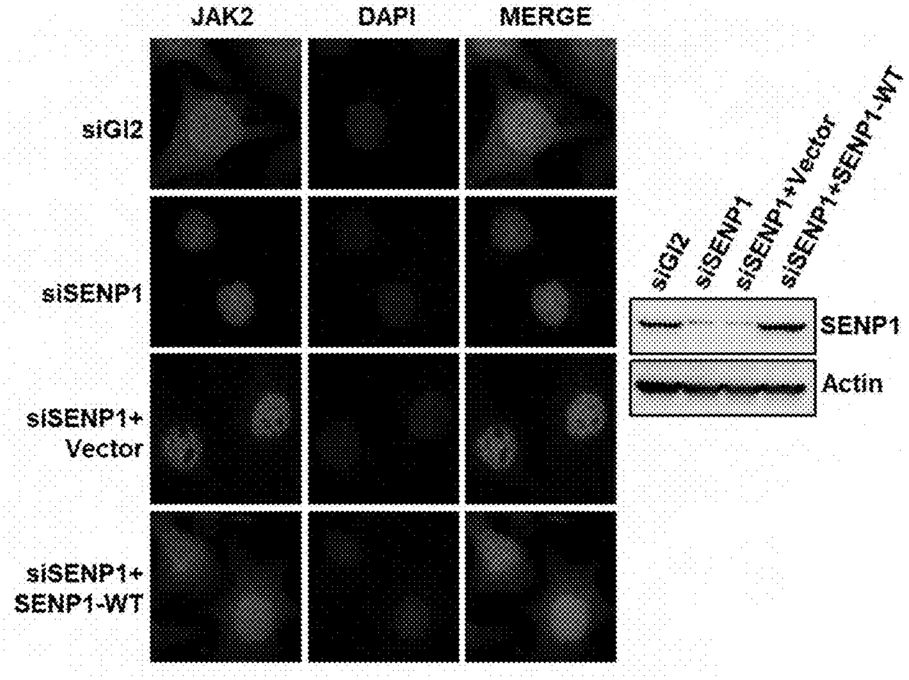
FIGS. 3A-3J depict images illustrating deSUMOylation of JAK2 by SENP1 promoted cytoplasmic accumulation of JAK2.
Figure 3B:
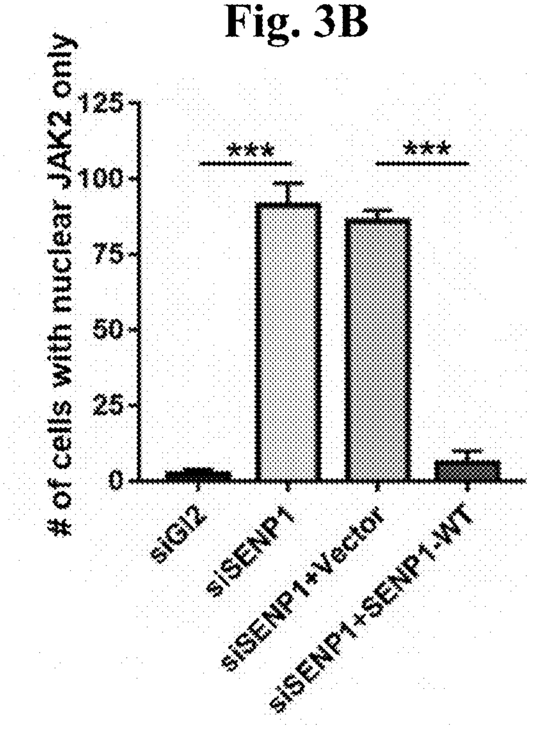
Figure 3C:
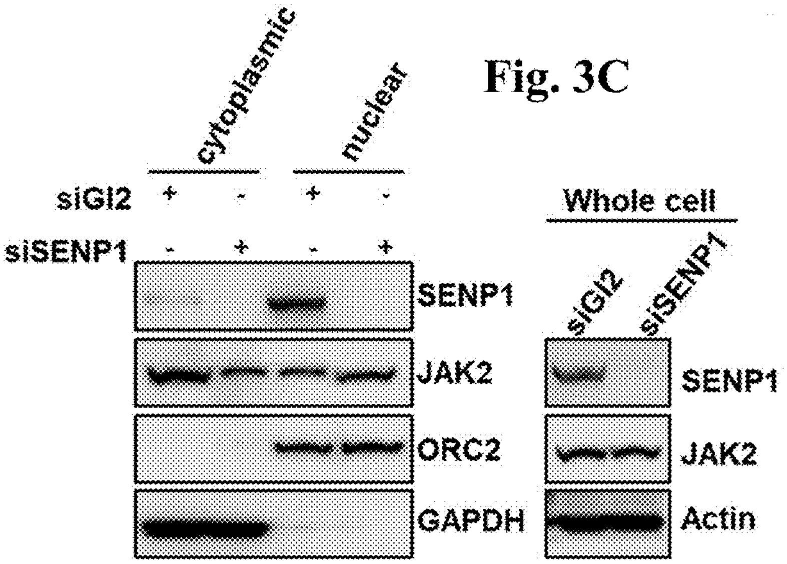

To determine if deSUMOylation of JAK2 by SENP1 controled JAK2 localization, thus affecting JAK2 activity, endogenous JAK2 was first visualized in IGROV1 cells with downregulation of SENP1 by siRNA. In control siGL2 treated cells, JAK2 localized in both cytoplasm and nucleus, whereas depletion of SENP1 by siRNAs led to the accumulation of JAK2 in nucleus (FIGS. 3A and 3B). Ectopic expression of SENP1 restored the localization of JAK2 in cytoplasm (FIGS. 3A and 3B). Consistently, the nuclear fractionation assay in IGROV1 cells revealed that nuclear JAK2 was significantly increased while cytoplasmic JAK2 was decreased in SENP1 knockdown cells as compared to siGL2 treated cells (FIG. 3C).

Figure 3D:
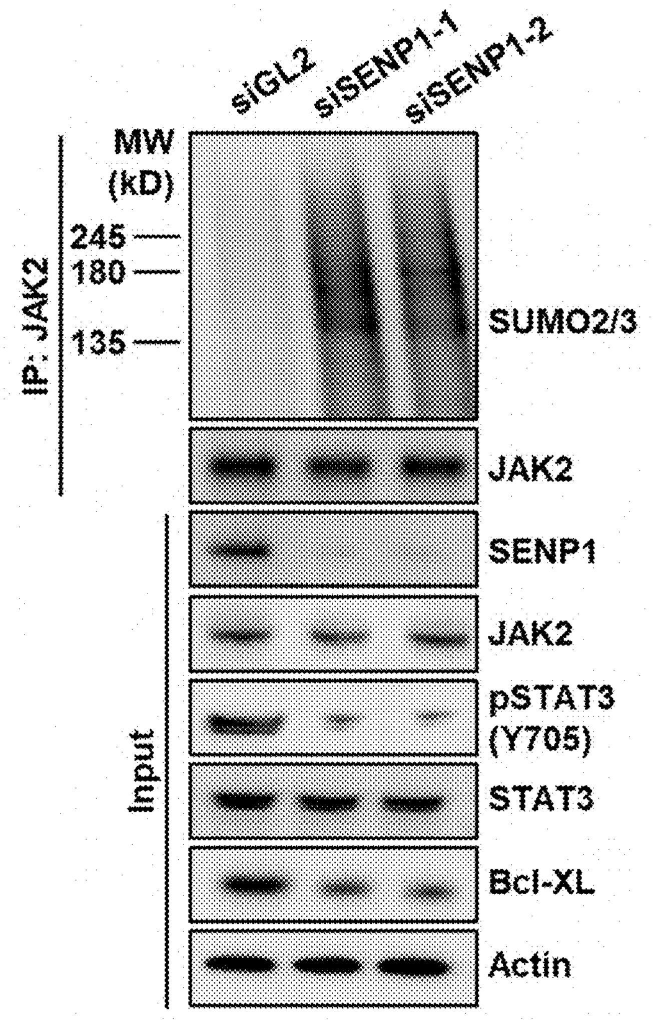
Figure 3E:
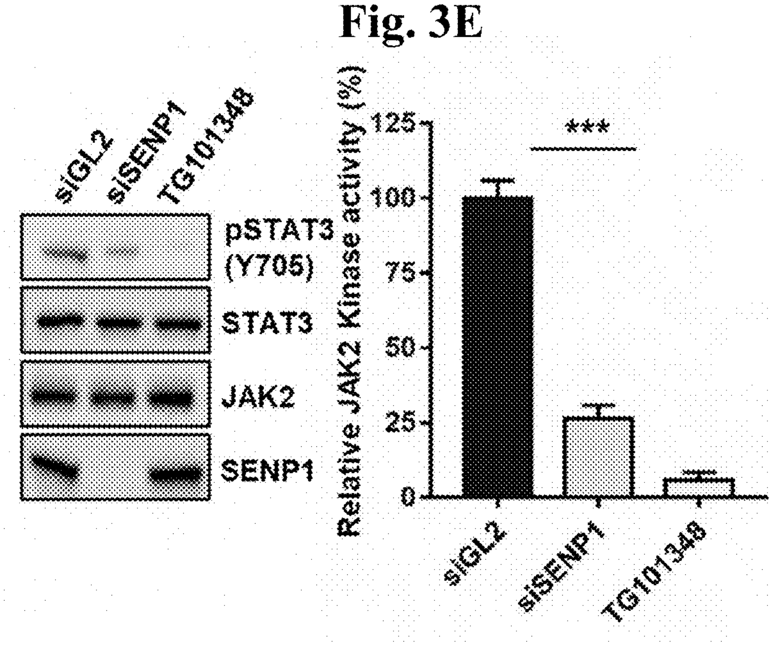

Phosphorylation of STAT3 at tyrosine 705 (Y705) by JAK2 is one of the most important and well established cytoplasmic functions of JAK2. To determine whether accumulation of JAK2 in nucleus by depleting SENP1 affected JAK2 cytoplasmic activity, phosphorylated STAT3 (pSTAT3 (Y705)) levels was evaluated in SENP1 depleted IGROV1 cells. Compared to siGL2, cells treated with two independent siSENP1s exhibited a significant decrease of pSTAT3 and anti-apoptotic protein Bcl-xL (FIG. 3D). To further confirm that SENP1 regulated JAK2 activity, a cell-free kinase assay was performed using JAK2 purified from IGROV1 cells treated with siSENP1 or JAK2 inhibitor TG101348. Consistently, purified JAK2 from cells treated with siSENP1 or TG101348 showed decreased phosphorylation of recombinant substrate STAT3 proteins (FIG. 3E), indicating that the activity of JAK2 was significantly reduced by SENP1 depletion or JAK2 inhibitor.

Figure 3F:
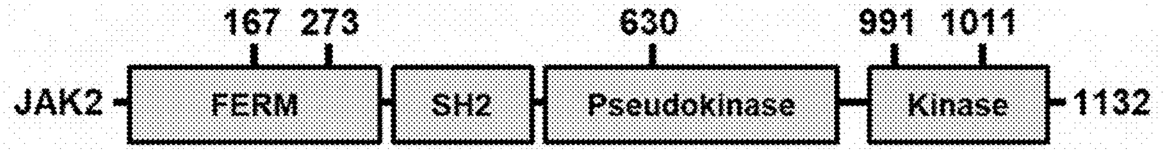
Figure 3G:
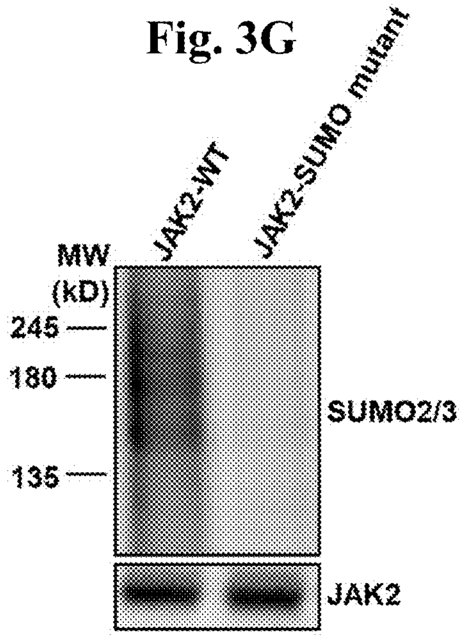
Figure 3H:
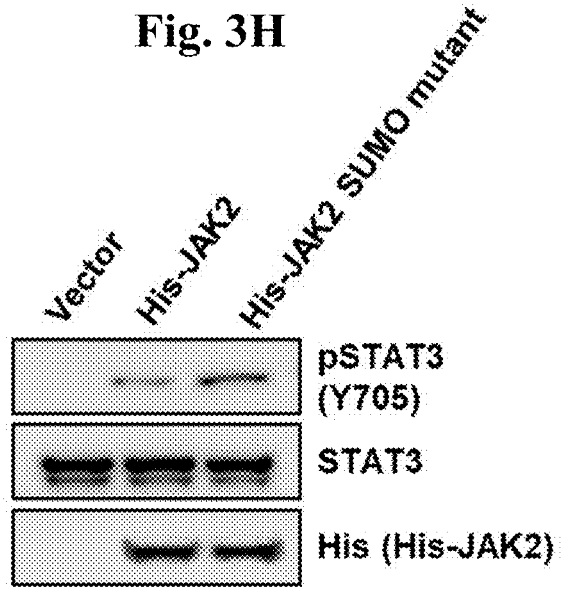
Figure 3I:
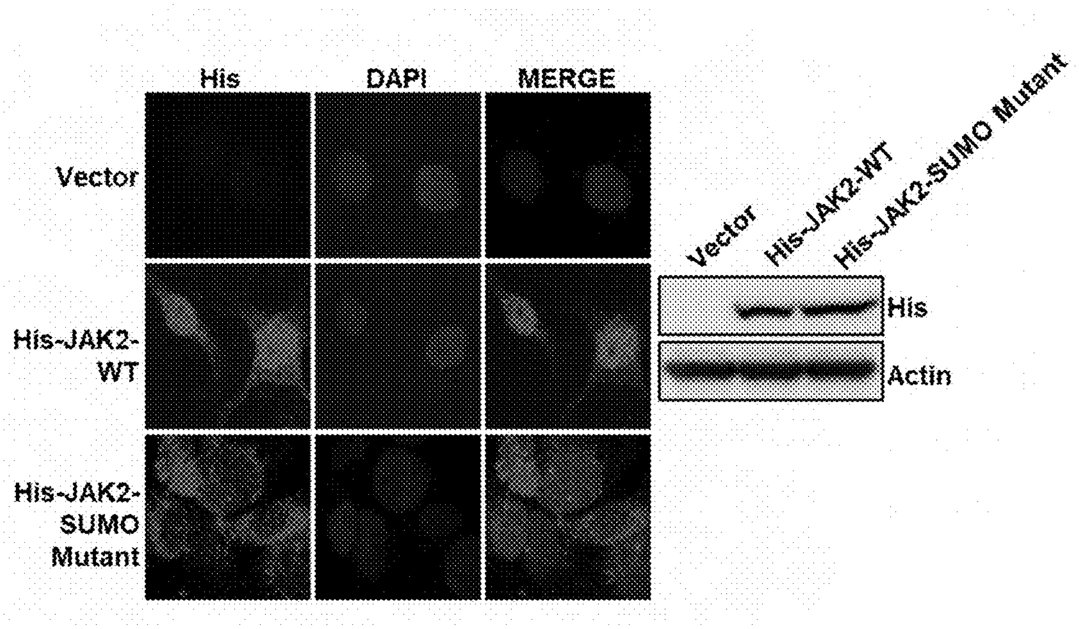
Figure 3J:
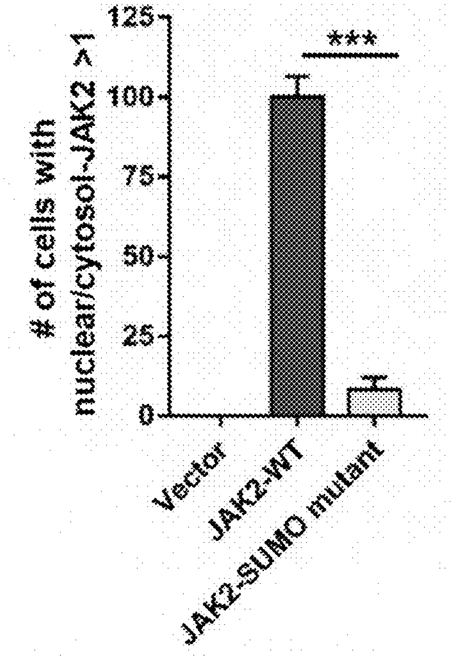

To further determine the function of JAK2 SUMOylation, five potential SUMOylation sites of JAK2 were identified in silico. All five sites identified, which were all lysine residues, were mutated to alanine (JAK2-K167A-K273A-K630A-K991A-K1011A) to create a mutant JAK2 (JAK2-SUMO mutant) (FIG. 3F). The cell-free SUMOylation assay indicated that JAK2-SUMO mutant failed to be SUMOylated as compared to JAK2-WT (FIG. 3G). Moreover, the kinase assay indicated that JAK2-SUMO exhibited the increased kinase activity on recombinant STAT3 (FIG. 3H). Immunofluorescence staining in IGROV1 cells showed that the JAK2-SUMO mutant, unlike wild type JAK2, was accumulated in cytoplasm (FIGS. 3I and 3J). Together, data showed that SENP1 controled JAK2 activity by regulating JAK2 cellular localization in cells.

Example 4. SENP1 is Upregulated in Cisplatin Resistant Cancer Cells

Figure 4A:
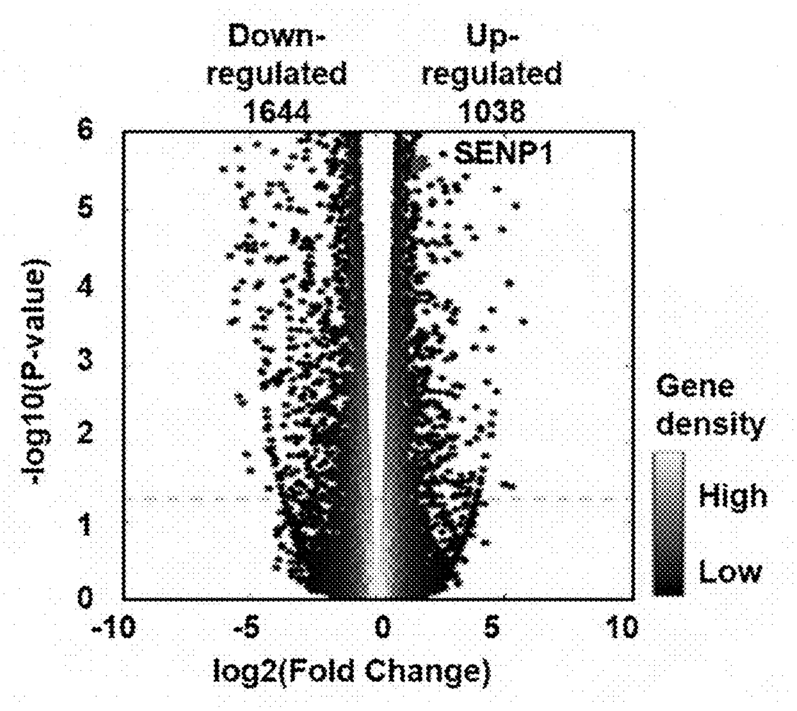
FIGS. 4A-4K depict images illustrating SENP1 upregulation in cisplatin resistant cancer cells.
Figure 4B:
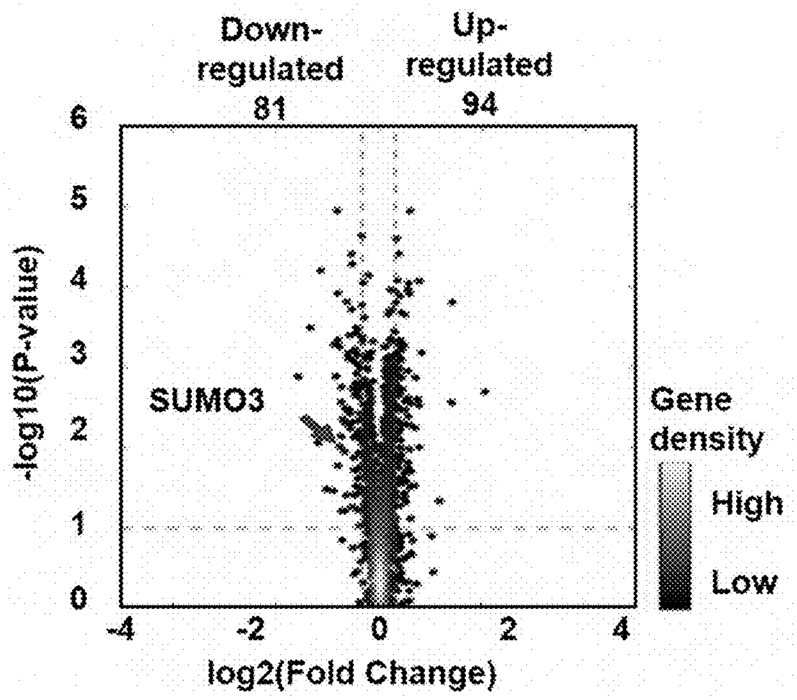

To identify genes that regulate platinum drug resistance in ovarian cancer cells, both RNA-Seq and quantitative mass-spec analyses were performed. These assays found that SENP1 mRNA was highly upregulated (FIG. 4A), while SUMO3 level was decreased in cisplatin-resistant (CR) ovarian cancer cells (IGROV1 CR) (FIG. 4B), suggesting a possible role of SENP1 in the regulation of platinum-resistance via SUMOylation in ovarian cancer.

Figure 4C:
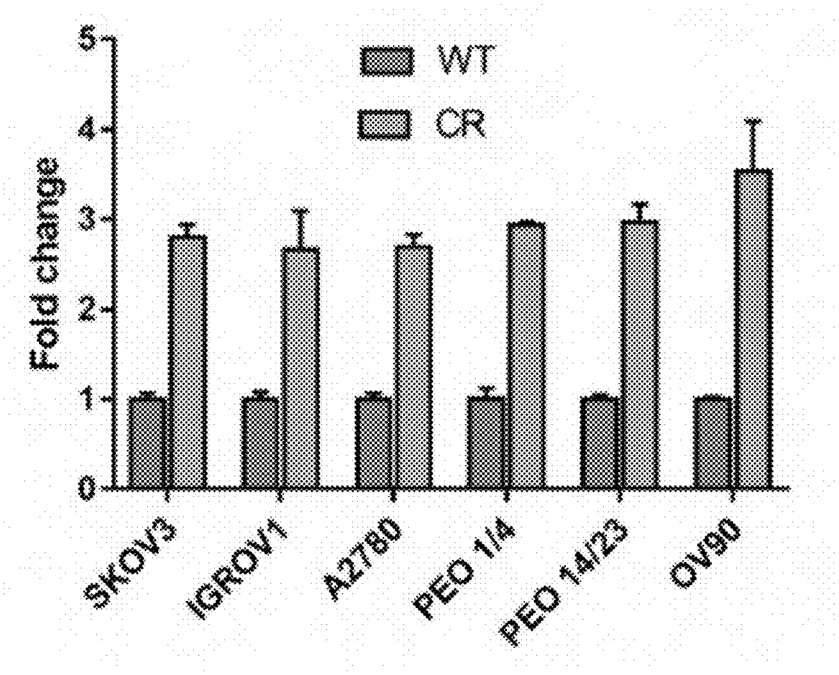
Figure 4D:
Figure 4E:
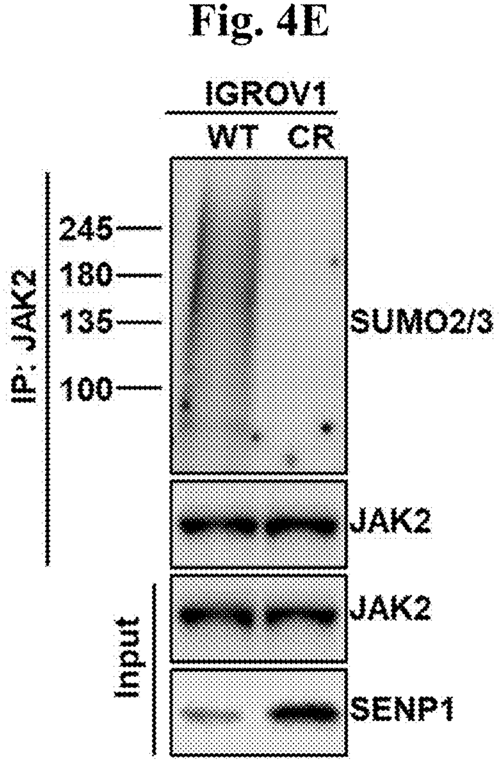

The expression level of SENP1 mRNA was measured in in six platinum-sensitive and resistant ovarian cancer cell lines, including SKOV3 WT, SKOV3 CR, IGROV1 WT, IGROV1 CR, A2780 WT, A2780 CR, PEO1, PEO4, PEO14, PEO23, OV90 WT and OV90 CR. Significantly, all cisplatin resistant cells exhibited 2.8-4-fold increase of SENP1 mRNA levels compared to their sensitive counterparts (FIG. 4C). Consistently, the protein levels of SENP1 were also upregulated in platinum-resistant ovarian cancer cells, in which SUMOylation of JAK2 was decreased correspondingly (FIGS. 4D and 4E).

Figure 4F:
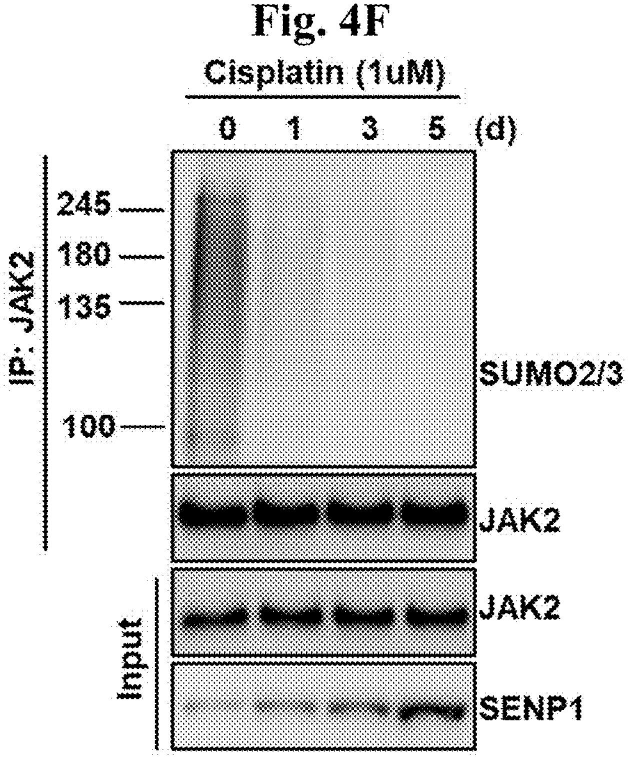
Figure 4G:
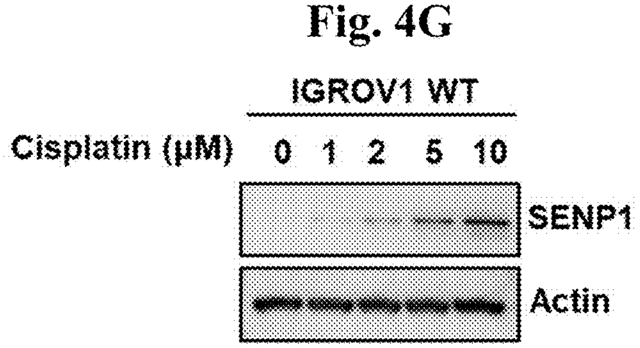
Figures 4H, 4I, 4J:
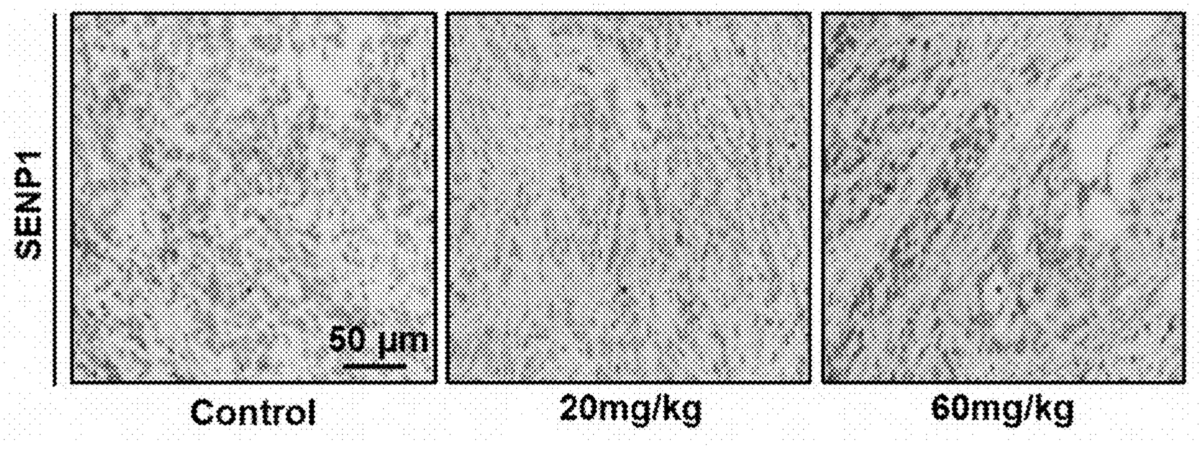
Figure 4K:
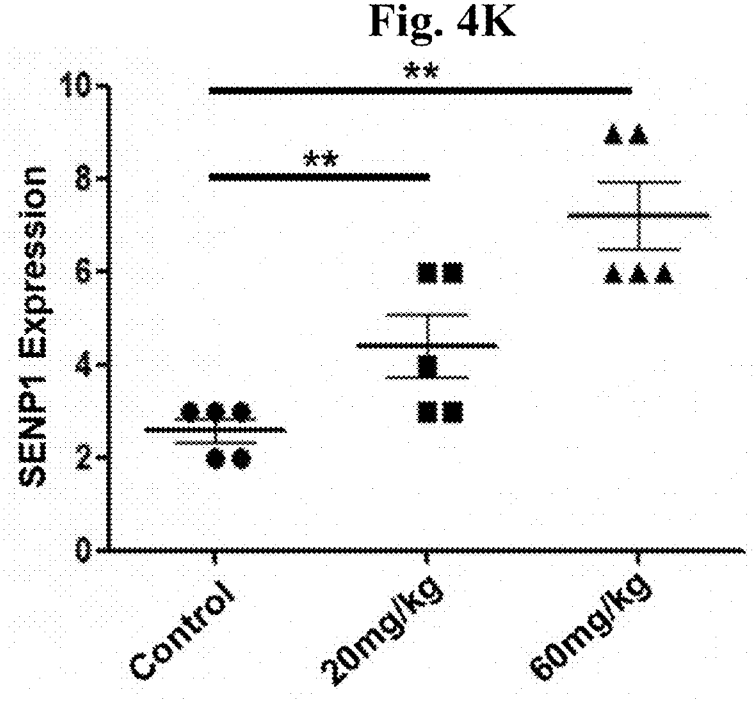

The SENP1 protein level was increased while JAK2 SUMOylation was decreased correspondingly in IGROV1 cells treated with cisplatin in a time and dose dependent manner (FIGS. 4F and 4G). To further test the SENP1 induction by platinum drugs in vivo, SENP1 protein levels were measured in IGROV1 xenograft tumors using immunohistochemistry (IHC) in implanted immunodeficient nude mice that were treated with carboplatin at 20 mg/kg or 60 mg/kg after tumor was developed. Carboplatin-treated ovarian tumors exhibited a significant increase of SENP1 expression (FIGS. 4H-4K). These results confirmed that SENP1 expression was increased in response to platinum drug treatment in ovarian cancer cells as disclosed.

Figure 5A:
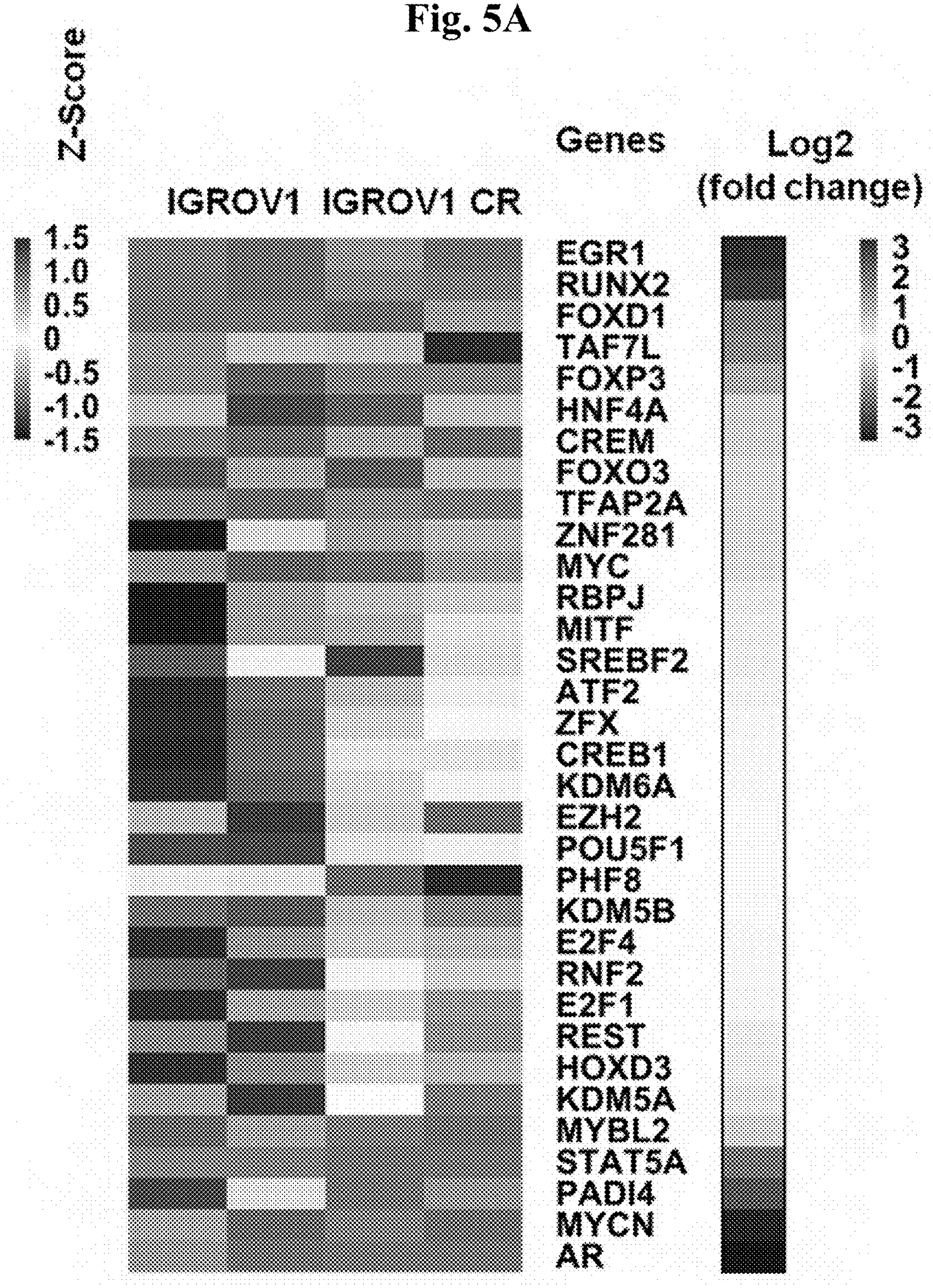
FIGS. 5A-5E depict images illustrating transcription factor RUNX2 regulation of SENP1 expression in cisplatin-resistant ovarian cancer cells.
Figure 5B:
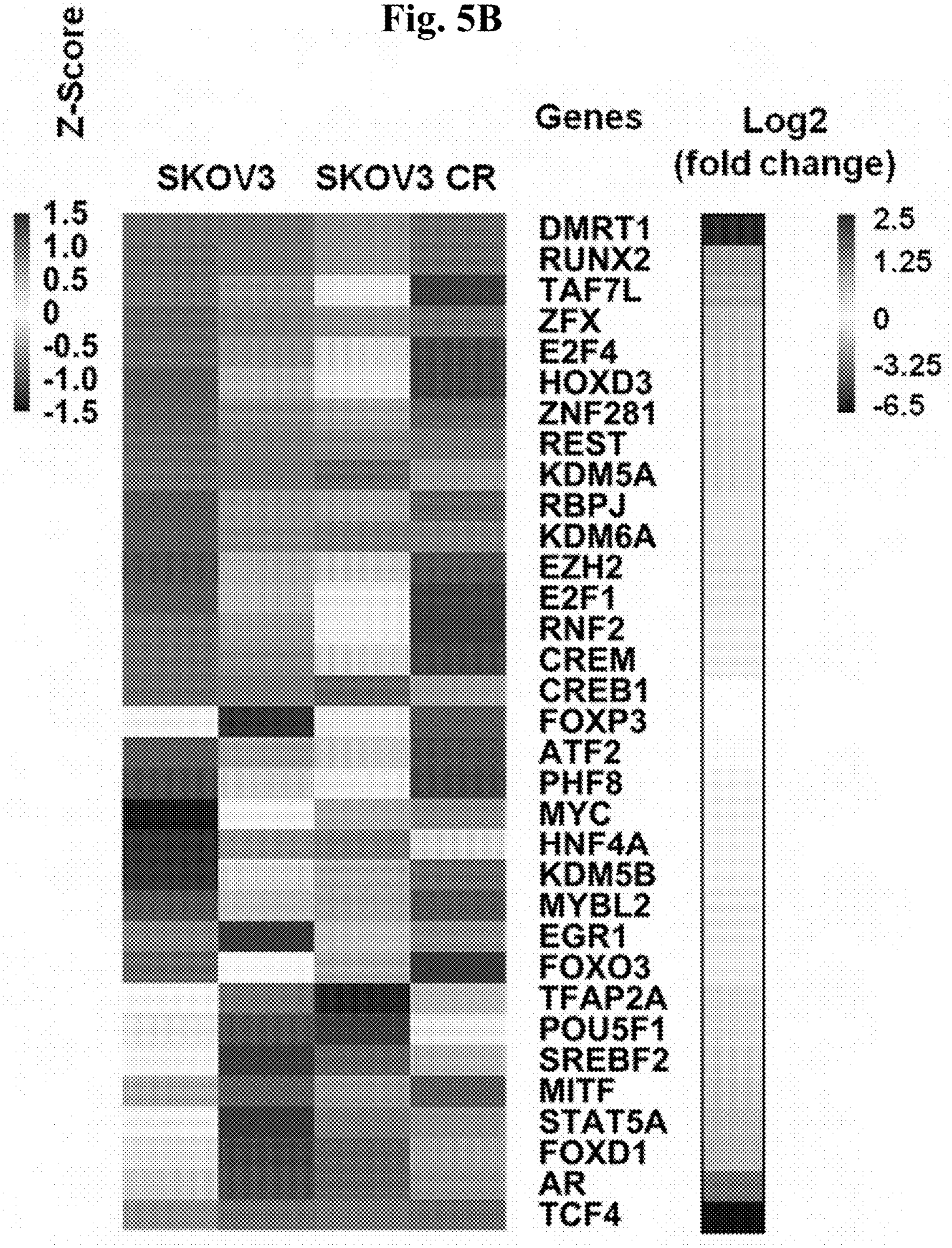
Figure 5C:
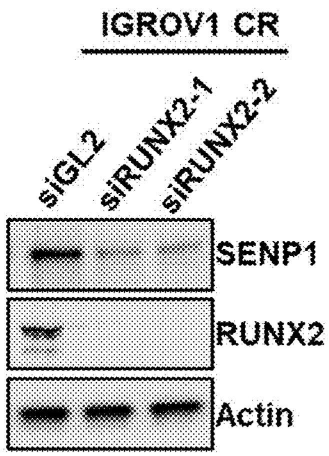
Figure 5D:
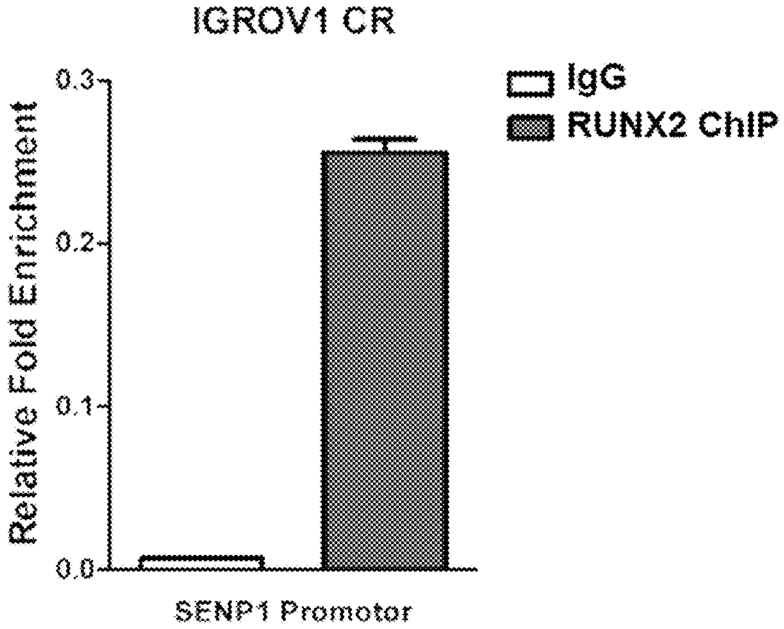
Figure 5E:
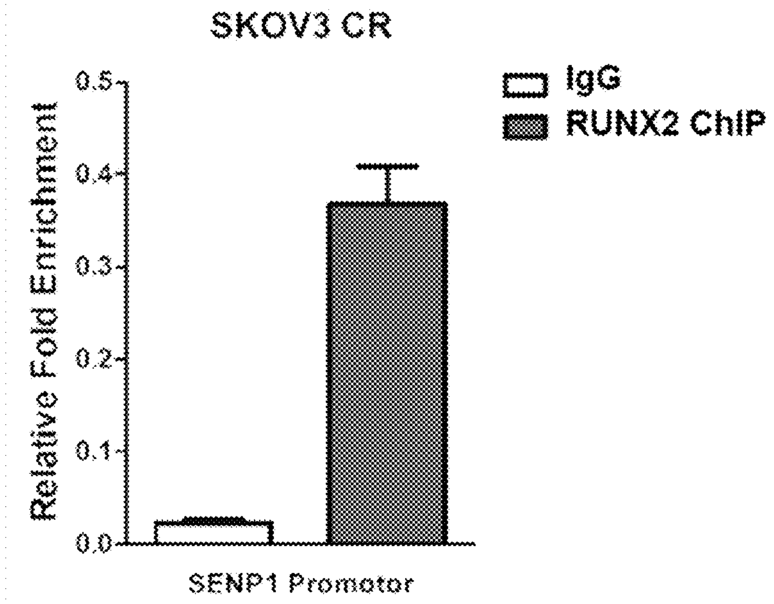

Having found that SENP1 mRNA level was upregulated in cisplatin resistant cell lines as compared to that in their sensitive counterparts (FIG. 4C), it was next investigated how SENP1 mRNA was regulated. First, all transcription factors (TF) that target promotor region of SENP1 were identified from the Harmonize database (Rouillard et al., Database (Oxford). 2016 Jul. 3; 2016. pii: baw100). Comparing the mRNA level of these TFs with RNA sequencing data (FIGS. 5A and 5B), RUNX2 had mRNA levels significantly increased in both resistant cell lines. Significantly, depletion of RUNX2 reduced SENP1 expression in IGROV1 CR cells (FIG. 5C). To explore whether RUNX2 binds to SENP1 promoter region in ovarian cancer cells, a ChIP assay was performed with control IgG or RUNX2 antibody. The ChIP analysis showed that RUNX2 was enriched at promotor region of SENP1 but not at a negative region of SENP1 promotor, indicating that RUNX2 accumulates at SENP1 promotor in both IGROV1 CR and SKOV3 CR cells (FIGS. 5D and 5E). Taken together, these results indicated that transcription factor RUNX2 regulated SENP1 expression in cisplatin-resistant ovarian cancer cells.

Figure 6A:
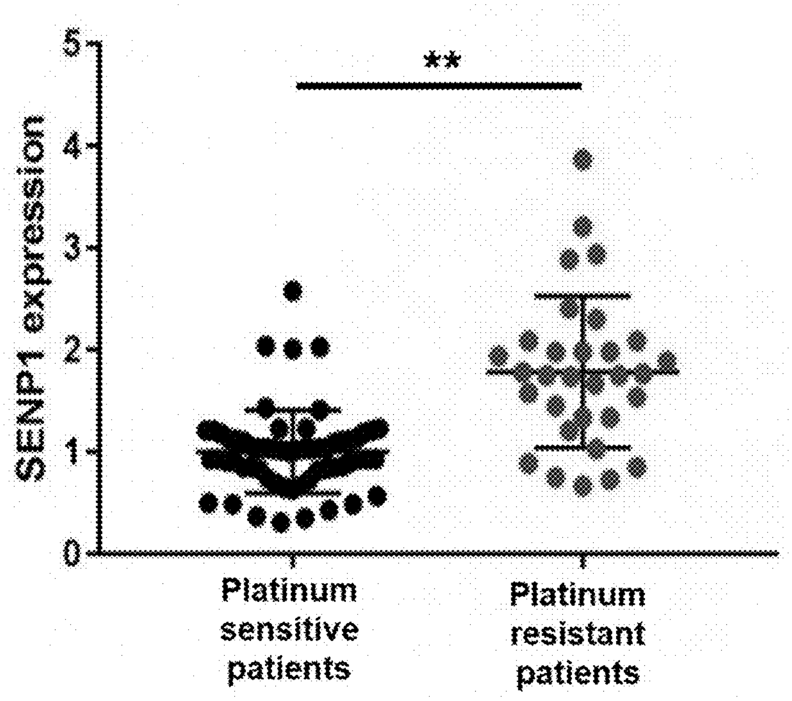
FIGS. 6A-6K depict images illustrating clinical evidence of activated SENP1/JAK2 activity in platinum-resistant ovarian cancer patients.
Figure 6B:
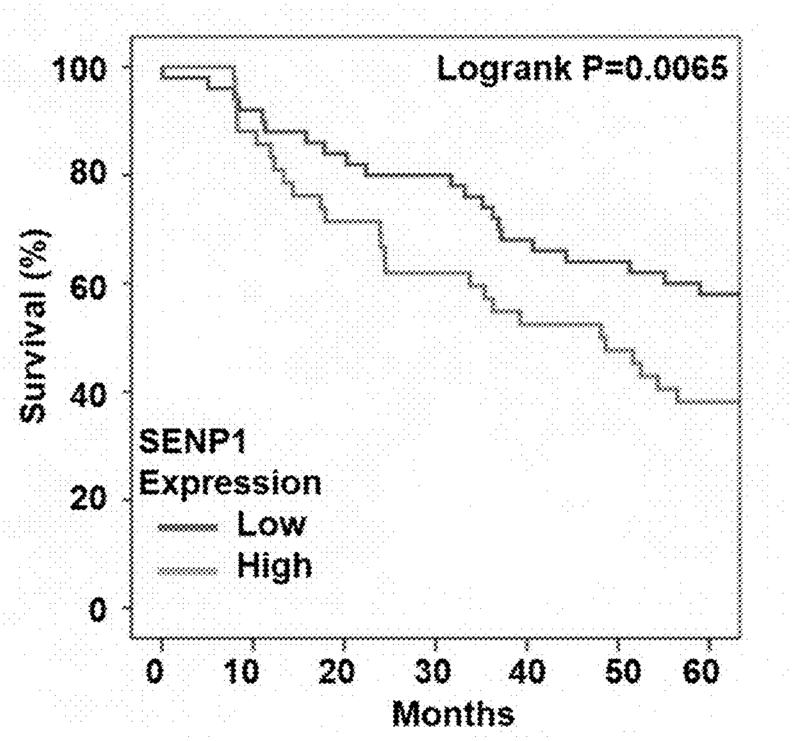
Figure 6C:
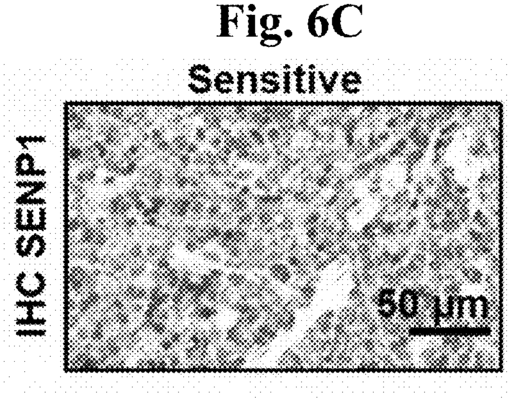
Figure 6D:
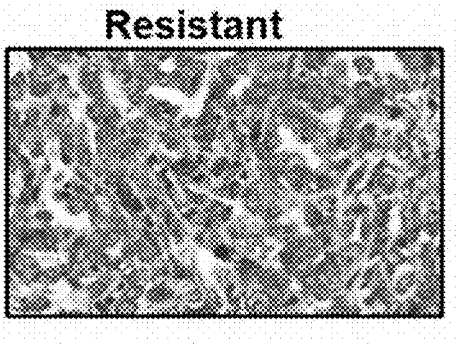
Figure 6E:
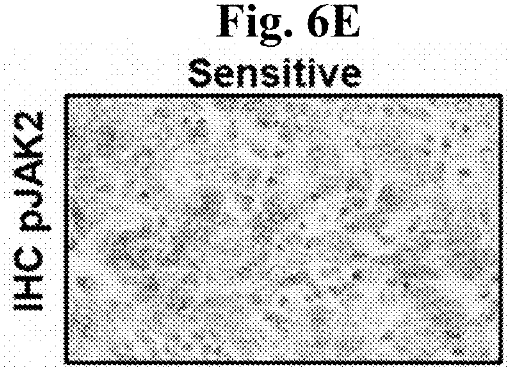
Figure 6F:
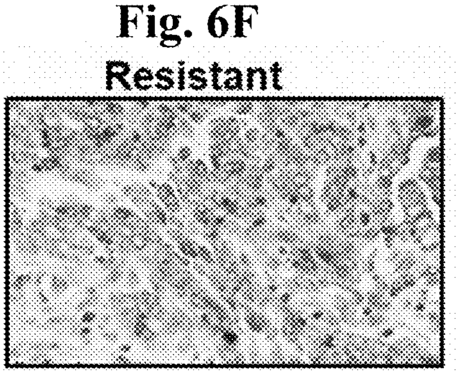
Figure 6G:
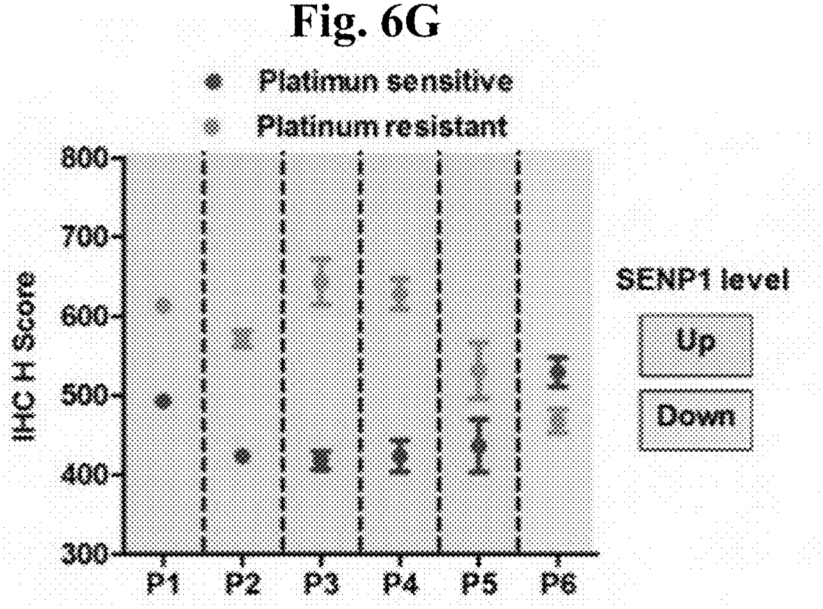
Figure 6H:
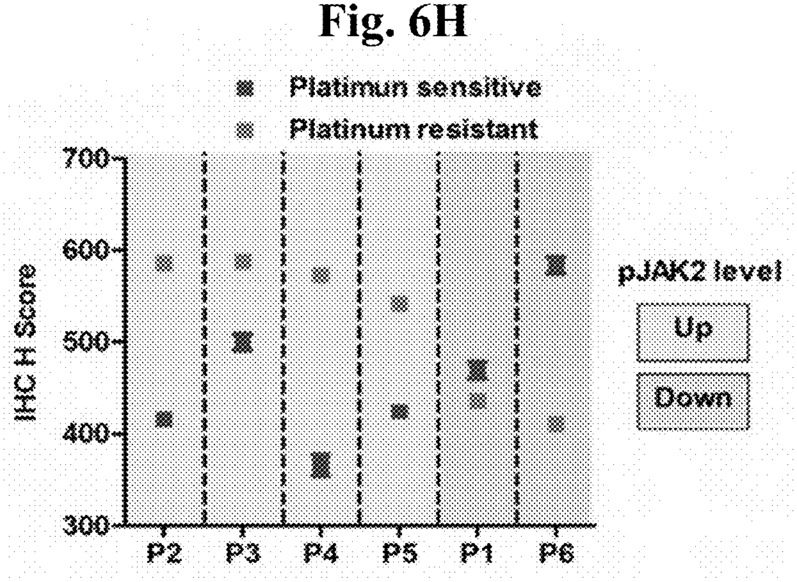
Figure 6I:
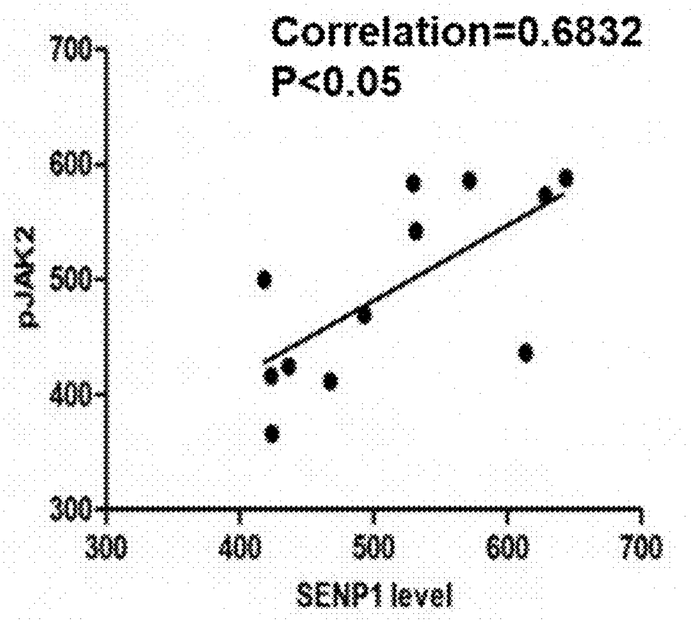

Example 5. Clinical Evidence of Activated SENP1/JAK2 Signaling in Platinum-Resistant Ovarian Cancer Patients To further confirm the role of SENP1 in platinum-resistance of ovarian cancer patients, SENP1 mRNA expression levels were measured from tumor samples of 61 platinum-sensitive patients and 32 platinum-resistant patients. SENP1 mRNA levels were significantly increased in platinum-resistant patients (FIG. 6A). Significantly, the patients with higher SENP1 mRNA expression levels exhibited worse prognosis in terms of overall survival as compared to the patients with lower SENP1 mRNA level (FIG. 6B). To directly evaluate protein expression change caused by chemotherapy, SENP1 protein expression levels were also measured in the samples from the same patients before platinum drug treatment and after acquired drug resistance. Strikingly, 5 out of 6 patients showed upregulated SENP1 protein level after development of platinum drug resistance (FIGS. 6C-6H). There was a good correlation between SENP1 and phosphorylated JAK2 levels in the tested sensitive and resistant patient tumor samples (FIG. 6I), indicating SENP1 upregulation was correlated with JAK2-mediated platinum-resistance in ovarian cancer.

Figure 6J:
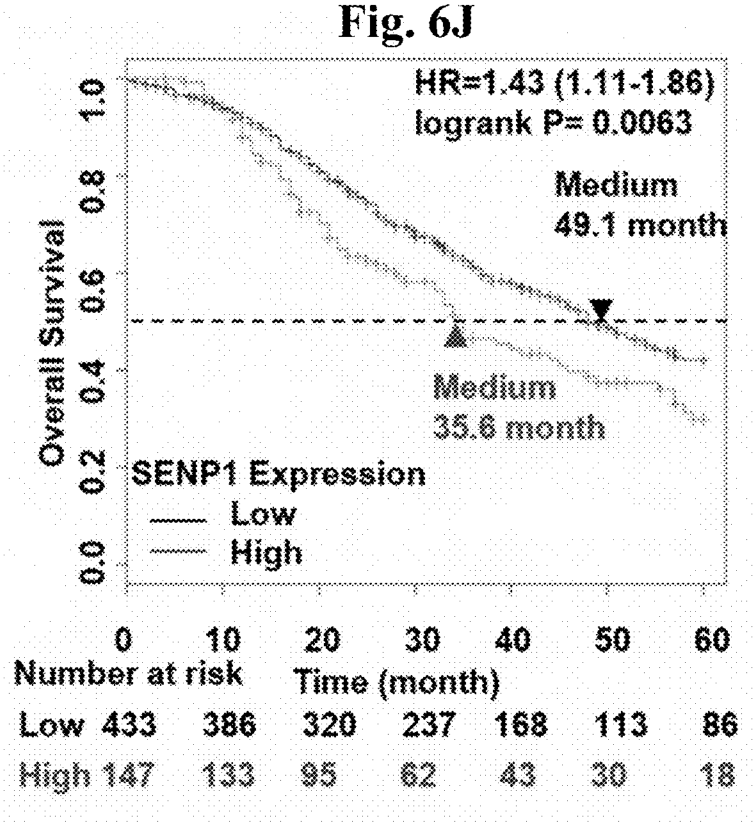
Figure 6K:
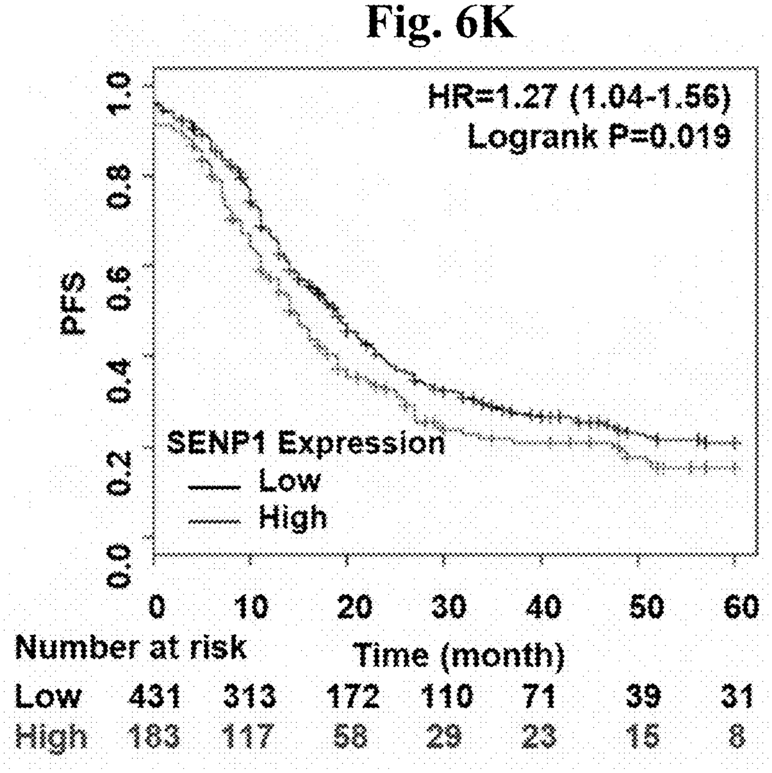

The correlation of survival rate with the SENP1 expression from patients who had platinum drug treatment history from ovarian cancer was analyzed. Patients with high expression level of SENP1 exhibited a poor prognosis of overall survival and progression free survival (FIGS. 6J and 6K). Thus, a higher level of SENP1 was highly correlated with worse ovarian cancer patient survival following platinum drug-based therapy.

Figure 7A:
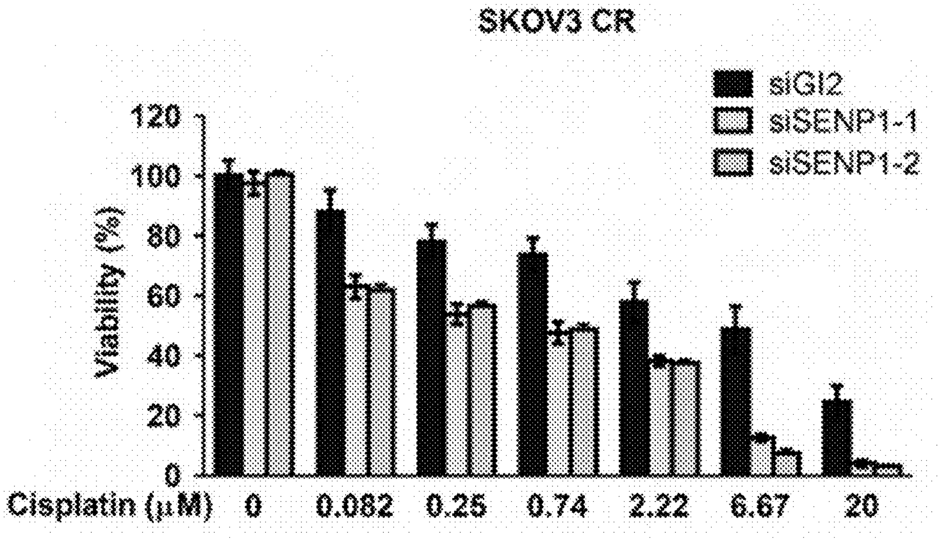
FIGS. 7A-7D depict images illustrating the SENP1/JAK2 axis as critical for cisplatin resistance in ovarian cancer cells.
Figure 7B:
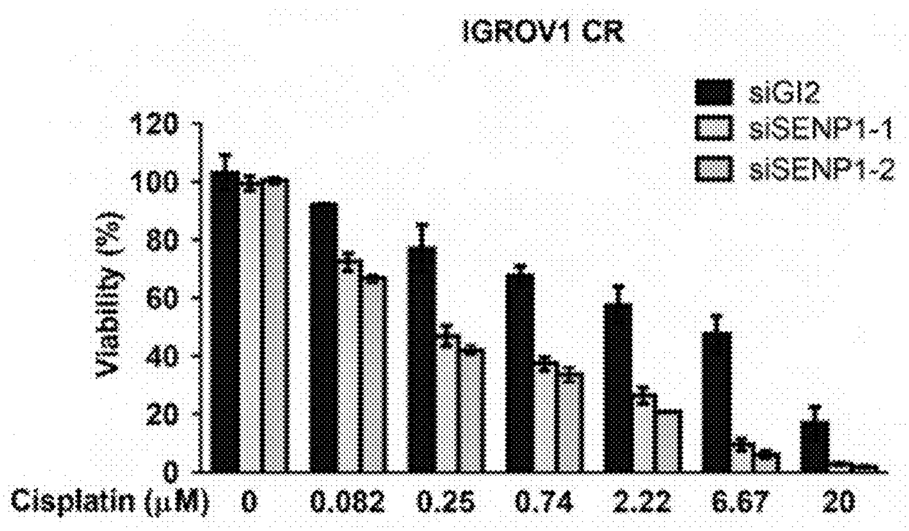
Figure 7C:
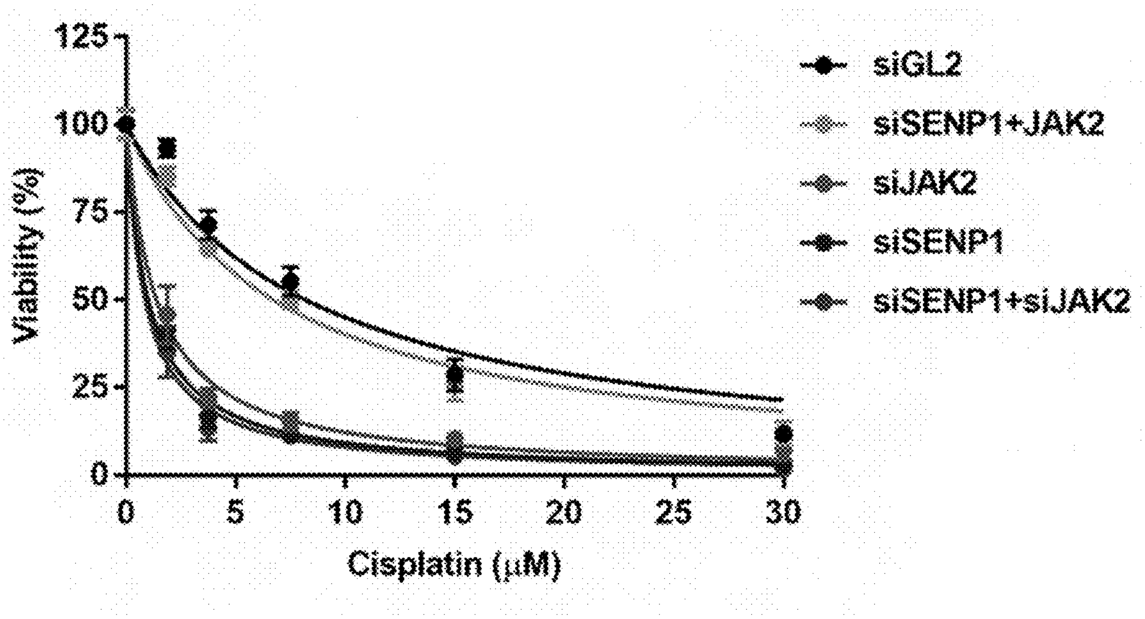
Figure 7D:
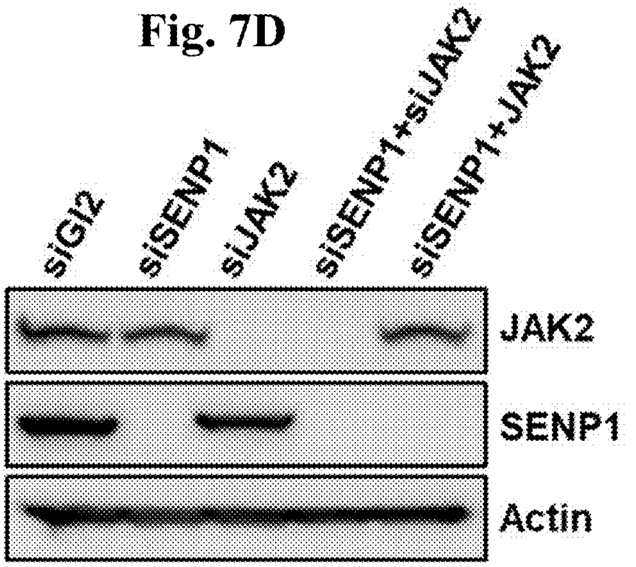

To test whether SENP1 contributes to cisplatin-resistance in ovarian cancer cells, SENP1 was depleted by two independent siRNAs. SENP1 depletion significantly increased the cell sensitivity to cisplatin in both SKOV3 CR and IGROV1 CR cells (FIGS. 7A and 7B). To confirm that JAK2 was the primary target of SENP1 to promote platinum-resistance, the sensitivity of IGROV1 CR cells to cisplatin was examined using genetic analyses. As shown in FIGS. 7C and 7D, cells with depletion of either SENP1 or JAK2 exhibited the similar reduced sensitivity to cisplatin, and co-depletion of SENP1 and JAK2 did not further increase the sensitivity of IGROV1 CR cells to cisplatin compared to depletion of SENP1 or JAK2 alone, indicating that SENP1 and JAK2 functioned in the same pathway. Ectopical expression of JAK2 in IGROV1 CR cells with depleted SENP1 restored cisplatin resistance of IGROV1 CR cells to the similar levels as cells treated with control siGL2, suggested that JAK2 was the primary target of SENP1 to promote platinum-resistance in ovarian cancer cells.

Example 6. Identification of a Novel Potent SENP1 Inhibitor UA

Figure 8A:
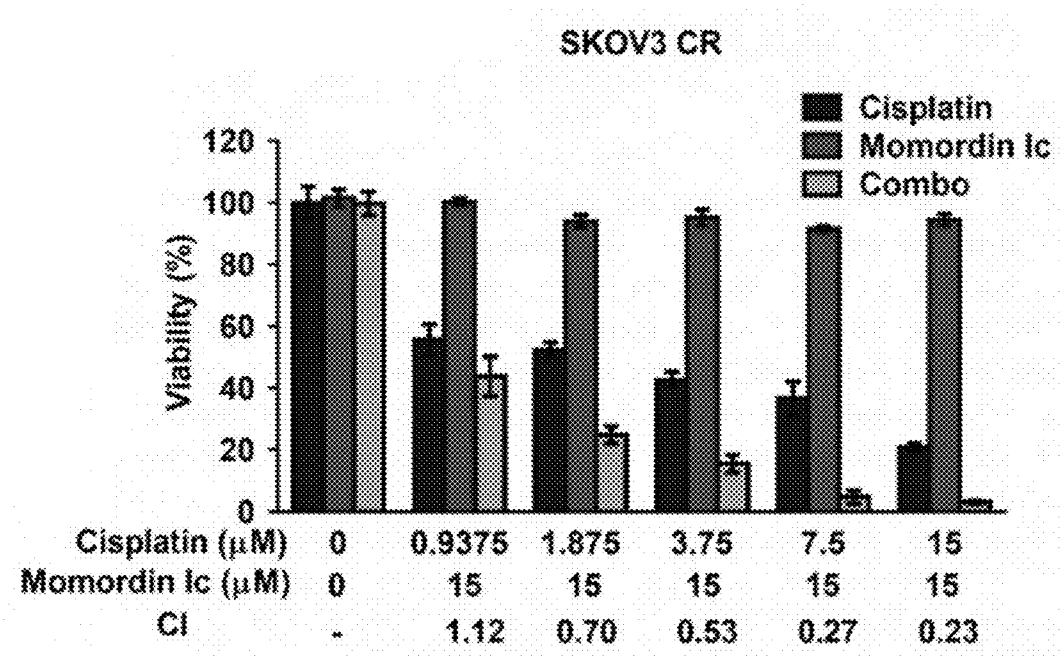
FIGS. 8A-8E depict images illustrating that inhibition of SENP1 by Mc re-sensitized cisplatin-resistant ovarian cancer cells.
Figure 8B:
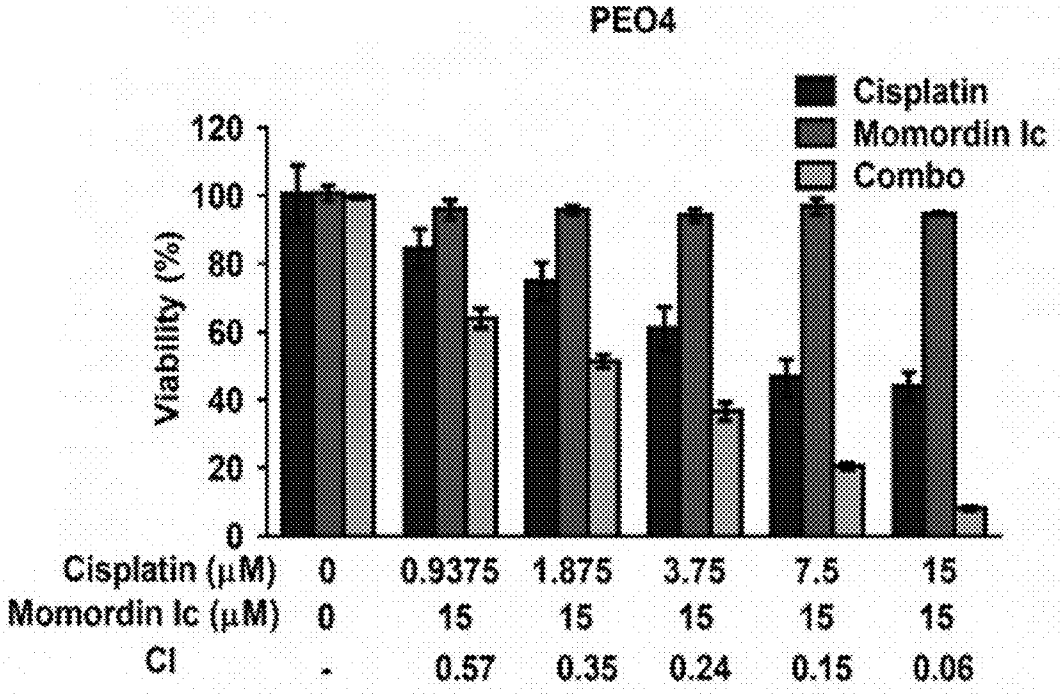
Figure 8C:
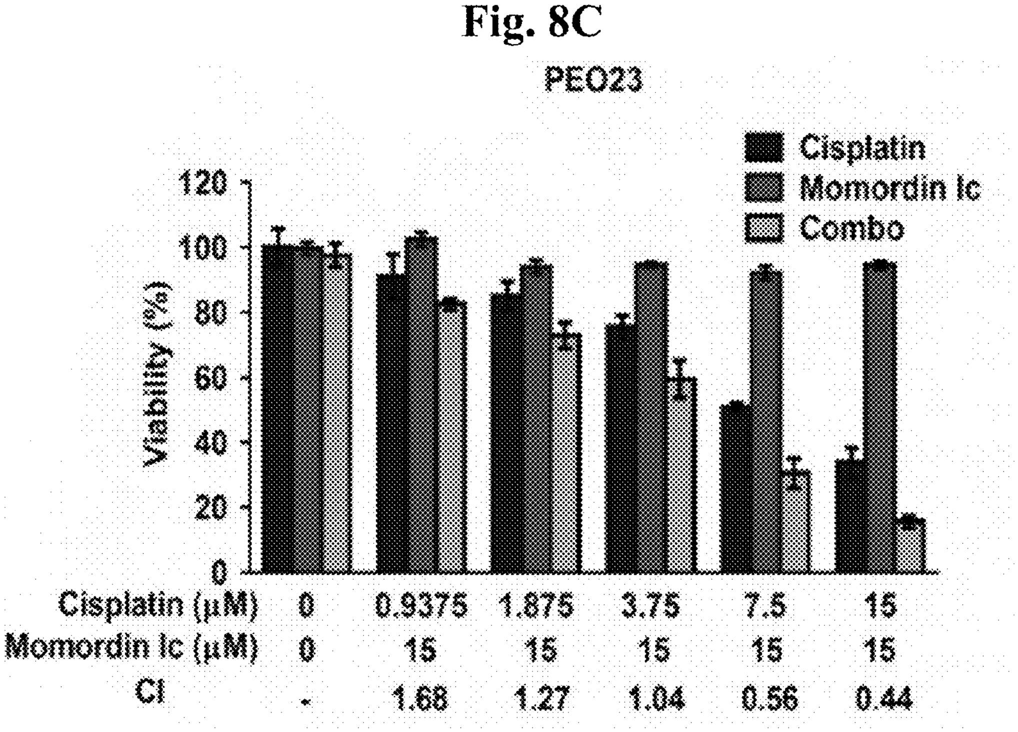
Figure 8D:
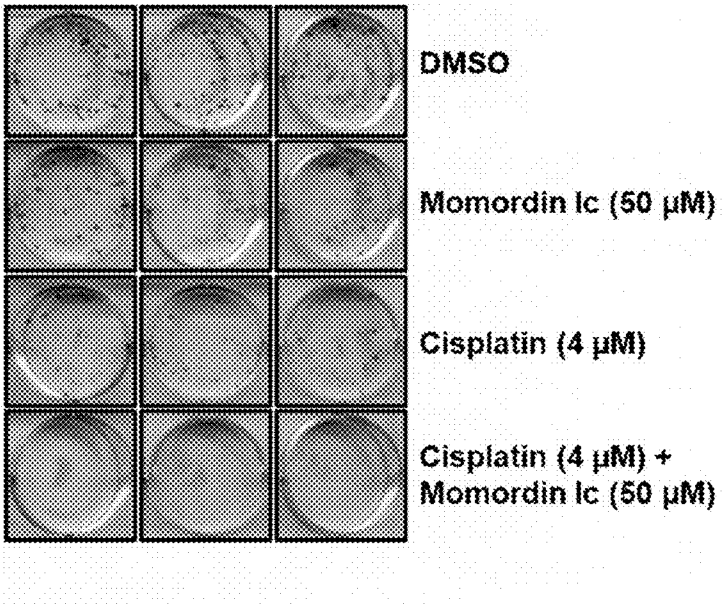
Figure 8E:
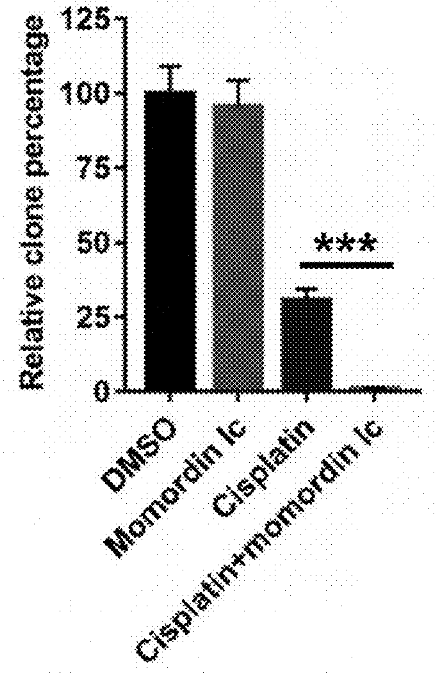

Momordin Ic (Mc) is a natural pentacyclic triterpenoid compound. SKOV3 CR, PEO4 and PEO23 cells were treated with Mc. SENP1 activity was inhibited with $IC_{50}$ at 15.37 μM in vitro. Inhibition of SENP1 by Mc re-sensitized SKOV3 CR, PEO4 and PEO23 cells to cisplatin (FIGS. 8A-8C). Significantly, Mc exhibited synergy with cisplatin to inhibit cell proliferation of resistant cells, as indicated by combination index (CI) (synergism: CI<1; additive effect: CI=1; and antagonism: CI>1). Using clonogenic survival assay, Mc showed a similar synergy with cisplatin in IGROV1 CR (FIGS. 8D and 8E).

Figure 9A:
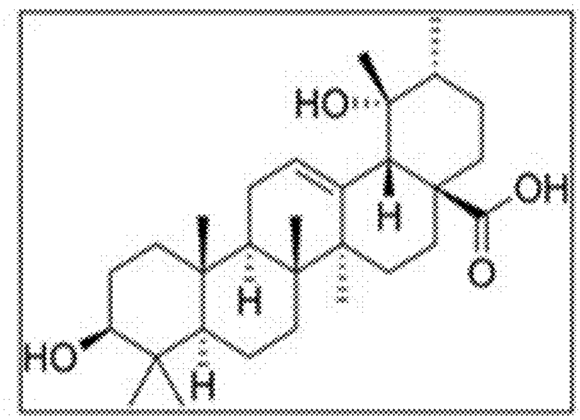
FIGS. 9A-9E depict images illustrating ursolic acid derivatives inhibiting SENP1 enzymatic activity.
Figure 9B:
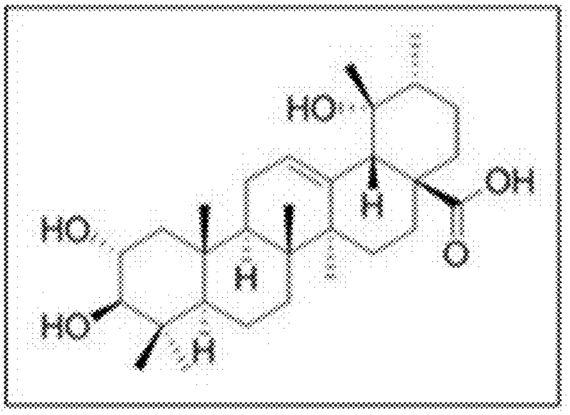
Figure 9C:
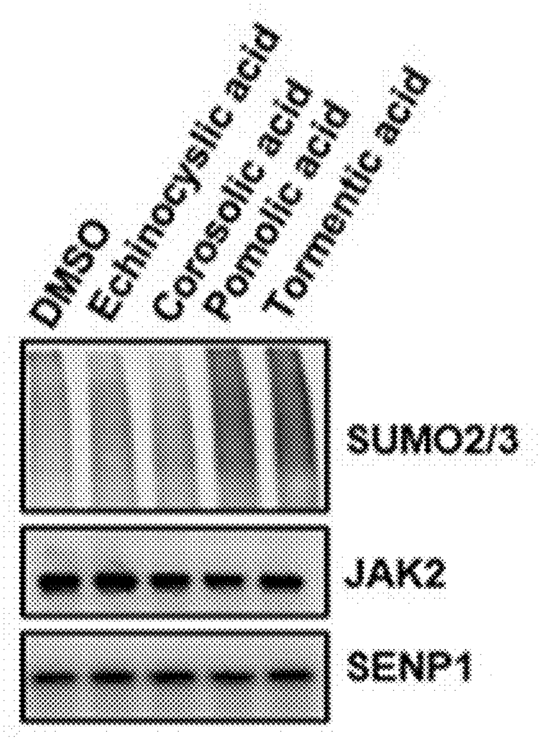
Figures 9D, 9E:
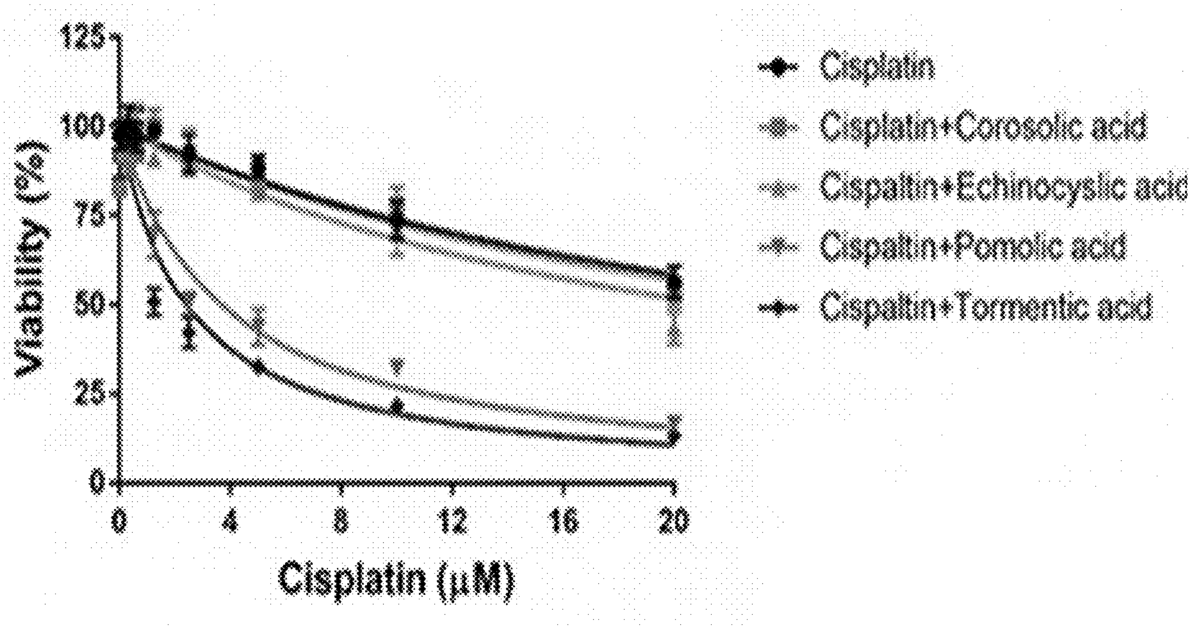

In addition to Mc, two other natural compounds, pomolic acid (FIG. 9A) and tormentic acid (FIG. 9B) were used to SENP1 activity in vitro. Specifically, recombinant His-JAK2 was SUMOylated then incubated with recombinant GST-SENP1 together with pomolic acid or tormentic acid for 3 hours. Immunoprecipitations were then subjected to Western blot (FIG. 9C). The synergistic effects of cisplatin and echinocyslic acid, corosolicin acid, pomolic acid or tormentic acid was observed in SKOV3 CR cells (FIG. 9D). FIG. 9E shows the $IC_{50}$s of cisplatin in each combination in FIG. 9D were indicated. Data were represented as mean±SD (n=3).

Figure 10:
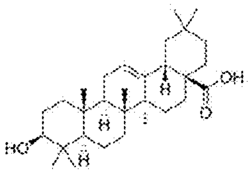
FIG. 10 depicts chemical structures of Momordin Ic and its derivatives in addition to the $IC_{50}$ of Momordin Ic and its derivatives combined with 2 μM cisplatin as detected by a cell survival assay in SKOV3 CR cells.
Figure 10:
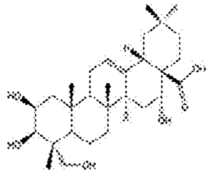
Figure 10:
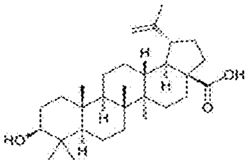
Figure 10:
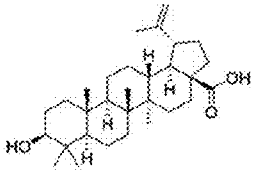
Figure 10:
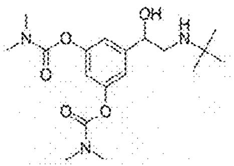
Figure 10:
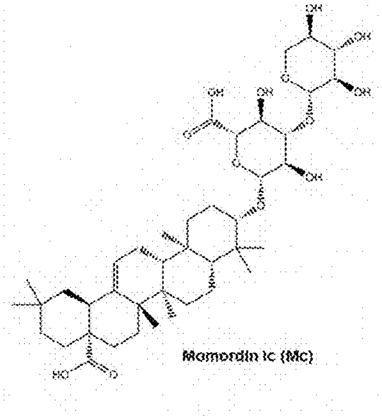
Figure 10:
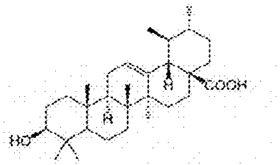
Figure 10:
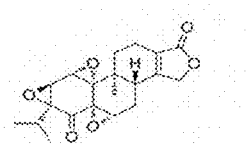
Figure 10:
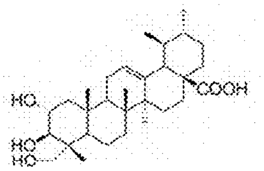
Figure 10:
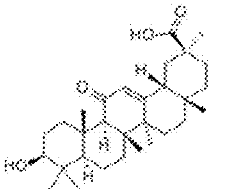
Figure 10:
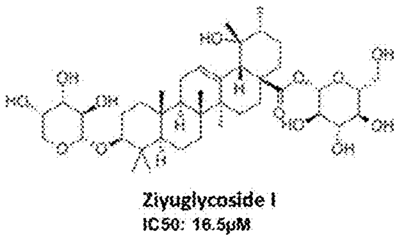
Figure 10:
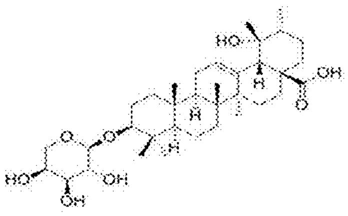
Figure 11A:
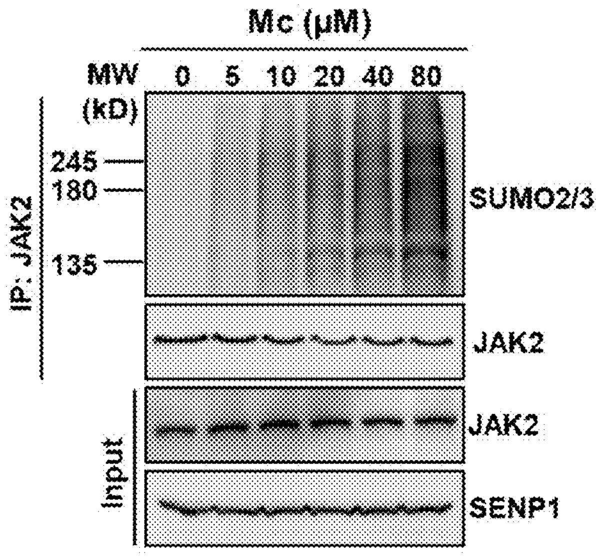
FIGS. 11A-11L depict images illustrating identification of a novel potent SENP1 inhibitor, UA.
Figure 11B:
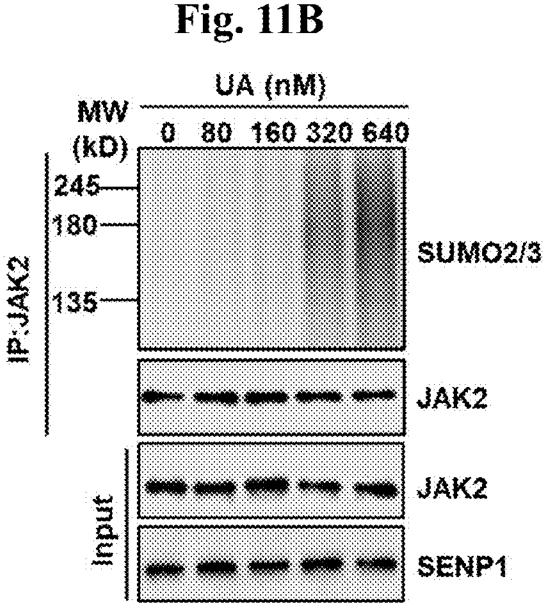
Figure 11C:
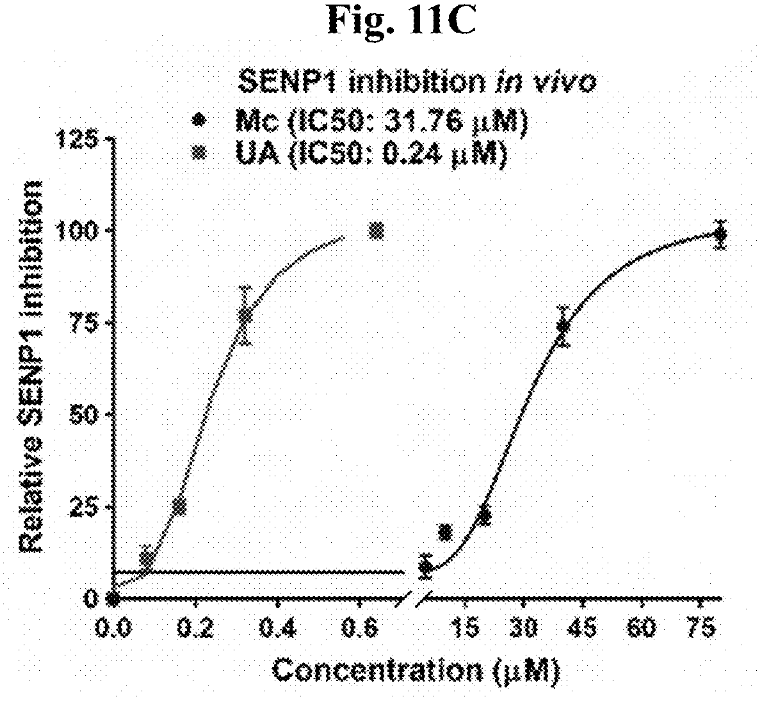
Figure 11D:
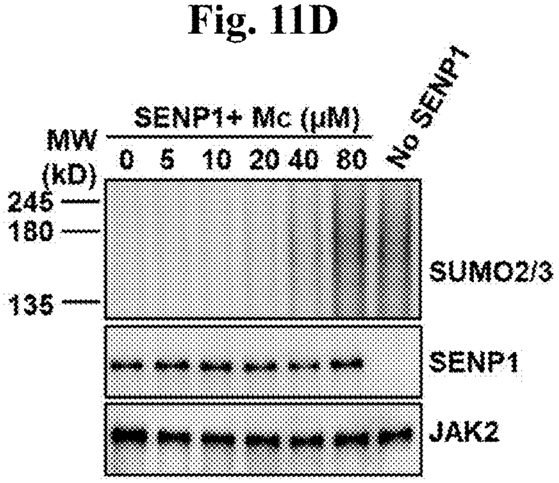
Figure 11E:
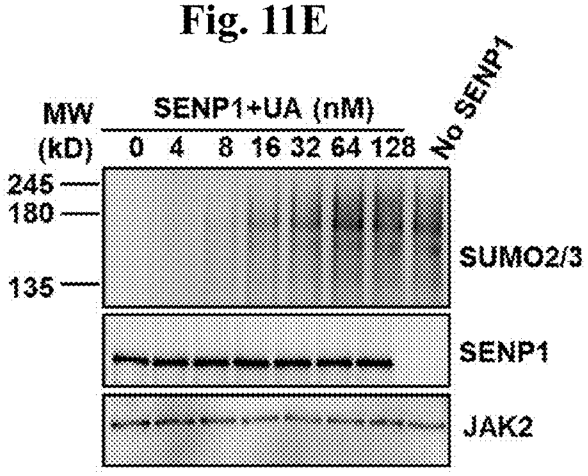
Figure 11F:
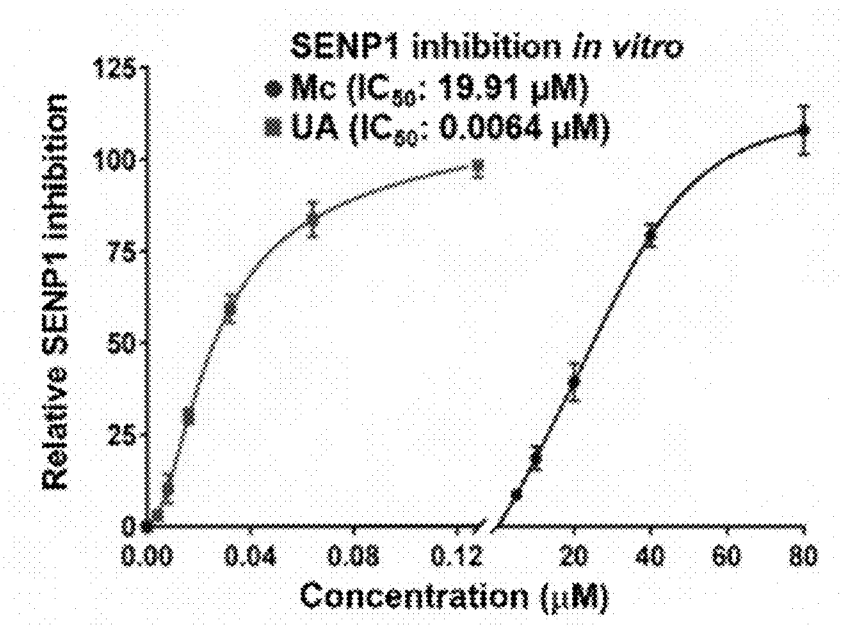

Sixteen natural compounds that have similar structure to Mc, including oleanolic acid, polygalacic acid, betulinic acid, 2,3-hydroxybetulinic acid, glycyrrhizic acid, asiatic ascid, ziyuglycoside I, ziyuglycoside II, bambuterol, ursolic acid (UA), and triptonide (FIG. 10). Significantly, UA inhibited deSUMOylation of JAK2 with $IC_{50}$ at 0.24 μM (FIGS. 11B and 11C) compared to Mc with $IC_{50}$ at 31.76 μM in IGROV1 cells (FIGS. 11A and 11C). Strikingly, UA exhibited 3000-fold more potency to inhibit deSUMOylation of His-JAK2 in vitro (UA $IC_{50}$ at 0.0064 μM) (FIGS. 11E and 11F) than Mc ($IC_{50}$ at 19.91 μM) (FIGS. 11D and 11F).

Figure 11G:
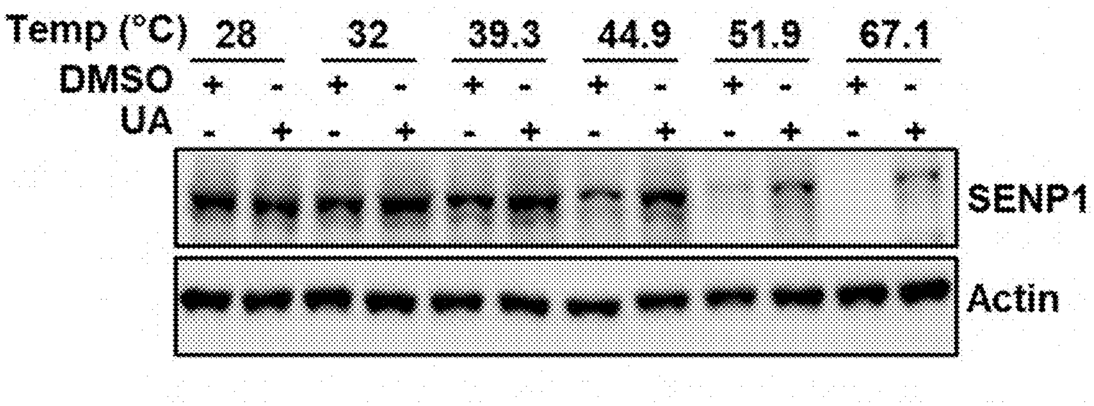
Figure 11H:
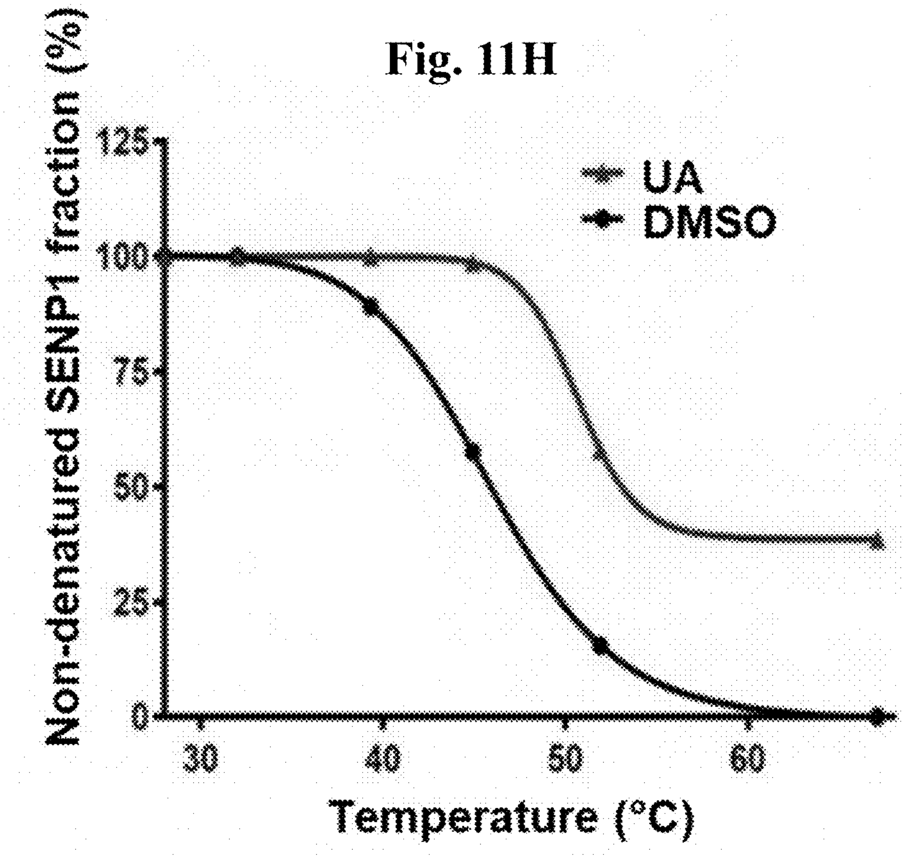
Figure 11I:
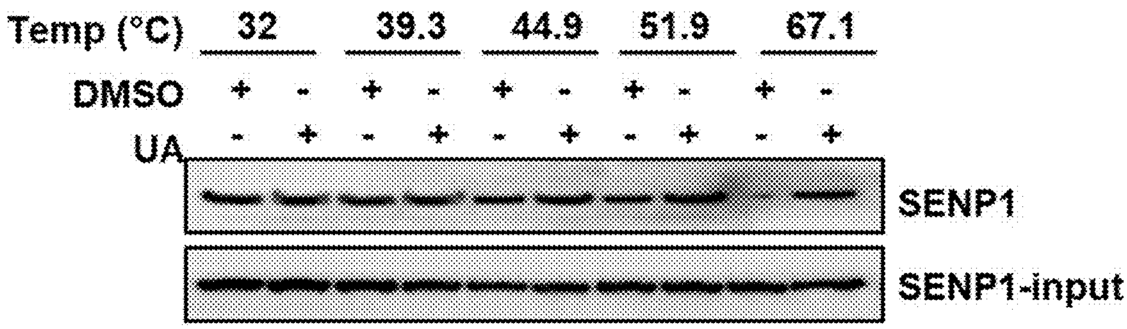
Figure 11J:
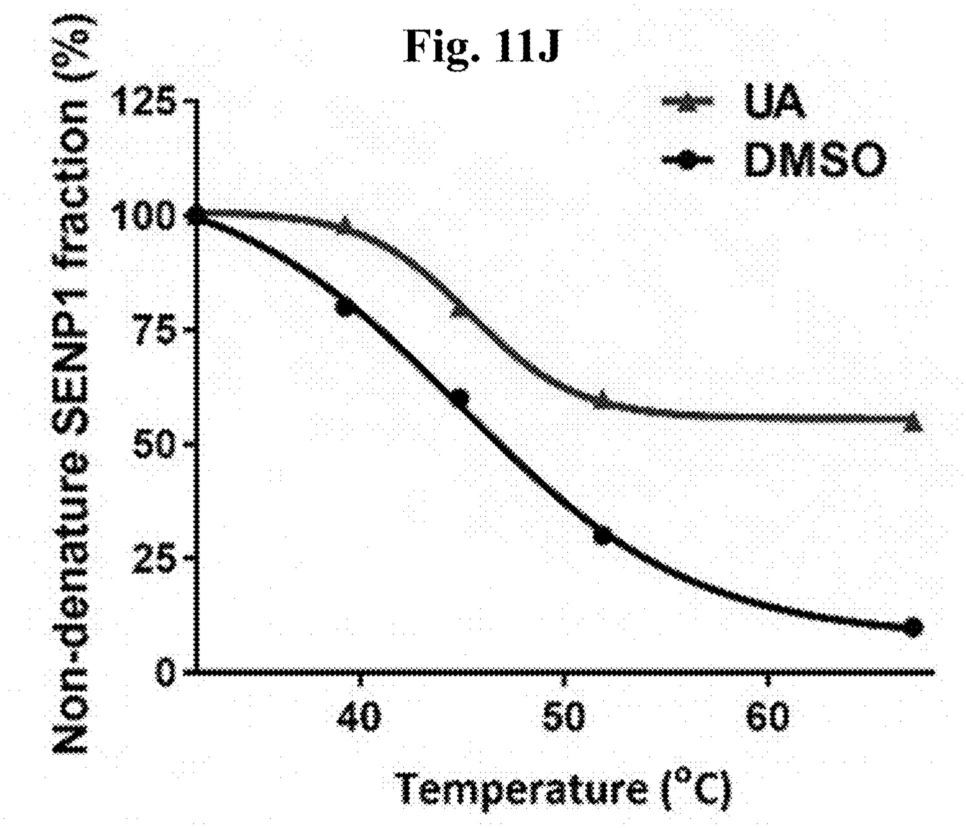
Figure 11K:
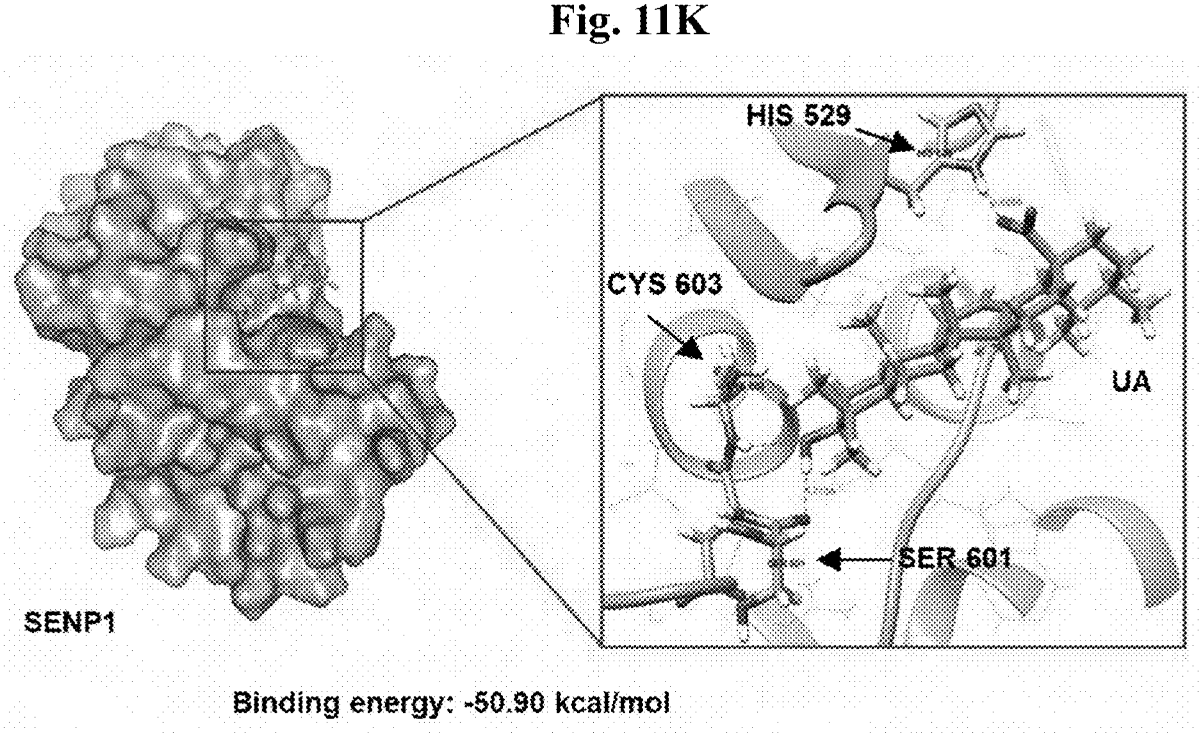
Figure 11L:
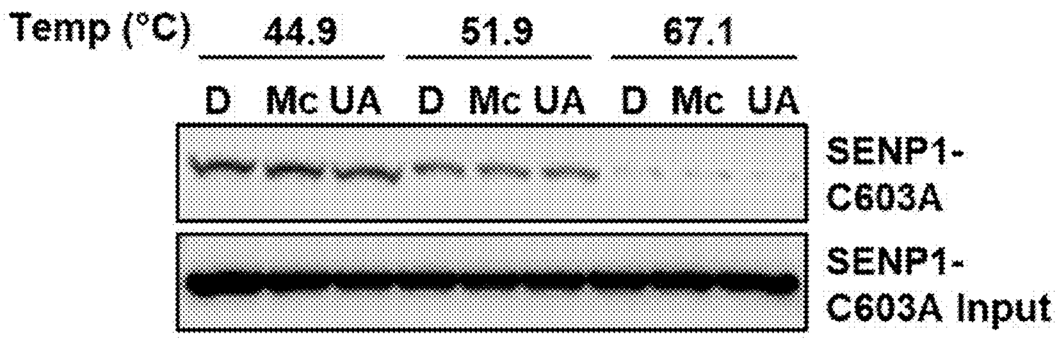

To determine whether UA binds to SENP1 directly, cellular thermal shift assays were performed in which a small molecule binds to a protein resulting in thermal stabilization of the protein. Using this assay, with was found that at higher temperature SENP1 protein was stabilized upon treatment with UA compared to control DMSO treatment in IGROV1 cells (FIGS. 11G and 11H). Consistently, UA also stabilized the recombinant SENP1 proteins (FIGS. 11I and 11J), suggesting a direct interaction between UA and SENP1. Using protein-ligand docking software Glide (Schrödinger), three specified binding sites were identified for both Mc and UA on SENP1 (H529, 5601 and C603) (FIG. 11K). The interactions of UA and Mc were next examined the with purified mutant SENP1-C603A using the thermal shift assay and found that both UA and Mc no longer stabilized the SENP1-C603A proteins, indicating that C603 of SENP1 is critical for SENP1 to bind UA and Mc (FIG. 11L).

Figure 12A:
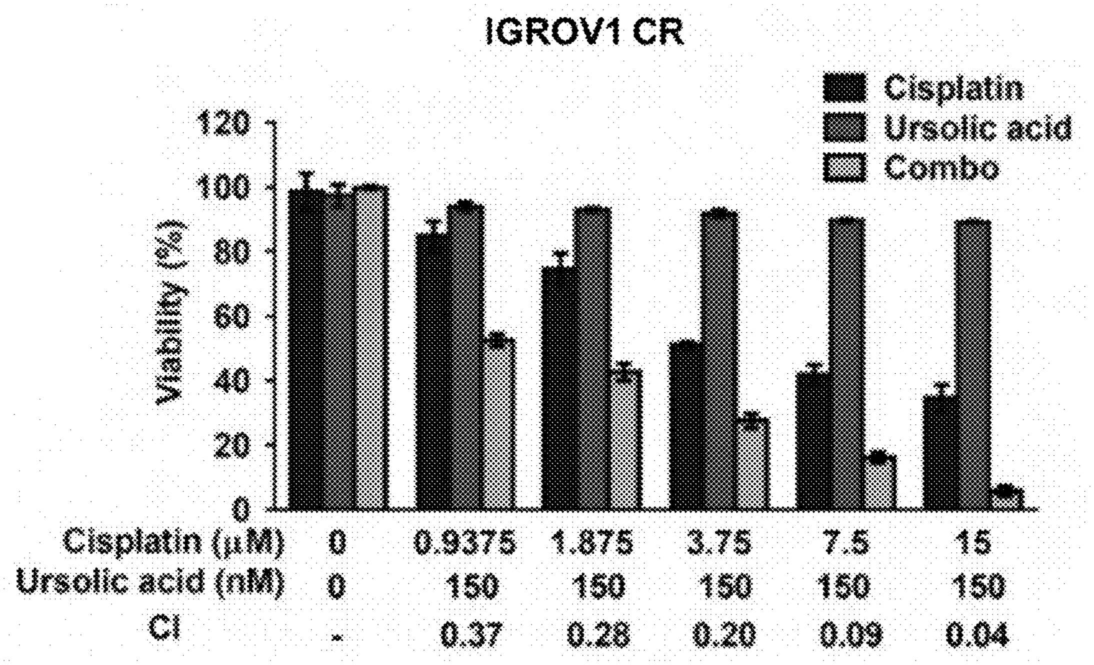
FIGS. 12A-12D depict images illustrating that inhibition of SENP1 by UA overcame cisplatin resistance in ovarian cancer.

Example 7. Inhibition of SENP1 by UA Overcomes Cisplatin Resistance in Ovarian Cancer Next it was examined whether UA had a synergistic effect with cisplatin in platinum-resistant cells. Significantly, at 150 nM, UA exhibited the great synergy with cisplatin to inhibit cell survival of IGROV1 CR cells as indicated by CI value (CI<1) (FIG. 12A).

Figure 12B:
Figure 12C:
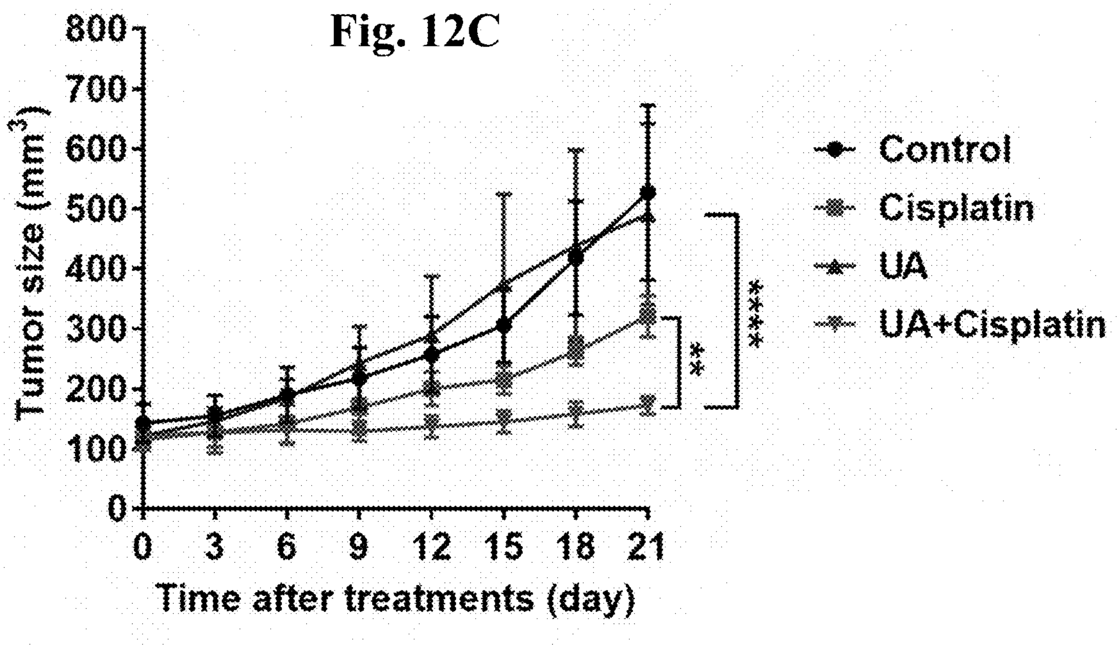
Figure 12D:
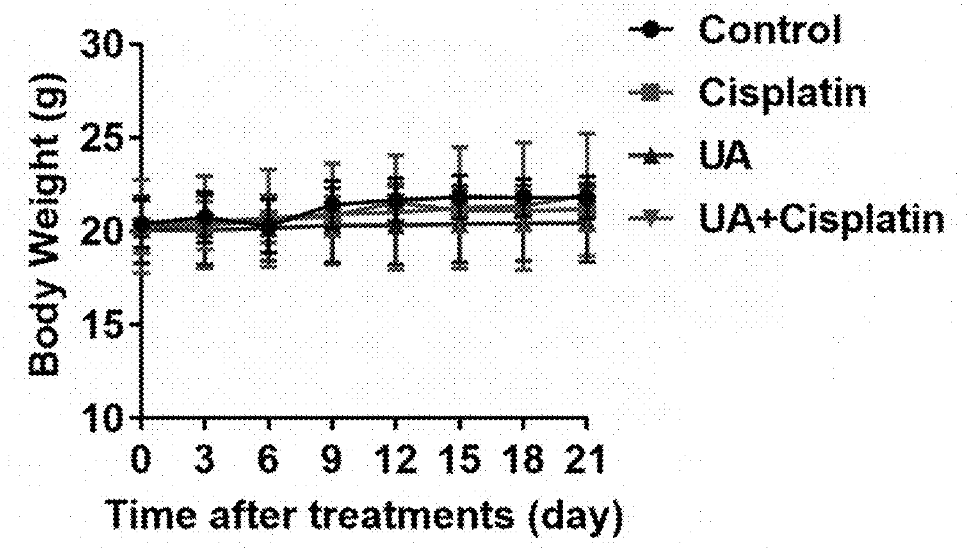
Figures 13A, 13B, 13C, 13D:
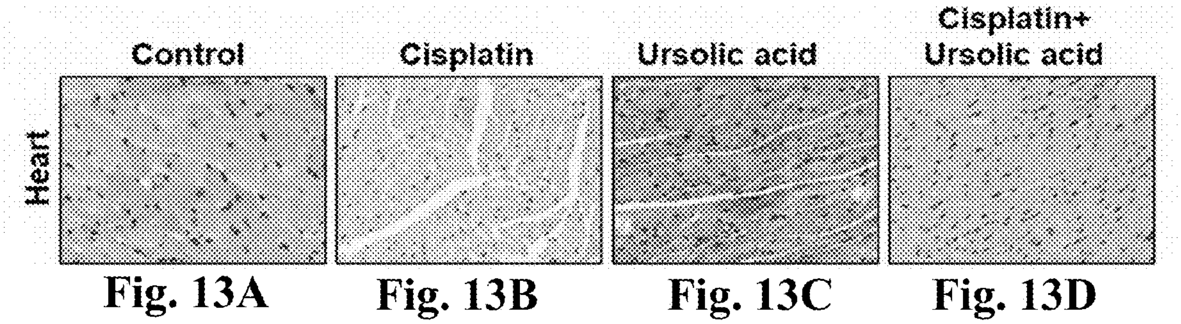
Figures 13E, 13F, 13G, 13H:
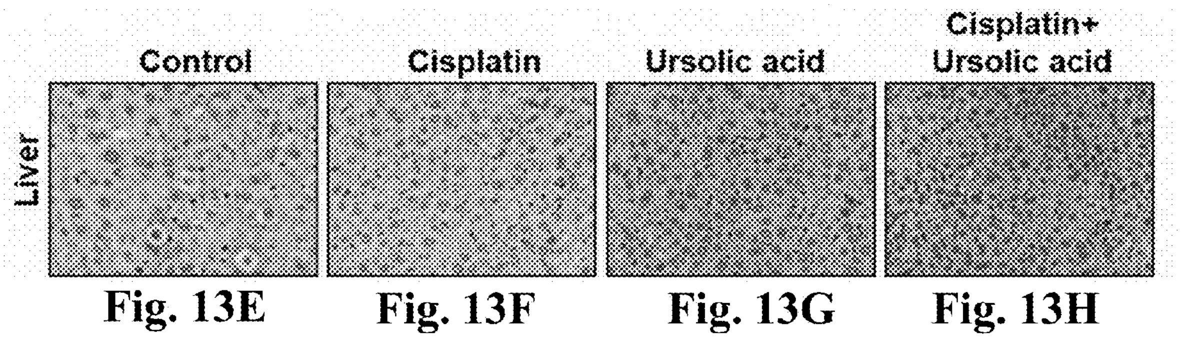
Figures 13I, 13J, 13K, 13L:
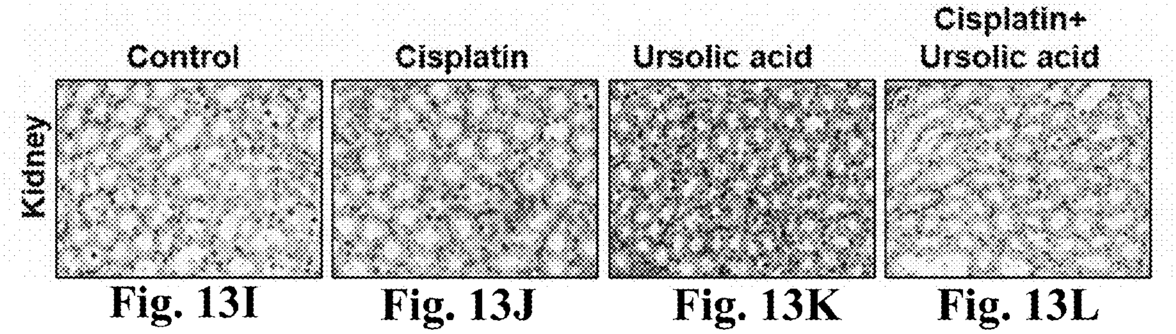
Figures 13M, 13N, 13O, 13P:
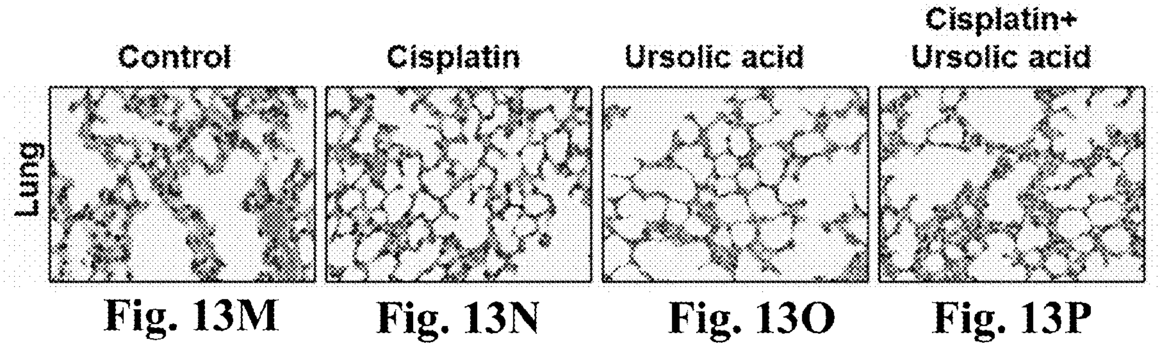

To further evaluate the therapeutic potential of UA in combination with cisplatin in vivo, IGROV1 CR cells were subcutaneously implanted into nude mice to form platinum drug resistant ovarian tumors. The mice with these tumors were then treated with UA, cisplatin, or combination of both via intraperitoneal injection. The combinational treatment with cisplatin and UA exhibited a remarkable synergy to reduce tumor growth as compared to UA or cisplatin alone (FIGS. 12B and 12C). Importantly, body weight assessment (FIG. 12D) and H&E staining of heart (FIGS. 13A-13D), liver (FIGS. 13E-13H), kidney (FIGS. 13I-13L), and lung (FIGS. 13M-13P) did not show a significant difference between these groups, indicating that combined treatment of UA and cisplatin had no systemic toxicity or side effect on these organs. IHC analysis of tumor samples (H&E staining shown in FIGS. 13Q-13T) showed that UA suppressed expression of pSTAT3 (FIGS. 13U-13Y), indicating that UA indeed targets SENP1/JAK2 signaling in vivo.

Figure 14:
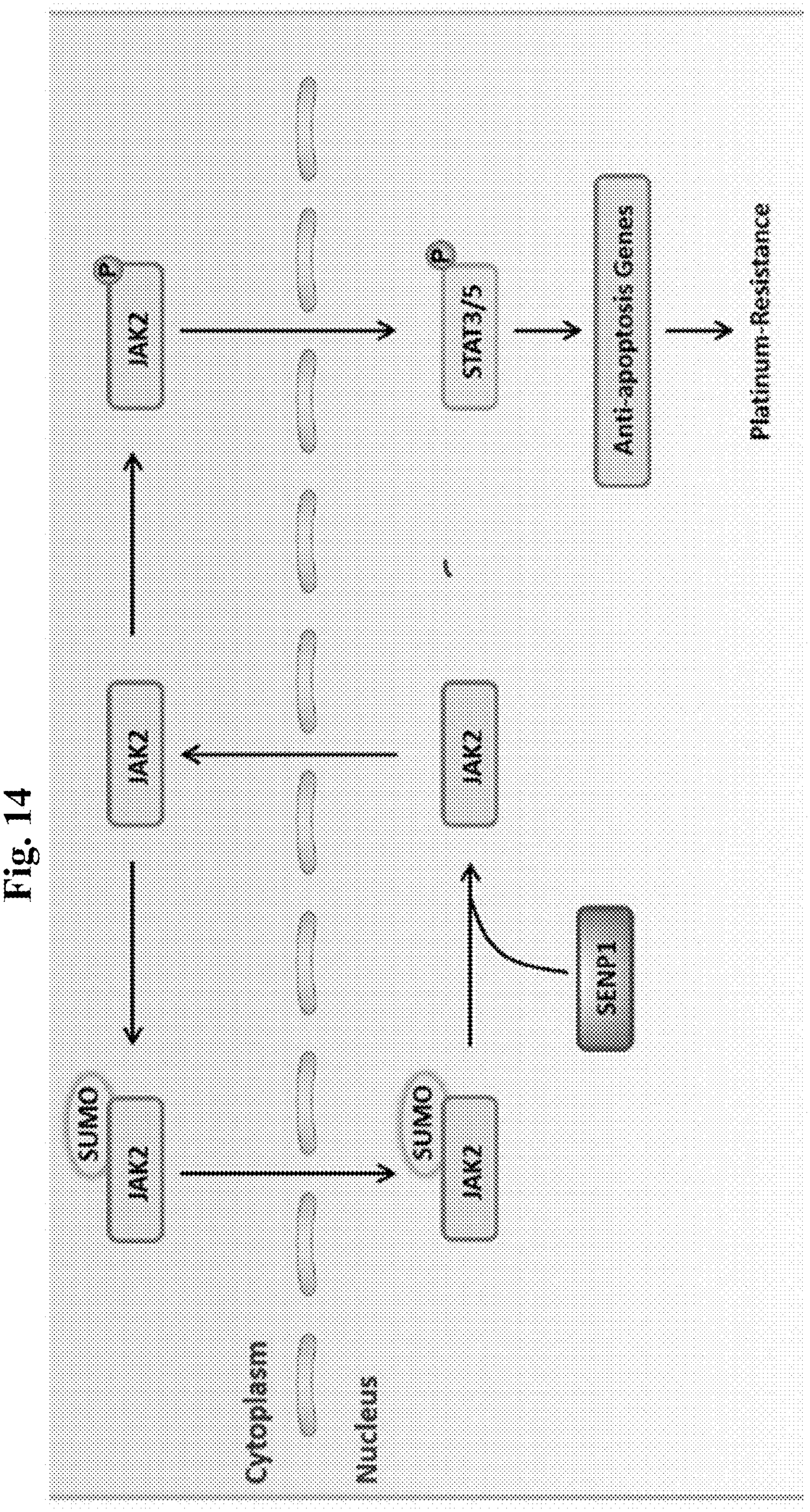
FIG. 14 depicts a schematic showing how SENP1-mediated deSUMOylation of JAK2 can regulate kinase activity and platinum drug resistance.

Discussion of Examples 2-7. In examples 2-7, data demonstrated that SENP1 controled JAK2 function by regulating its cellular localization via deSUMOylation, and deSUMOylation of JAK2 by SENP1 indirectly regulated JAK2/STAT signaling pathway by shuttling JAK2 between cytoplasm and nucleus. Data also demonstrated that elevated expression level of SENP1 promoted cytoplasmic accumulation of JAK2, resulting in the activation of JAK2/STAT pathway. It was found in the examples that activated JAK2/STAT/anti-apoptosis signaling led to platinum-resistance in ovarian cancer cells. The unexpected findings of examples 2-7 showing a novel SENP-1-mediated mechanism resulted in the synthesis of several potent SENP1 inhibitors which overcame cisplatin-resistance in ovarian cancer. A schematic generally demonstrating findings of the present disclosure is shown in FIG. 14.

Methods Used in Examples 2-7

Cell culture and resistance cell line establishment. IGROV1 cells, U2OS (HTB-96; ATCC), HEK293T (CRL-11268; ATCC) and SKOV3 cells (HTB-77; ATCC) were cultured at 37° C. in DMEM with 10% Fetal Bovine Serum (FBS). PEO1 (10032308; Sigma-Aldrich), PEO4 (10032309; Sigma-Aldrich), PEO14 (10032311; Sigma-Aldrich) and PEO23 cells (10032313; Sigma-Aldrich) were cultured at 37° C. in RPMI-1640 with 10% FBS. OV90 (CRL-11732; ATCC) was cultured in medium containing 1:1 MCDB 105 (Sigma) and M199 (Sigma) supplemented with 10% FBS at 37° C. All the cells were cultured at in a humidified incubator with 5% $CO_2$ atmosphere. Cisplatin resistant cell lines, including SKOV3 CR, IGROV1 CR and OV90 CR, were generated using an approach similar to that reported in Zhou et al., (2018) *Oncogene* 37, 3981-3997, the disclosure of which is incorporated herein in its entirety.

Mass spectrometry. Proteins were stained in SDS-PAGE gels with Coomassie blue. Gel lanes were subsequently sliced and digested in-gel overnight at 37° C. with trypsin. Peptides were eluted in 40% of acetonitrile with re-suspension in 20 μl of 2% formic acid before second extraction. Samples were then dried in a Savant SpeedVac, and resuspended in a 5% methanol/0.1% formic acid solution. Tryptic peptides were separated on C18 reverse phase columns, and were analyzed by Thermo Proteome Discoverer (version 2.1.1.21, Thermo). Proteins were identified by using the Mascot (version:2.3.01) search engine against the Homo sapiens (Human)-Uniprot (TrEMBL) protein databases.

In vitro SUMOylation assay. The SUMOylation reactions were performed according to the manufacture's instruction (BML-UW8955-0001; ENZO). Briefly, 200 nM of purified HIS-JAK2 was suspended in reaction buffer (20 μl) containing Mg-ATP, SUMO E1, SUMO E2 and recombinant SUMOs. RanGAP1 (provided in the kit) was used as the substrate for positive control. The reaction was incubated at 37° C. for 60 minutes and terminated by using 20 μl of SDS loading buffer. For deSUMOylation assay, SENP1 was added 60 minutes after SUMOylation reaction and incubated for additional 60 min. The reactions were then subjected to Western blot to evaluate SUMOylation level.

Protein expression and purification. pET28a-JAK2 and its mutant was transformed in BL21 (DE3) *E. coli* cells by heat shot method at 42° C. and grown in Luria Broth (LB) at 37° C. *E. coli* cells were induced with 0.5 mM IPTG to induct protein expression. Cells were harvested by centrifugation at 5,000 g, 4° C. for 15 min and the pellet was resuspended in lysis buffer (20 mM Tris pH 7.9, 500 mM NaCl, 5 mM imidazole, 2 mM DTT and 1× protease inhibitor cocktail). Cells were then sonicated and centrifuged at 14,000 g, 4° C. for 15 min. 1 ml of Ni-NTA was added to the supernatant and incubated at 4° C. with end-to-end mixing for 2 hours and subjected to a column. The Ni-NTA resin was washed with 10 ml wash buffer (20 mM Tris pH 7.9, 250 mM NaCl, 15 mM Imidazole and 0.5 mM DTT) and eluted with 1 ml elution buffer (20 mM Tris pH 7.9, 250 mM NaCl and 1 M imidazole). The elute was then concentrated by using a protein concentrator (Thermo Scientific™ Pierce™) and resuspend in dialysis buffer (50 mM Tris pH 7.9, 50 mM NaCl, 2 mM DTT, and 10% glycerol). The purified protein was stored at −80° C. pGEX-4T1-SENP1 and its mutant were purified using following buffers: lysis buffer (1 mM DTT, and 1× protease inhibitor cocktail, 800 mM NaCl, 5 mM EDTA, 50 mM Tris-pH8.0, 0.1% Triton x-100), wash buffer (800 mM NaCl, 5 mM EDTA, 50 mM Tris-pH8.0, 0.1% Triton x-100), elution buffer (40 mM glutathione, 800 mM NaCl, 5 mM EDTA, 50 mM Tris-pH8.0, 0.1% Triton x-100), dialysis buffer (50 mM Tris pH 7.9, 50 mM NaCl, 2 mM DTT, and 10% glycerol).

RNA interference. siRNA transfections were performed with 100 nm siRNA oligonucleotide duplexes using Lipofectamine™ RNAiMAX (Invitrogen) according to the manufacturer's instructions. Cells were harvested for analysis 48 hours after transfection. siRNA oligonucleotides against SENP1 were purchased to target non-coding sequences (cat. no. D-006357-01-0002, D-006357-01-0002, Dharmacon). Two siRNAs were obtained similar knockdown efficiency. Negative control GL2: 5'-AACGTACGCGGAATACTTCGA dTdT-3'.

Immunofluorescence microscopy. Cells grown on coverslips in 6-well plates were transfected with siRNA or plasmid for 48 hours. After fixation with 4% paraformaldehyde in PBS for 10 min, cells were penetrated with 0.05% Triton x-100 in PBS for 5 min. Cells were then blocked with blocking buffer (3% BSA in 0.02% Triton x-100 PBS) for 30 min, followed by incubation with primary antibody overnight. The antibody was then washed with washing buffer (0.02% Triton x-100 in PBS) 3×5 min, followed by incubation with 512 nm-conjugated secondary antibody for 45 min. After washing, the cells were counterstained with 15 μl of 10 ng/ml DAPI and the fluorescence was visualized by Zeiss Axioskop fluorescence microscope and analyzed by Zeiss AxioVision deconvolution software.

Cell viability assay. Cells were seeded at 3,000 cells/well in 96-well plates were treated with drugs, followed by incubation for 48 hours, after which cell viability was detected using Sulforhodamine B (SRB) assay (64). Absorbance at 510 nm was detected using a SpectraMax Reader (Molecular Devices) and analyzed with SoftMax Analysis Software (Molecular Devices). Combinational index (CI) values were calculated using CompuSyn software.

Clonogenic Assay. Cells seeded in 6-well plates were treated with cisplatin, Mc or an equivalent volume of DMSO for 48 hours. Thereafter, the cells were incubated in drug free media for 14 days. Colonies were visualized by crystal violet staining, imaged with an EPSON scanner with Photoshop software and county using Quantity One® software.

Genome-wide RNA-sequencing (RNA-Seq). The assay was performed similar to that previously described in Zhou et al., (2018) *Oncogene* 37, 3981-3997, the disclosure of which is incorporated herein in its entirety. Briefly, cells growing in log phase were harvested and RNA isolation was completed using the Qiagen miRNeasy Mini Kit. RNA was then converted into cDNA libraries using the Illumina TruSeq Stranded mRNA sample preparation kit (Illumina #RS-122-2103). Read counts of each sample were normalized with DESeq and ran against their negative binomial two sample test to find significant genes that higher transcript abundance in either the IGROV1 or IGROV1 CR. Genes with false discovery rate (FDR)$<$0.05, fold change larger than 2 or smaller than 0.5-fold were considered as differentially expressed genes.

RT-qPCR. The assay was performed similar to that previously described in Zhou et al., (2018) *Oncogene* 37, 3981-3997, the disclosure of which is incorporated herein in its entirety. The expression level of SENP1 was normalized to GAPDH and the results were given as relative copy numbers. Subsequently, the expression level of SENP1 in cisplatin-resistant cells was normalized to that of parental cells. For samples from patients, the expression levels of SENP1 in 61 platinum-sensitive and 32 platinum-resistant patients were measured using GAPDH as internal control. Subsequently, the expression level of SENP1 in platinum-resistant patient samples was normalized to the mean copy number of SENP1 in platinum-sensitive patient samples. All studies were approved by the local ethics committees (institutional review board reference No: UW 05-143 T/806 and UW 11-298) and the studies abide by the Declaration of Helsinki principles. Informed consent was received before inclusion in the study.

Docking. Docking and scoring were performed by using Schrödinger software package. LigPrep was incorporated to refine UA (ligand). Ionization states within pH=7.0±2.0 were selected for docking. SENP1 crystal structure was downloaded from protein databank. Protein structure was optimized by using Protein Preparation Wizard to add missing hydrogen atoms, correct metal ionization states, and remove co-crystallized water molecules. The Induced Fit protocol was then used for UA and SENP1 docking. The receptor grid center was set as Gly96-Gly97, and a 10 Å side length of cubic grid was allowed in docking. To allow binding domain flexibility, residues within 5.0 Å of ligand poses were refined. The docking results were converted into PDB file and visualized by using Chimera-1.13.

Animal experiments. Xenograft experiments were performed in 6-week female BALB/c athymic nude mice (Jackson Laboratory) by subcutaneously injecting $5\times10^6$ IGROV1 CR cells within 50% Matrigel gelatinous protein mixture (Corning). Mice were randomized to receive treatment after reached a minimum tumor volume of 150 $mm^3$. 4 groups of mice (5 mice per group) were treated intraperitoneally with vehicle, cisplatin (8 mg/kg/2 day), UA (10 mg/kg/2 days) and combination of UA and cisplatin (10 mg/kg/2 day of UA+8 mg/kg/2 day of cisplatin) for 2 weeks. A minimum of 6 tumors per group were assessed. The tumor volume was calculated according to the formula: length×($width^2$)/2.

Immunohistochemistry. Immunohistochemical (IHC) staining and scoring were performed similar to that previously described n Zhou et al., (2018) *Oncogene* 37, 3981-3997, the disclosure of which is incorporated herein in its entirety. The quantification of immunohistochemical staining was scored blindly at least by two independent observers.

Statistical analysis. GraphPad Prism 5.0 software was used for statistical analysis. Data were represented as the mean±S.D. Statistical analysis was performed using one-way ANOVA or Student's t test. P<0.05 was considered significant. For Kaplan Meier survival analysis, a Log-rank (Mantel-Cox) test was used to compare each of the arms.

Figure 15A:
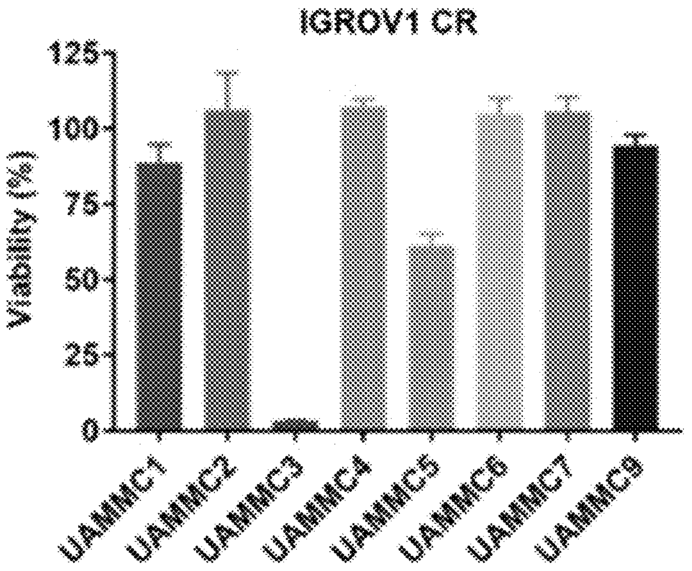
FIGS. 15A-15O depict images illustrating identification of UAMMC9 as a potential SENP1 inhibitor candidate.
Figure 15B:
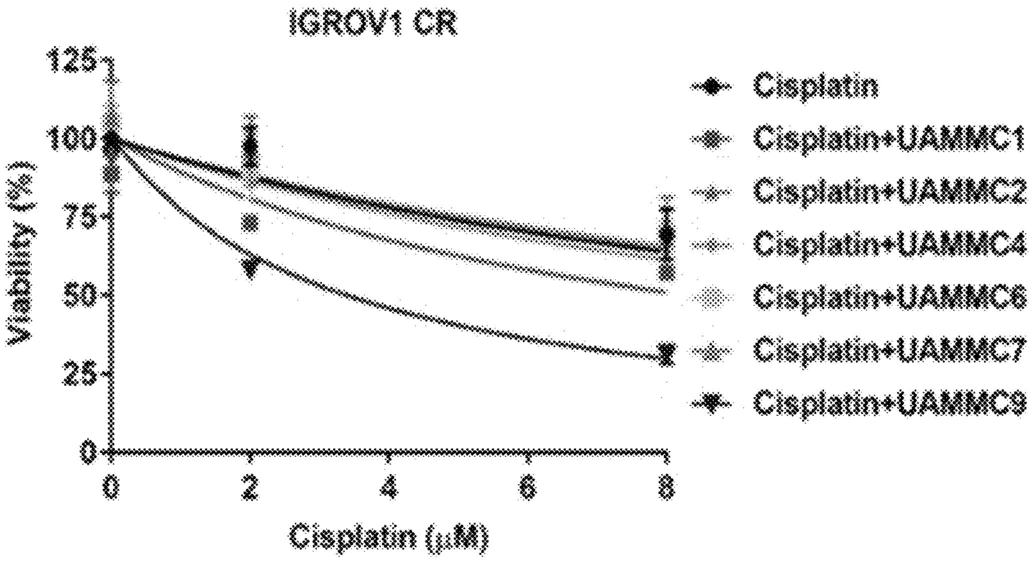
FIG. 15B shows the synergistic effects of cisplatin and UAMMC1, UAMMC2, UAMMC4, UAMMC6, UAMMC7 or UAMMC9 in IGROV1 CR cells.
Figure 15C:
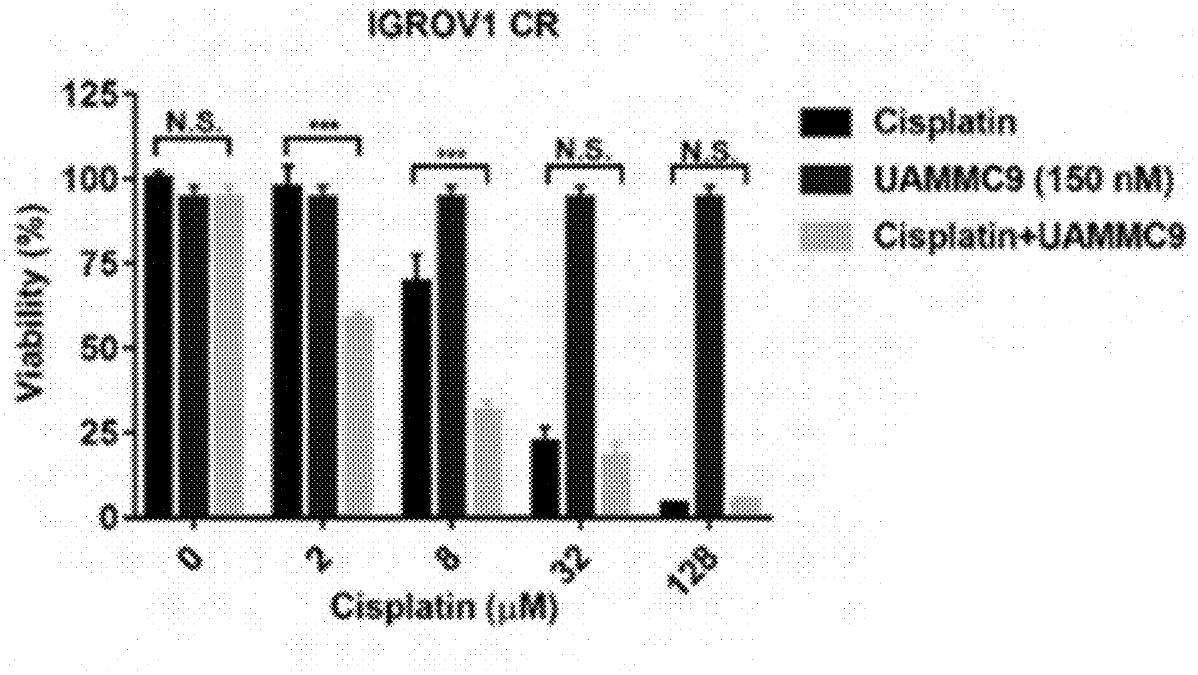
FIG. 15C shows the synergistic effects of cisplatin and UAMMC9 in IGROV1 CR cells. N.S., not significant, * P<0.001.

Example 8. Ursolic Acid Derivatives for Use on Platinum-Resistant Ovarian Cancer Cells The toxicity of the compounds synthesized as described in example 1, including UAMMC1, UAMMC2, UAMMC3, UAMMC4, UAMMC5, UAMMC6, UAMMC7, UAMMC9, was determined in in cisplatin-resistant IGROV1 cells (IGROV1 CR). Both UAMMC3 and UAMMC5 were excluded because of their higher toxicity at 150 nM (FIG. 15A). Next, the synergy of cisplatin with other UAMMCs (150 nM) was examined in in IGROV1 CR cells, and it was found that UAMMC9 showed the best synergy with cisplatin and deceased the $IC_{50}$ of cisplatin by 4.19 fold (FIGS. 15B and 15C; Table 1).

TABLE 1

Cisplatin $IC_{50}$ with 150 nM of UAMMCs on IGROV1 CR cells.

| | Cisplatin | Cisplatin + UAMMC1 | Cisplatin + UAMMC2 | Cisplatin + UAMMC4 | Cisplatin + UAMMC6 | Cisplatin + UAMMC7 | Cisplatin + UAMMC9 |
|---|---|---|---|---|---|---|---|
| IC50 (μM) | 14.22 | 8.35 | 13.92 | 12.74 | 14.47 | 15.35 | 3.40 |

Figure 15D:
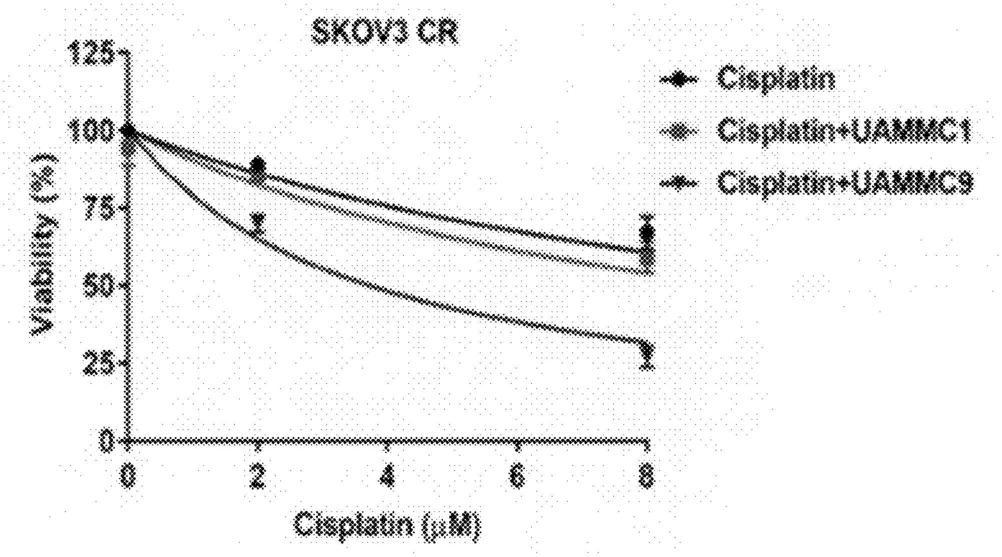
FIG. 15D shows the synergistic effects of cisplatin and UAMMC1 or UAMMC9 in SKOV3 CR cells.
Figure 15E:
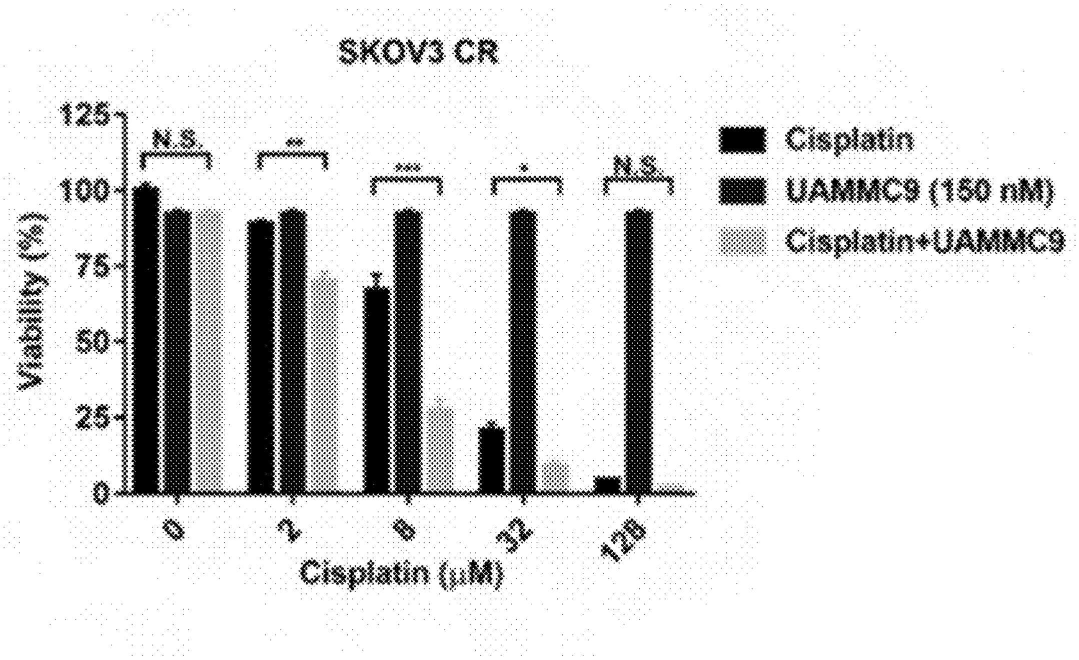
FIG. 15**E shows the synergistic effects of cisplatin and UAMMC9 in SKOV3 CR cells. N.S., not significant, *P<0.05, P<0.01, * P<0.001.
FIG. 15F shows UAMMC9 increased JAK2 SUMOylation in IGROV1 CR and SKOV3 CR cells. UAMMC9 concentration: 150 nM.
FIG. 15G shows a cellular thermal shift assay used to examine the interaction of UAMMC9 with SENP1. SENP1 stability was analyzed using Western blot against SENP1 antibody.
FIG. 15H shows quantification of the non-denatured SENP1 fraction detected in Western blot assay of FIG. 15G.
FIGS. 15I and 15J show UAMMC9 inhibited SENP1 activity in vivo.
FIGS. 15K and 15L show UAMMC9 inhibited SENP1 activity in vitro.
FIG. 15M shows UAMMC9 decreased pSTAT3 (Tyr705) by JAK2 in vitro.
FIG. 15N shows JAK2 kinase activity inhibition in response to UAMMC9.
Figure 15F:
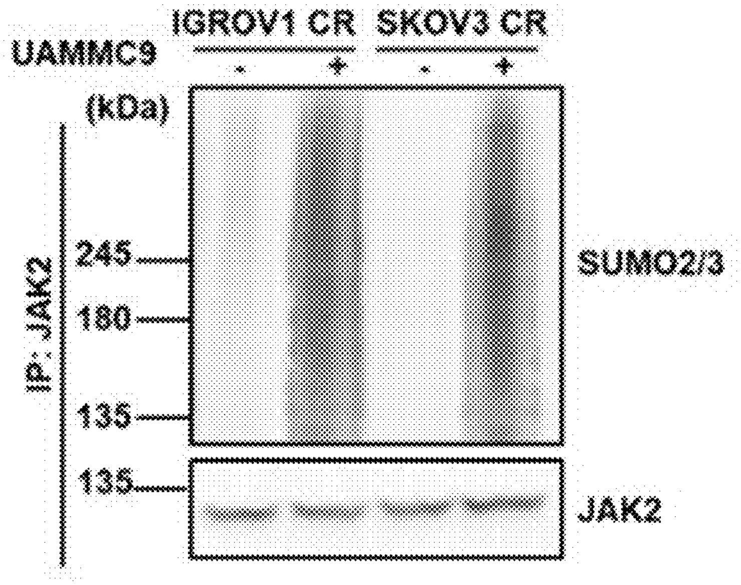

The results were confirmed in cisplatin-resistant SKOV3 cells (SKOV3 CR) (FIGS. 15D and 15E; Table 2). As shown in FIG. 15F, UAMMC9 inhibited SENP1 activity in both IGROVI CR and SKOV3 CR cells.

TABLE 2

Cisplatin IC4 with 150 nM of UAMMCs on SKOV3 CR cells.

| | Cisplatin | Cisplatin + UAMMC1 | Cisplatin + UAMMC9 |
|---|---|---|---|
| IC50 (μM) | 12.44 | 9.47 | 3.73 |

Figure 15G:
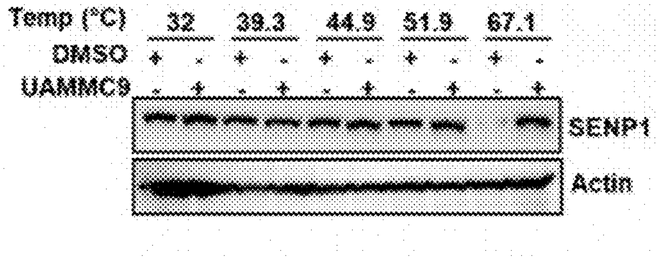
Figure 15H:
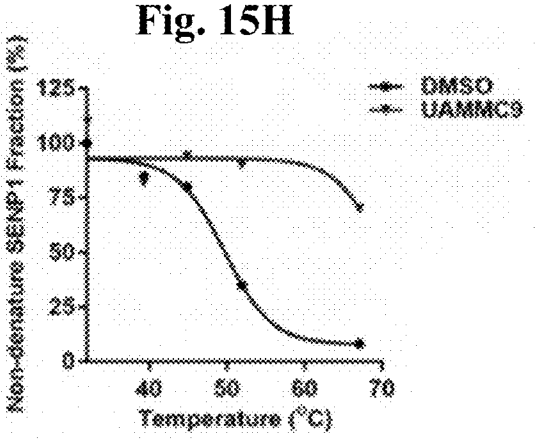

To determine whether UAMMC9 binds to SENP1 directly, cellular thermal shift assays were conducted in which a small molecule binds to a protein resulting in thermal stabilization of the protein. Using this assay, it was found that at higher temperature SENP1 protein was stabilized upon treatment with UAMMC9 compared to control DMSO treatment (FIGS. 15G and 15H), suggesting a direct interaction between UAMMC9 and SENP1.

Figure 15I:
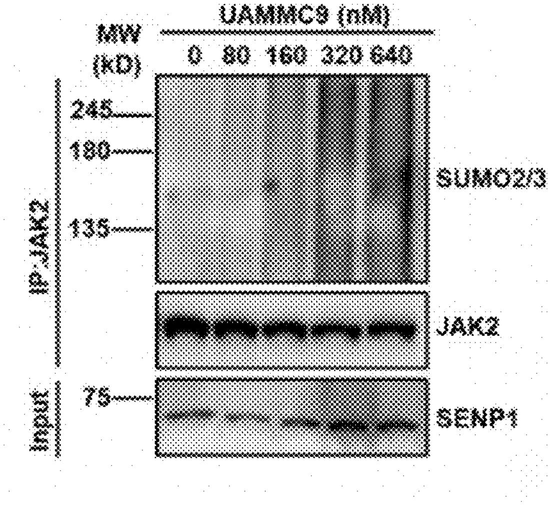
Figure 15J:
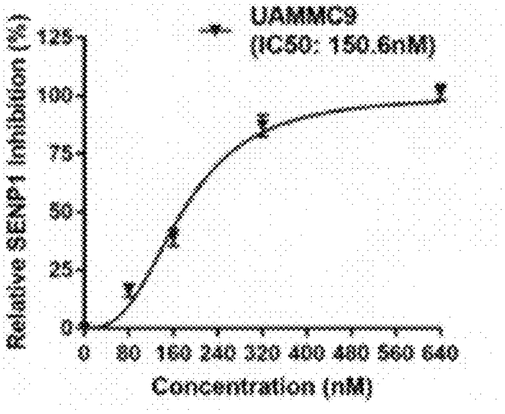
Figure 15K:
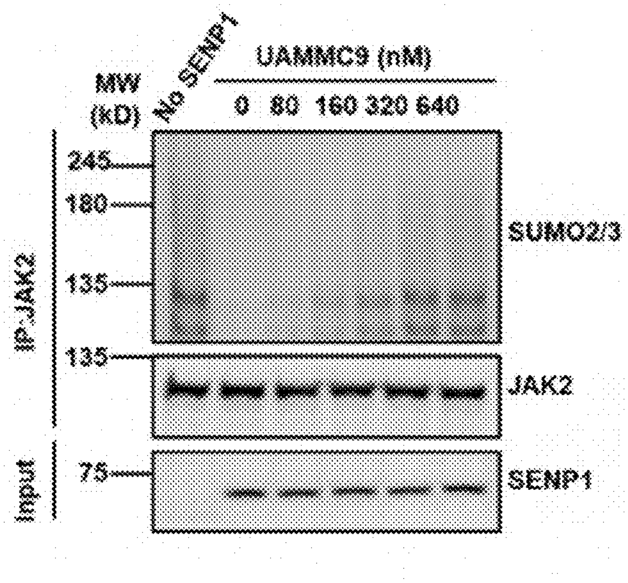
Figure 15L:
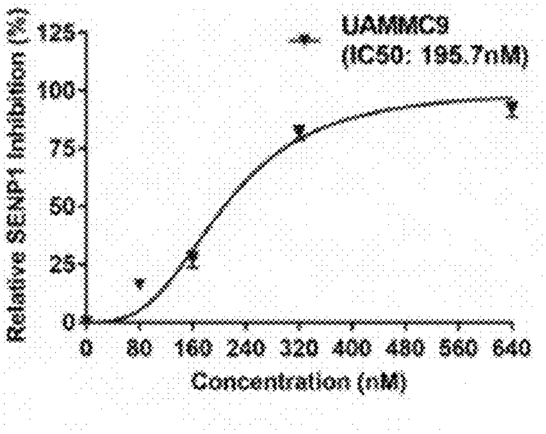

Next, JAK2 was immunoprecipitated and the SUMOylation level of JAK2 evaluated using antibody against SUMO2/3 in UAMMC9 treated cells. As shown in FIGS. 15I and 15J, UAMMC9 significantly increased the SUMOylation levels of JAK2 at 150.6 nM. To further determine whether UAMMC9 inhibited JAK2 SUMOylation levels in vitro, in vitro deSUMOylation assays were performed by using purified recombinant His-JAK2 and GST-SENP1 proteins. It was found that UAMMC9 increased JAK2 SUMOylation levels in vitro with IC50 at 195.7 nM (FIGS. 15K and 15L). Taken together, these data strongly suggested that UAMMC9 directly inhibited SENP1 deSUMOylase activity.

Figure 15M:
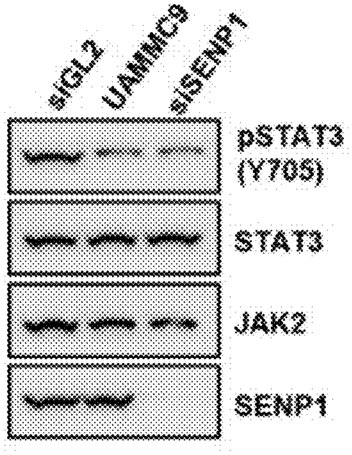
Figure 15N:
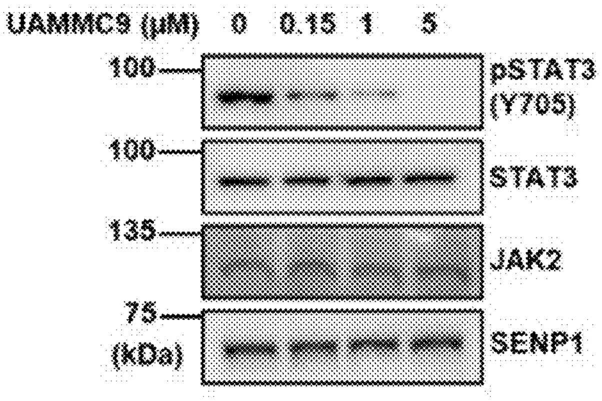
Figure 15O:
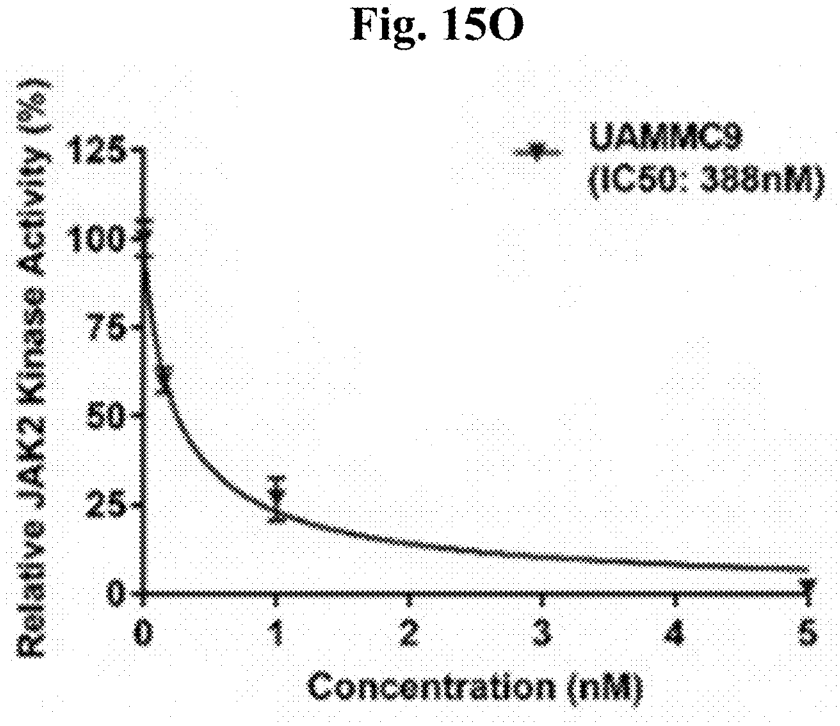

It was next next examined whether UAMMC9 could affect JAK2 activity. To this end, cell-free kinase assays were performed using JAK2 purified from cells treated with siSENP1 or UAMMC9. The purified JAK2 from cells treated with siSENP1 or UAMMC9 showed decreased phosphorylation on recombinant substrate STAT3 proteins (FIGS. 15M-15O), indicating that the activity of JAK2 was significantly reduced by UAMMC9.

What is claimed:

1. A compound represented by formula I or a pharmaceutically acceptable salt thereof:

(I)

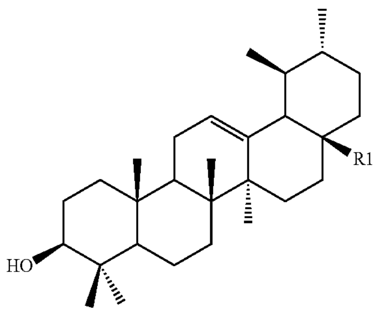

wherein R1 is selected from the group consisting of hydrogen, hydroxyl, hydroxymethyl, formyl, or

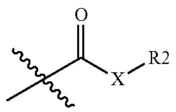

wherein X is NH or O or S, and $R_2$ is hydrogen, unsubstituted or substituted $C_1$-$C_6$ alkyl.

2. A pharmaceutical composition comprising at least one compound of claim 1, and at least one pharmaceutically acceptable excipient.

3. The compound of claim 1, wherein the compound is

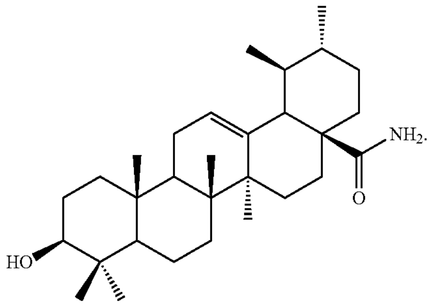

4. The compound of claim 1, wherein the compound is

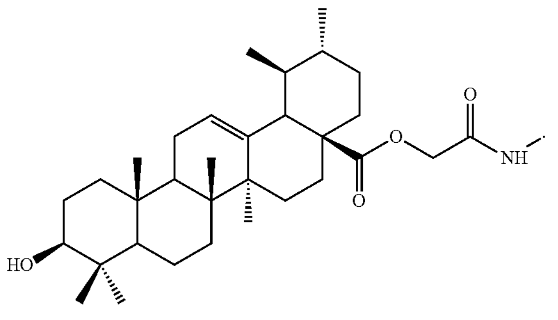

5. The compound of claim 1, wherein the compound is

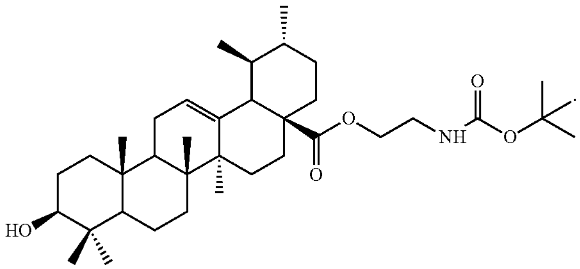

6. The compound of claim 1, wherein the compound is

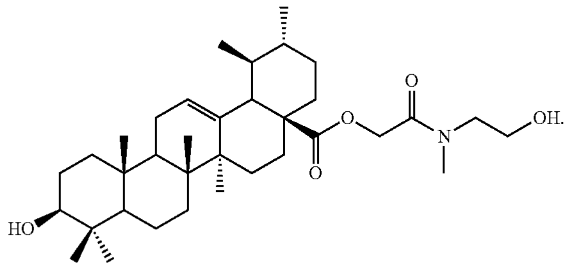

7. The compound of claim 1, wherein the compound is

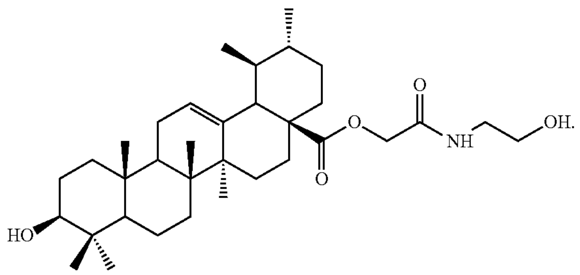

8. The compound of claim 1, wherein the compound is
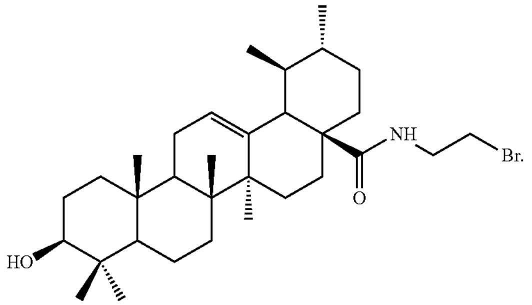
9. The compound of claim 1, wherein the compound is
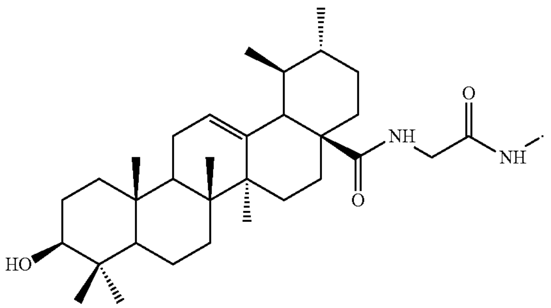
10. The compound of claim 1, wherein the compound is
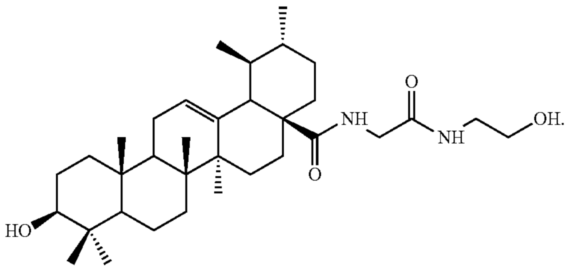
11. The compound of claim 1, wherein the compound is
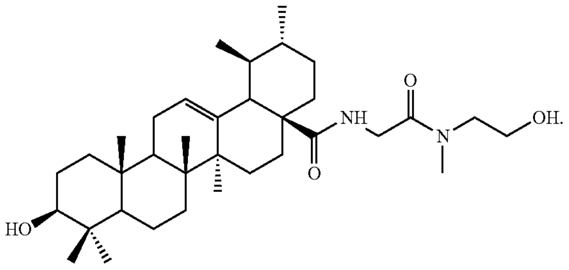
12. The compound of claim 1, wherein the compound is
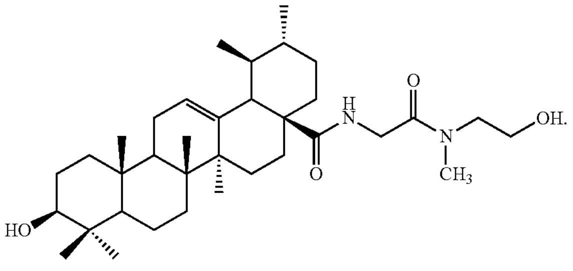
13. The compound of claim 1, wherein the compound inhibits sentrin-specific protease 1 (SENP1).
* * * * *